(12) United States Patent
Luo et al.

(10) Patent No.: US 7,737,154 B2
(45) Date of Patent: Jun. 15, 2010

(54) CRF RECEPTOR ANTAGONISTS AND METHODS RELATING THERETO

(75) Inventors: Zhiyong Luo, New York, NY (US); Deborah H Slee, Cardiff, CA (US); John Williams, San Diego, CA (US)

(73) Assignee: Smithkline Beecham (Cork) Limited, Currabinny, Carrigaline, County Cork (IE)

( * ) Notice: Subject to any disclaimer, the term of this patent is extended or adjusted under 35 U.S.C. 154(b) by 668 days.

(21) Appl. No.: 10/596,648

(22) PCT Filed: Dec. 20, 2004

(86) PCT No.: PCT/IB2004/004234

§ 371 (c)(1), (2), (4) Date: May 29, 2007

(87) PCT Pub. No.: WO2005/063755

PCT Pub. Date: Jul. 14, 2005

(65) Prior Publication Data

US 2007/0287705 A1    Dec. 13, 2007

Related U.S. Application Data

(60) Provisional application No. 60/532,031, filed on Dec. 22, 2003.

(51) Int. Cl.
C07D 487/04 (2006.01)
A61K 31/519 (2006.01)
A61P 25/24 (2006.01)
A61P 25/22 (2006.01)

(52) U.S. Cl. .................... 514/259.1; 544/281
(58) Field of Classification Search ............... 544/281; 514/259.3
See application file for complete search history.

(56) References Cited

U.S. PATENT DOCUMENTS

| | | | |
|---|---|---|---|
| 6,060,478 A | 5/2000 | Gilligan et al. | |
| 6,313,124 B1 | 11/2001 | He et al. | |
| 6,589,947 B1 | 7/2003 | Hamanaka et al. | |
| 7,253,284 B2 | 8/2007 | DiFabio et al. | |
| 7,279,474 B2 | 10/2007 | Capelli et al. | |
| 7,462,622 B2 | 12/2008 | DiFabio et al. | |
| 2003/0139426 A1 | 7/2003 | Wilde et al. | |
| 2005/0187224 A1 | 8/2005 | Gebauer et al. | |
| 2007/0004708 A1 | 1/2007 | Andriotti et al. | |
| 2007/0021429 A1 | 1/2007 | St. Denis | |
| 2007/0066640 A1 | 3/2007 | Castigtioni et al. | |
| 2007/0219232 A1 | 9/2007 | DiFabio et al. | |
| 2007/0293511 A1 | 12/2007 | Luo et al. | |
| 2008/0064719 A1 | 3/2008 | Lanier et al. | |
| 2008/0194589 A1 | 8/2008 | Lanier et al. | |
| 2008/0306092 A1 | 12/2008 | Hossner | |

FOREIGN PATENT DOCUMENTS

| | | |
|---|---|---|
| GB | 2378702 | 2/2003 |
| WO | 97/29109 A | 8/1997 |
| WO | WO98/03510 | 1/1998 |
| WO | WO98/08847 | 3/1999 |
| WO | WO01/23388 | 4/2001 |
| WO | WO2004/087707 | 10/2004 |

Primary Examiner—Susanna Moore
(74) Attorney, Agent, or Firm—Barbara J. Carter

(57) ABSTRACT

CRF receptor antagonists are disclosed which have utility in the treatment of a variety of disorders, including the treatment of disorders manifesting hypersecretion of CRF in a warm blooded animals, such as stroke. The CRF receptor antagonists of this invention have the following structure (I), including stereoisomers, prodrugs and pharmaceutically acceptable salts thereof, wherein R1, R2, R3, Y, Ar, and het are as defined herein. Compositions containing a CRF receptor antagonist in combination with a pharmaceutically acceptable carrier are also disclosed, as well as methods for use of the same.

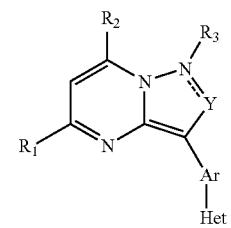

19 Claims, No Drawings

CRF RECEPTOR ANTAGONISTS AND METHODS RELATING THERETO

CROSS-REFERENCE TO RELATED APPLICATION

This application is a 371 of International Application No. PCT/IB2004/004234, filed 20 Dec. 2004, which claims the benefit of U.S. Provisional Application No. 60/532,031, filed 22 Dec. 2003.

FIELD OF THE INVENTION

This invention relates generally to CRF receptor antagonists and to methods of treating disorders by administration of such antagonists to a mammal in need thereof.

BACKGROUND OF THE INVENTION

The first corticotropin-releasing factor (CRF) was isolated from ovine hypothalami and identified as a 41-amino acid peptide (Vale et al., *Science* 213:1394-1397, 1981). Subsequently, sequences of human and rat CRF were isolated and determined to be identical but different from ovine CRF in 7 of the 41 amino acid residues (Rivier et al., *Proc. Natl. Acad. Sci. USA* 80:4851, 1983; Shibahara et al., *EMBO J.* 2:775, 1983).

CRF has been found to produce profound alterations in endocrine, nervous and immune system function. CRF is believed to be the major physiological regulator of the basal and stress-release of adrenocorticotropic hormone ("ACTH"), β-endorphin, and other pro-opiomelanocortin ("POMC")-derived peptides from the anterior pituitary (Vale et al., *Science* 213:1394-1397, 1981). Briefly, CRF is believed to initiate its biological effects by binding to a plasma membrane receptor which has been found to be distributed throughout the brain (DeSouza et al., *Science* 224: 1449-1451, 1984), pituitary (DeSouza et al., *Methods Enzymol.* 124:560, 1986; Wynn et al., *Biochem. Biophys. Res. Comm.* 110:602-608, 1983), adrenals (Udelsman et al., *Nature* 319:147-150, 1986) and spleen (Webster, E. L., and E. B. DeSouza, *Endocrinology* 122:609-617, 1988). The CRF receptor is coupled to a GTP-binding protein (Perrin et al., *Endocrinology* 118:1171-1179, 1986) which mediates CRF-stimulated increase in intracellular production of cAMP (Bilezikjian, L. M., and W. W. Vale, Endocrinology 113:657-662, 1983). The receptor for CRF has now been cloned from rat (Perrin et al., *Endo* 133(6):3058-3061, 1993), and human brain (Chen et al., *PNAS* 90(19):8967-8971, 1993; Vita et al., *FEBS* 335(1):1-5, 1993). This receptor is a 415 amino acid protein comprising seven membrane spanning domains. A comparison of identity between rat and human sequences shows a high degree of homology (97%) at the amino acid level.

In addition to its role in stimulating the production of ACTH and POMC, CRF is also believed to coordinate many of the endocrine, autonomic, and behavioral responses to stress, and may be involved in the pathophysiology of affective disorders. Moreover, CRF is believed to be a key intermediary in communication between the immune, central nervous, endocrine and cardiovascular systems (Crofford et al., *J. Clin. Invest.* 90:2555-2564, 1992; Sapolsky et al., *Science* 238:522-524, 1987; Tilders et al., *Regul. Peptides* 5:77-84, 1982). Overall, CRF appears to be one of the pivotal central nervous system neurotransmitters and plays a crucial role in integrating the body's overall response to stress.

Administration of CRF directly to the brain elicits behavioral, physiological, and endocrine responses identical to those observed for an animal exposed to a stressful environment. For example, intracerebroventricular injection of CRF results in behavioral activation (Sutton et al., *Nature* 297:331, 1982), persistent activation of the electroencephalogram (Ehlers et al., *Brain Res.* 278:332, 1983), stimulation of the sympathoadrenomedullary pathway (Brown et al., *Endocrinology* 110:928, 1982), an increase of heart rate and blood pressure (Fisher et al., *Endocrinology* 110:2222, 1982), an increase in oxygen consumption (Brown et al., *Life Sciences* 30:207, 1982), alteration of gastrointestinal activity (Williams et al., *Am. J. Physiol.* 253:G582, 1987), suppression of food consumption (Levine et al., *Neuropharmacology* 22:337, 1983), modification of sexual behavior (Sirinathsinghji et al., *Nature* 305:232, 1983), and immune function compromise (Irwin et al., *Am. J. Physiol.* 255:R744, 1988). Furthermore, clinical data suggests that CRF may be hypersecreted in the brain in depression, anxiety-related disorders, and anorexia nervosa. (DeSouza, *Ann. Reports in Med. Chem.* 25:215-223, 1990). Accordingly, clinical data suggests that CRF receptor antagonists may represent novel antidepressant and/or anxiolytic drugs that may be useful in the treatment of the neuropsychiatric disorders manifesting hypersecretion of CRF.

The first CRF receptor antagonists were peptides (see, e.g., Rivier et al., U.S. Pat. No. 4,605,642; Rivier et al., *Science* 224:889, 1984). While these peptides established that CRF receptor antagonists can attenuate the pharmacological responses to CRF, peptide CRF receptor antagonists suffer from the usual drawbacks of peptide therapeutics including lack of stability and limited oral activity. Some published patent documents include U.S. Pat. No. 6,313,124, WO 01/23388, and WO 97/29109, all of which disclose pyrazolopyrimidine compounds as CRF antagonists. Published application WO 98/54093 described certain pyrazolopyrimidine compounds as tyrosine kinase inhibitors.

Due to the physiological significance of CRF, the development of biologically-active small molecules having significant CRF receptor binding activity and which are capable of antagonizing the CRF receptor remains a desirable goal. Such CRF receptor antagonists would be useful in the treatment of endocrine, psychiatric and neurological conditions or illnesses, including stress-related disorders in general.

While significant strides have been made toward achieving CRF regulation through administration of CRF receptor antagonists, there remains a need in the art for effective small molecule CRF receptor antagonists. There is also a need for pharmaceutical compositions containing such CRF receptor antagonists, as well as methods relating to the use thereof to treat, for example, stress-related disorders. The present invention fulfills these needs, and provides other related advantages.

SUMMARY OF THE INVENTION

In brief, this invention is generally directed to CRF receptor antagonists, and more specifically to CRF receptor antagonists having the following general structure (I):

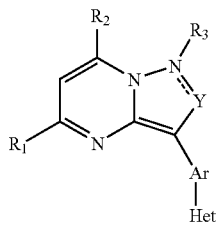

and pharmaceutically acceptable salts, esters, solvates, stereoisomers and prodrugs thereof, wherein $R_1$, $R_2$, $R_3$, Y, Ar, and Het are as defined below.

The CRF receptor antagonists of this invention may have utility over a wide range of therapeutic applications, and may be used to treat a variety of disorders or illnesses, including stress-related disorders. Such methods include administering a pharmaceutically effective amount of a CRF receptor antagonist of this invention, preferably in the form of a pharmaceutical composition, to an animal in need thereof. Accordingly, in another embodiment, pharmaceutical compositions are disclosed containing one or more CRF receptor antagonists of this invention and a pharmaceutically acceptable carrier and/or diluent.

These and other aspects of the invention will be apparent upon reference to the following detailed description. To this end, various references are set forth herein which describe in more detail certain procedures, compounds and/or compositions, and are hereby incorporated by reference in their entirety.

DETAILED DESCRIPTION OF THE INVENTION

The present invention is directed generally to corticotropin-releasing factor (CRF) receptor antagonists.

In a first embodiment, the CRF receptor antagonists of this invention have the following structure (I):

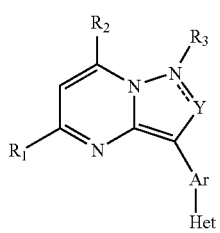

or a pharmaceutically acceptable salt, ester, solvate, stereoisomer or prodrug thereof, wherein:

"- - -" represents the second bond of an optional double bond;

$R_1$ is hydrogen, alkyl, substituted alkyl, heteroaryl, substituted heteroaryl, —$NH_2$, or halogen;

$R_2$ is alkyl, substituted alkyl, —C(O)$NR_7R_8$, aryl, substituted aryl, aryloxyalkyl, substituted aryloxyalkyl, heteroarylalkoxyalkyl, substituted heteroarylalkoxyalkyl, heterocyclealkyl, substituted heterocyclealkyl, arylalkyl, substituted arylalkyl, heteroaryl, or substituted heteroaryl, wherein said heteroaryl or substituted heteroaryl is connected to the pyrimidine ring via a carbon-carbon bond;

$R_3$ is null, hydrogen, or alkyl;

Y is =(CR_4)— or —(C=O)—;

$R_4$ is hydrogen, alkyl, substituted alkyl, thioalkyl, alkylsulfinyl, or alkylsulfonyl;

Ar is phenyl, phenyl substituted with 1 or 2 $R_5$, pyridyl or pyridyl substituted with 1 or 2 $R_5$;

$R_5$ at each occurrence is hydroxy, alkyl, substituted alkyl, alkoxy, substituted alkoxy, cyano, halogen, alkylsulfonyl, or alkylsulfinyl;

Het is heteroaryl optionally substituted with 1 or 2 $R_6$;

$R_6$ at each occurrence is hydroxy, alkyl, substituted alkyl, alkoxy, substituted alkoxy, cyano, or halogen; and $R_7$ and $R_8$ are independently hydrogen, alkyl, substituted alkyl, aryl, substituted aryl, heterocycle, substituted heterocycle, arylalkyl, substituted arylalkyl, heterocyclealkyl or substituted heterocyclealkyl; or $R_7$ and $R_8$ taken together with the nitrogen to which they are attached form a heterocyclic ring or a substituted heterocyclic ring.

As used herein, the above terms have the following meaning:

"Alkyl" means a straight chain or branched, acyclic or cyclic, unsaturated or saturated hydrocarbon containing from 1 to 10 carbon atoms, while the term "lower alkyl" has the same meaning as alkyl but contains from 1 to 6 carbon atoms. Representative saturated straight chain alkyls include methyl, ethyl, n-propyl, n-butyl, n-pentyl, n-hexyl, and the like; while saturated branched alkyls include isopropyl, sec-butyl, isobutyl, tert-butyl, isopentyl, and the like. Representative saturated cyclic alkyls include cyclopropyl, cyclobutyl, cyclopentyl, cyclohexyl, —$CH_2$-cyclopropyl, —$CH_2$-cyclobutyl, —$CH_2$-cyclopentyl, —$CH_2$-cyclohexyl, and the like; while unsaturated cyclic alkyls include cyclopentenyl and cyclohexenyl, and the like. Cyclic alkyls, also referred to as "homocyclic rings," and include di- and poly-homocyclic rings such as decalin and adamantyl. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1 butynyl, and the like.

"Alkylidenyl" represents a divalent alkyl from which two hydrogen atoms are taken from the same carbon atom, such as =$CH_2$, =$CHCH_3$, =$CHCH_2CH_3$, =C($CH_3$)$CH_2CH_3$, and the like.

"Aryl" means an aromatic carbocyclic moiety such as phenyl or naphthyl.

"Arylalkyl" means an alkyl having at least one alkyl hydrogen atom replaced with an aryl, such as benzyl (i.e., —$CH_2$-phenyl), —$CH_2$-(1- or 2-naphthyl), —($CH_2$)$_2$-phenyl, —($CH_2$)$_3$-phenyl, —CH(phenyl)$_2$, and the like.

"Aryloxyalkyl" means an aryl attached through an oxygen bridge to an alkyl (i.e., aryl-O-alkyl-) such as -methyl-O-phenyl, and such.

"Heteroaryl" means an aromatic heterocycle ring of 5- to 10-members and having at least one heteroatom selected from nitrogen, oxygen and sulfur, and containing at least 1 carbon atom, including both mono- and bicyclic ring systems. Representative heteroaryls include (but are not limited to) furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl.

"Heteroarylalkyl" means an alkyl having at least one alkyl hydrogen atom replaced with a heteroaryl, such as —CH$_2$-pyridinyl, —CH$_2$-pyrimidinyl, and the like.

"Heterocycle" (also referred to herein as a "heterocycle ring") means a 5- to 7-membered monocyclic, or 7- to 14-membered polycyclic, heterocycle ring which is either saturated, unsaturated or aromatic, and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring as well as tricyclic (and higher) heterocyclic rings. The heterocycle may be attached via any heteroatom or carbon atom. Heterocycles include heteroaryls as defined above. Thus, in addition to the aromatic heteroaryls listed above, heterocycles also include (but are not limited to) morpholinyl, pyrrolidinonyl, pyrrolidinyl, piperidinyl, piperizinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

"Heterocyclealkyl" means an alkyl having at least one alkyl hydrogen atom replaced with a heterocycle, such as —CH$_2$-morpholinyl, and the like. The term "substituted" as used herein refers to any group (e.g., alkyl, aryl, arylalkyl, heteroaryl, heteroarylalkyl, heterocycle or heterocyclealkyl) wherein at least one hydrogen atom is replaced with a substituent. In the case of a keto substituent ("—C(=O)—") two hydrogen atoms are replaced. "Substituents" within the context of this invention include halogen, hydroxy, cyano, nitro, amino, alkylamino, dialkylamino, alkyl, alkoxy, thioalkyl, haloalkyl, hydroxyalkyl, aryl, substituted aryl, arylalkyl, substituted arylalkyl, heteroaryl, substituted heteroaryl, heteroarylalkyl, substituted heteroarylalkyl, heterocycle, substituted heterocycle, heterocyclealkyl, substituted heterocyclealkyl, —NR$_a$R$_b$, —NR$_a$C(=O)R$_b$, —NR$_a$C(=O)NR$_a$R$_b$, —NR$_a$C(=O)OR$_b$ —NR$_a$SO$_2$R$_b$, —OR$_a$, —C(=O)R$_b$ —C(=O)OR$_a$, —C(=O)NR$_a$R$_b$, —OC(=O)NR$_a$R$_b$, —SH, —SR$_a$, —SOR$_a$, —S(=O)$_2$R$_a$, —OS(=O)$_2$R$_a$, —S(=O)$_2$OR$_a$, wherein R$_a$ and R$_b$ are the same or different and independently hydrogen, alkyl, haloalkyl, substituted alkyl, aryl, substituted aryl, arylalkyl, substituted arylalkyl, heteroaryl, substituted heteroaryl, heteroarylalkyl, substituted heteroarylalkyl, heterocycle, substituted heterocycle, heterocyclealkyl or substituted heterocyclealkyl.

"Halogen" means fluoro, chloro, bromo or iodo.

"Haloalkyl" means an alkyl having at least one hydrogen atom replaced with halogen, such as trifluoromethyl and the like. Haloalkyl is a specific embodiment of substituted alkyl, wherein alkyl is substituted with one or more halogen atoms.

"Alkoxy" means an alkyl attached through an oxygen bridge (i.e., —O-alkyl) such as —O-methyl, —O-ethyl, and the like.

"Thioalkyl" means an alkyl attached through a sulfur bridge (i.e., —S-alkyl) such as —S-methyl, —S-ethyl, and the like.

"Alkylamino" and "dialkylamino" mean one or two alkyl moieties attached through a nitrogen bridge (i.e., —NHalkyl or —N(alkyl)(alkyl)) such as methylamino, ethylamino, dimethylamino, diethylamino, and the like.

"Hydroxyalkyl" means an alkyl substituted with at least one hydroxy group.

"Mono- or di(cycloalkyl)methyl" represents a methyl group substituted with one or two cycloalkyl groups, such as cyclopropylmethyl, dicyclopropylmethyl, and the like.

"Alkylcarbonylalkyl" represents an alkyl substituted with a —C(=O)alkyl group.

"Alkylcarbonyloxyalkyl" represents an alkyl substituted with a —C(=O)alkyl group or a —OC(=O)alkyl group.

"Alkoxyalkyl" represents an alkyl substituted with a —O-alkyl group.

"Alkylthioalkyl" represents a alkyl substituted with a —S-alkyl group.

"Mono- or di(alkyl)amino represents an amino substituted with one alkyl or with two alkyls, respectively.

"Mono- or di(alkyl)aminoalkyl" represents an alkyl substituted with a mono- or di(alkyl)amino.

"Alkylsulfonyl or alkylsulfinyl" represents an alkyl substituted with a (—S(=O)$_2$—) or (—S(=O)—) functionality, respectively.

Embodiments of this invention presented herein are for purposes of example and not for purposes of limitation. In a first embodiment of the invention, R$_3$ is null and Y is =(CR$_4$)— in the following structure (II), and in a further embodiment Y is —(C=O)— in the following structure (III).

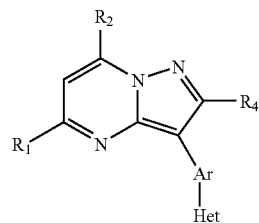

(II)

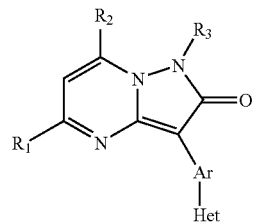

(III)

Further embodiments of this invention have structure (IV) when R$_2$ is phenyl, R is an optional substituent of said phenyl, and Y is =(CR$_4$)—.

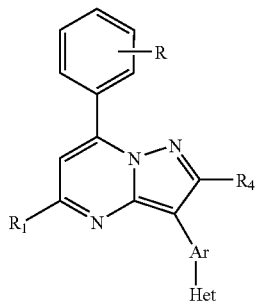

(IV)

In further embodiments of this invention wherein Y is =(CR$_4$)—, Ar is phenyl substituted with 2 R$_5$ in structure (V) and Het is pyridyl substituted with 1 R$_6$ in structure (IV).

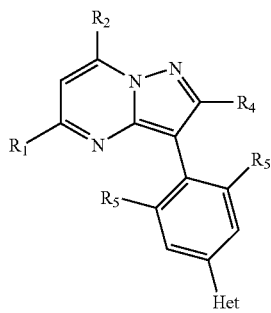

(V)

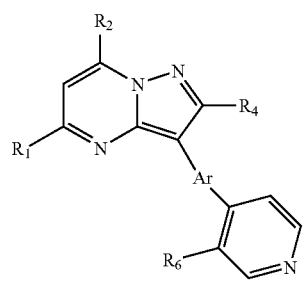

(VI)

The compounds of the present invention may generally be utilized as the free base. Alternatively, the compounds of this invention may be used in the form of acid addition salts. Acid addition salts of the free base amino compounds of the present invention may be prepared by methods well known in the art, and may be formed from organic and inorganic acids. Suitable organic acids include maleic, fumaric, benzoic, ascorbic, succinic, methanesulfonic, acetic, oxalic, propionic, tartaric, salicylic, citric, gluconic, lactic, mandelic, cinnamic, aspartic, stearic, palmitic, glycolic, glutamic, and benzenesulfonic acids. Suitable inorganic acids include hydrochloric, hydrobromic, sulfuric, phosphoric, and nitric acids. Thus, the term "pharmaceutically acceptable salt" of structure (I) is intended to encompass any and all pharmaceutically acceptable salt forms.

In general, the compounds of structure (I) may be made according to the organic synthesis techniques known to those skilled in this field, as well as by the representative methods set forth in the Examples. Examples of synthetic procedures which may be used to prepare compounds according to the invention are illustrated in Reaction Schemes 1-3.

Reaction Scheme 1

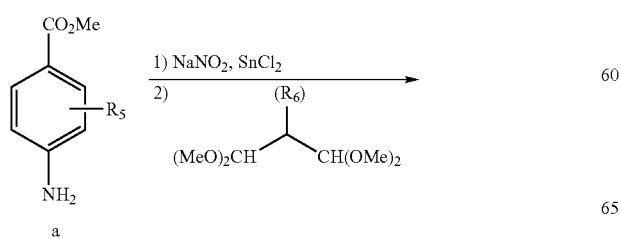

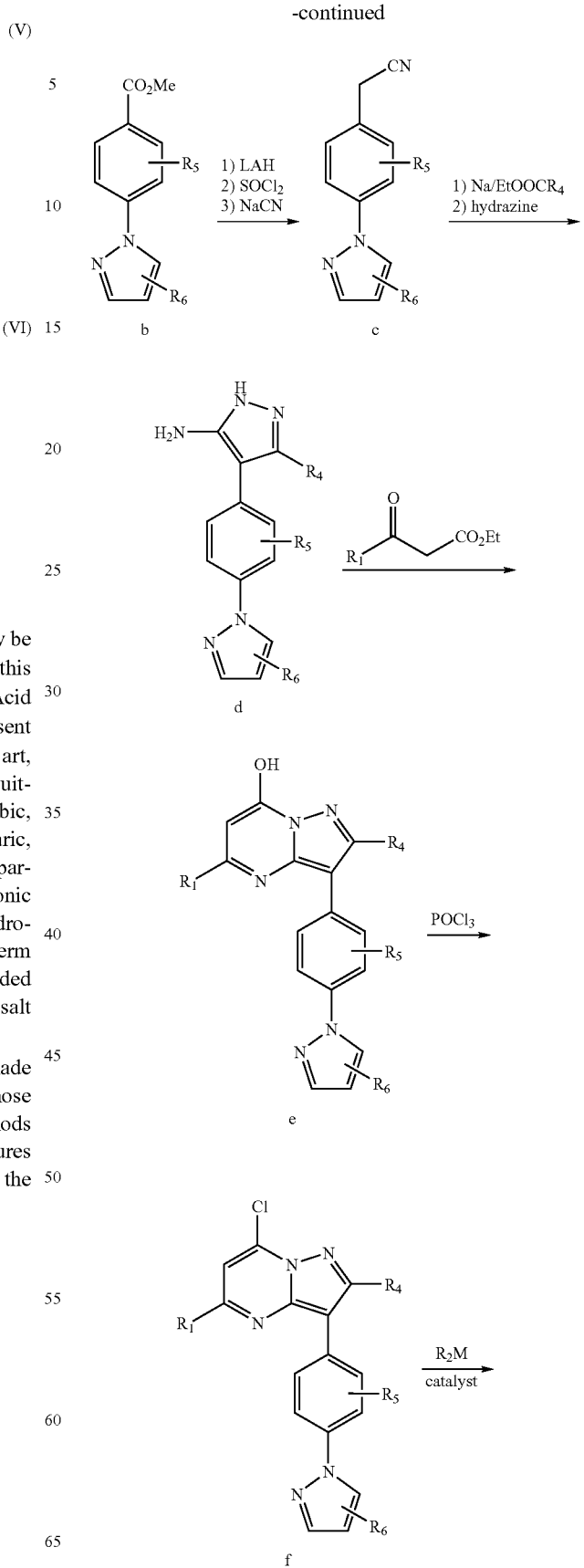

-continued

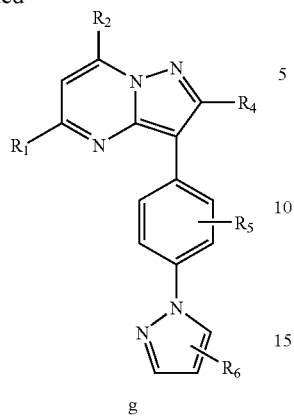

g

The amino functionality of 4-aminobenzoate a may be condensed with an, optionally, substituted malonaldehyde to give the corresponding 4-pyrazol-1-yl benzoate b. After reaction with LAH, $SOCl_2$, and NaCN to give conversion to the pyrazolophenylacetonitrile compound c, reaction with Na/ethyl carboxylic acid ester and hydrazine yields the bis-pyrazole d. Reaction with the appropriately substituted β-keto ester gives pyrazolopyrimidine e which reacts with $POCl_3$ to give the chloride f. Reaction of the chloride f with an appropriate organometallic reagent $R_2M$ in the presence of a suitable catalyst or promoter gives compound g. Examples of suitable organometallic reagents and suitable catalysts/promoters include:

1. (substituted) alkyl grignard reagents $R_2MgX$ ($Fe(acac)_3$ promoter);
2. aryl, heteroaryl, or alkenyl boronic acids or esters (Pd $(PhP)_4$ catalyst); and
3. aryl or heteroaryl zinc reagents ($Pd(PhP)_4$ catalyst).

The $R_2$ groups thus installed may be further manipulated or reacted, using standard methods known to those skilled in the art (for example oxidation/reduction, hydrolysis, and the like), to provide further examples of the invention.

Reaction Scheme 2

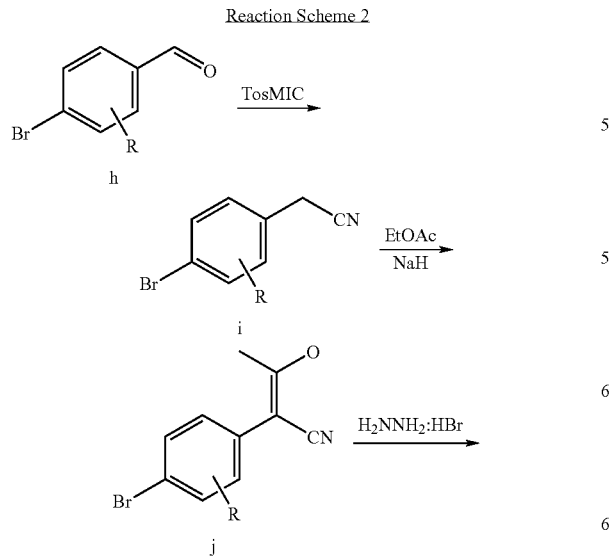

-continued

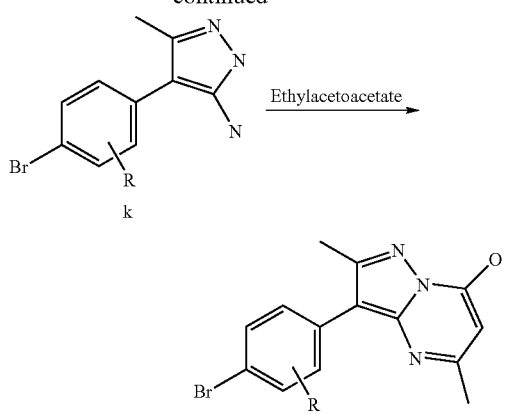

Multiple synthetic routes to the pyrazolopyrimidine core of the invention are available. In Reaction Scheme 2, the optionally substituted halobenzaldehyde h reacts with tosylmethyl isocyanide (TosMIC) to form the phenylacetonitrile i. Reaction of i with NaH and EtOAc gives the 3-hydroxy but-2-enenitrile j which undergoes ring closure in reaction with hydrazine HBr to give the 3-amino 2-phenyl pyrazole k. Addition of the β-keto ester gives the pyrazolo[1,5-a]pyrimidin-7-ol l. Substitution of the oxygen as in Reaction Scheme 1 and substitution of the distal bromine with Het gives compounds according to the invention.

Reaction Scheme 3

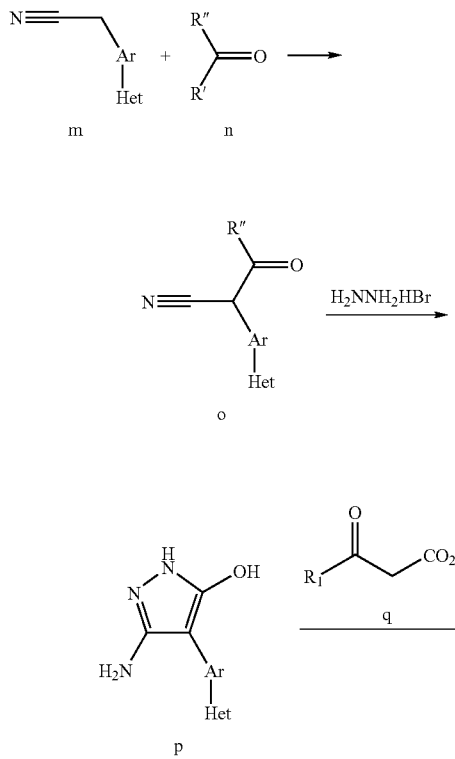

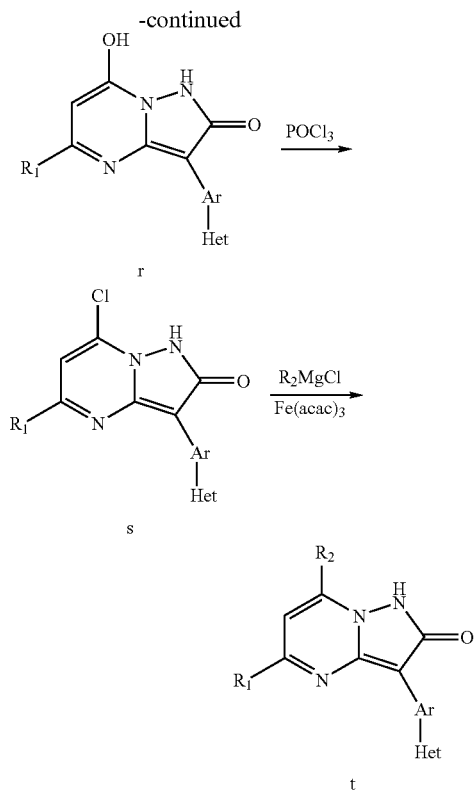

Reaction of substituted acetonitrile m with ketone n, where R' is a good leaving group such as alkoxy, cyano, or halo and where R" is a group such as hydroxy or alkoxy gives cyanoketone o which reacts with hydrazine to give substituted pyrazole p. Reaction of p with β-keto ester q gives pyrazolopyrimidine r. Reaction with $POCl_3$ gives the chloride s, and substitution of chloride by $R_2$ gives compound t.

The effectiveness of a compound as a CRF receptor antagonist may be determined by various assay methods. Suitable CRF antagonists of this invention may be capable of inhibiting the specific binding of CRF to its receptor and antagonizing activities associated with CRF. A compound of structure (1) may be assessed for activity as a CRF antagonist by one or more generally accepted assays for this purpose, including (but not limited to) the assays disclosed by DeSouza et al. (*J. Neuroscience* 7:88, 1987) and Battaglia et al. (*Synapse* 1:572, 1987). As mentioned above, suitable CRF antagonists include compounds which demonstrate CRF receptor affinity. CRF receptor affinity may be determined by binding studies that measure the ability of a compound to inhibit the binding of a radiolabeled CRF (e.g., [$^{125}I$]tyrosine-CFR) to its receptor (e.g., receptors prepared from rat cerebral cortex membranes). The radioligand binding assay described by DeSouza et al. (supra, 1987) provides an assay for determining a compound's affinity for the CRF receptor. Such activity is typically calculated from the $IC_{50}$ as the concentration of a compound necessary to displace 50% of the radiolabeled ligand from the receptor, and is reported as a "$K_i$" value calculated by the following equation:

$$K_i = \frac{IC_{50}}{1 + L/K_D}$$

where L=radioligand and $K_D$=affinity of radioligand for receptor (Cheng and Prusoff, *Biochem. Pharmacol.* 22:3099, 1973).

In addition to inhibiting CRF receptor binding, a compound's CRF receptor antagonist activity may be established by the ability of the compound to antagonize an activity associated with CRF. For example, CRF is known to stimulate various biochemical processes, including adenylate cyclase activity. Therefore, compounds may be evaluated as CRF antagonists by their ability to antagonize CRF-stimulated adenylate cyclase activity by, for example, measuring cAMP levels. The CRF-stimulated adenylate cyclase activity assay described by Battaglia et al. (supra, 1987) provides an assay for determining a compound's ability to antagonize CRF activity. Accordingly, CRF receptor antagonist activity may be determined by assay techniques which generally include an initial binding assay (such as disclosed by DeSouza (supra, 1987)) followed by a cAMP screening protocol (such as disclosed by Battaglia (supra, 1987)).

With reference to CRF receptor binding affinities, CRF receptor antagonists of this invention have a $K_i$ of less than 10 μM. In a preferred embodiment of this invention, a CRF receptor antagonist has a $K_i$ of less than 1 μM, and more preferably less than 0.25 μM (i.e., 250 nM). As set forth in greater detail below, the $K_i$ values may be assayed by the methods set forth in Example 27.

CRF receptor antagonists of the present invention may demonstrate activity at the CRF receptor site, and may be used as therapeutic agents for the treatment of a wide range of disorders or illnesses including endocrine, psychiatric, and neurological disorders or illnesses. More specifically, CRF receptor antagonists of the present invention may be useful in treating physiological conditions or disorders arising from the hypersecretion of CRF. Because CRF is believed to be a pivotal neurotransmitter that activates and coordinates the endocrine, behavioral and automatic responses to stress, CRF receptor antagonists of the present invention may be used to treat neuropsychiatric disorders. Neuropsychiatric disorders which may be treatable by CRF receptor antagonists of this invention include affective disorders such as depression; anxiety-related disorders such as generalized anxiety disorder, panic disorder, obsessive-compulsive disorder, abnormal aggression, cardiovascular abnormalities such as unstable angina and reactive hypertension; and feeding disorders such as anorexia nervosa, bulimia, and irritable bowel syndrome. CRF antagonists may also be useful in treating stress-induced immune suppression associated with various diseases states, as well as stroke. Other uses of CRF antagonists of this invention include treatment of inflammatory conditions (such as rheumatoid arthritis, uveitis, asthma, inflammatory bowel disease and G.I. motility), pain, Cushing's disease, infantile spasms, epilepsy and other seizures in both infants and adults, and various substance abuse and withdrawal (including alcoholism).

In another embodiment of the invention, pharmaceutical compositions containing one or more CRF receptor antagonists are disclosed. For the purposes of administration, the compounds of the present invention may be formulated as pharmaceutical compositions. Pharmaceutical compositions of the present invention comprise a CRF receptor antagonist of the present invention (i.e., a compound of structure (I)) and a pharmaceutically acceptable carrier and/or diluent. The CRF receptor antagonist is present in the composition in an amount which is effective to treat a particular disorder—that is, in an amount sufficient to achieve CRF receptor antagonist activity, and preferably with acceptable toxicity to the patient. Preferably, the pharmaceutical compositions of the present invention may include a CRF receptor antagonist in an amount from 0.1 mg to 250 mg per dosage depending upon the route of administration, and more preferably from 1 mg to 60 mg. Appropriate concentrations and dosages can be readily determined by one skilled in the art.

Pharmaceutically acceptable carrier and/or diluents are familiar to those skilled in the art. For compositions formulated as liquid solutions, acceptable carriers and/or diluents include saline and sterile water, and may optionally include antioxidants, buffers, bacteriostats and other common additives. The compositions can also be formulated as pills, capsules, granules, or tablets which contain, in addition to a CRF receptor antagonist, diluents, dispersing and surface active agents, binders, and lubricants. One skilled in this art may further formulate the CRF receptor antagonist in an appropriate manner, and in accordance with accepted practices, such as those disclosed in *Remington's Pharmaceutical Sciences*, Gennaro, Ed., Mack Publishing Co., Easton, Pa. 1990.

In addition, prodrugs are also included within the context of this invention. Prodrugs are any covalently bonded carriers that release a compound of structure (I) in vivo when such prodrug is administered to a patient. Prodrugs are generally prepared by modifying functional groups in a way such that the modification is cleaved, either by routine manipulation or in vivo, yielding the parent compound.

With regard to stereoisomers, the compounds of structure (I) may have chiral centers and may occur as racemates, racemic mixtures and as individual enantiomers or diastereomers. All such isomeric forms are included within the present invention, including mixtures thereof. Furthermore, some of the crystalline forms of the compounds of structure (I) may exist in alternative crystalline, amorphous or polymorphic forms as polymorphs, all of which are included in the present invention. In addition, some of the compounds of structure (I) may also form solvates with water or other organic solvents. Such solvates are similarly included within the scope of this invention.

In another embodiment, the present invention provides a method for treating a variety of disorders or illnesses, including endocrine, psychiatric and neurological disorders or illnesses. Such methods include administering of a compound of the present invention to a warm-blooded animal in an amount sufficient to treat the disorder or illness. Such methods include systemic administration of a CRF receptor antagonist of this invention, preferably in the form of a pharmaceutical composition. As used herein, systemic administration includes oral and parenteral methods of administration. For oral administration, suitable pharmaceutical compositions of CRF receptor antagonists include powders, granules, pills, tablets, and capsules as well as liquids, syrups, suspensions, and emulsions. These compositions may also include flavorants, preservatives, suspending, thickening and emulsifying agents, and other pharmaceutically acceptable additives. For parental administration, the compounds of the present invention may be prepared in aqueous injection solutions which may contain, in addition to the CRF receptor antagonist, buffers, antioxidants, bacteriostats, and other additives commonly employed in such solutions.

In another embodiment, the present invention permits the diagnostic visualization of specific sites within the body by the use of radioactive or non-radioactive pharmaceutical agents. Use of a compound of the present invention may provide a physiological, functional, or biological assessment of a patient or provide disease or pathology detection and assessment. Radioactive pharmaceuticals are employed in scintigraphy, positron emission tomography (PET), computerized tomography (CT), and single photon emission computerized tomography (SPECT.) For such applications, radioisotopes are incorporated of such elements as iodine (I) including $^{123}$I (PET), $^{125}$I (SPECT), and $^{131}$I, technetium (Tc) including $^{99}$Tc (PET), phosphorus (P) including $^{31}$P and $^{32}$P, chromium (Cr) including $^{51}$Cr, carbon (C) including $^{11}$C, fluorine (F) including $^{18}$F, thallium (Tl) including $^{201}$Tl, and like emitters of positron and ionizing radiation. Non-radioactive pharmaceuticals are employed in magnetic resonance imaging (MRI), fluoroscopy, and ultrasound. For such applications, isotopes are incorporated of such elements as gadolinium (Gd) including $^{153}$Gd, iron (Fe), barium (Ba), manganese (Mn), and thallium (Tl). Such entities are also useful for identifying the presence of particular target sites in a mixture and for labeling molecules in a mixture.

As mentioned above, administration of a compound of the present invention can be used to treat a wide variety of disorders or illnesses. In particular, compounds of the present invention may be administered to a warm-blooded animal for the treatment of depression, anxiety disorder, panic disorder, obsessive-compulsive disorder, abnormal aggression, unstable angina, reactive hypertension, anorexia nervosa, bulimia, irritable bowel syndrome, stress-induced immune suppression, stroke, inflammation, pain, Cushing's disease, infantile spasms, epilepsy, and substance abuse or withdrawal.

The following examples are provided for purposes of illustration, not limitation.

EXAMPLES

The CRF receptor antagonists of this invention may be prepared by the methods disclosed in Examples 1 to 26. Example 27 presents a method for determining the receptor binding affinity, and Example 28 discloses an assay for screening compounds of this invention for CRF-stimulated adenylate cyclase activity.

Analytical HPLC-MS Method 1

Platform: Agilent 1100 series: equipped with an auto-sampler, an UV detector (220 nM and 254 nM), a MS detector (APCI);

HPLC column: YMC ODS AQ, S-5, 5μ, 2.0×50 mm cartridge;

HPLC gradient: 1.0 mL/minute, from 10% acetonitrile in water to 90% acetonitrile in water in 2.5 minutes, maintaining 90% for 1 minute. Both acetonitrile and water have 0.025% TFA.

Analytical HPLC-MS Method 2

Platform: Agilent 1100 series: equipped with an auto-sampler, an UV detector (220 nM and 254 nM), a MS detector (APCI);

HPLC column: Phenomenex Synergi-Max RP, 2.0×50 mm column;

HPLC gradient: 1.0 mL/minute, from 5% acetonitrile in water to 95% acetonitrile in water in 13.5 minutes, maintaining 95% for 2 minute. Both acetonitrile and water have 0.025% TFA.

Analytical HPLC-MS Method 3

Platform: Agilent 1100 series: equipped with an auto-sampler, an UV detector (220 nM and 254 nM), a MS detector (electrospray);

HPLC column: XTerra MS, $C_{18}$, 5μ, 3.0×250 mm column;

HPLC gradient: 1.0 mL/minute, from 10% acetonitrile in water to 90% acetonitrile in water in 46 minutes, jump to 99% acetonitrile and maintain 99% acetonitrile for 8.04 minutes: Both acetonitrile and water have 0.025% TFA.

Analytical HPLC-MS Method 4

Platform: Agilent 1100 series: equipped with an auto-sampler, an UV detector (220 nM and 254 nM), a MS detector (APCI) and Berger FCM 1200 $CO_2$ pump module;

HPLC column: Berger Pyridine, PYR 60A, 6μ, 4.6×150 mm column;

HPLC gradient: 4.0 mL/minute, 120 bar; from 10% methanol in supercritical $CO_2$ to 60% methanol in supercritical $CO_2$ in 1.67 minutes, maintaining 60% for 1 minute. Methanol has 1.5% water. Backpressure regulated at 140 bar.

Preparative HPLC-MS

Platform: Shimadzu HPLC equipped with a Gilson 215 auto-sampler/fraction collector, UV detector and a PE Sciez API150EX mass detector;

HPLC column: BHK ODS-O/B, 5μ, 30×75 mm

HPLC gradient: 35 mL/minute, 10% acetonitrile in water to 100% acetonitrile in 7 minutes, maintaining 100% acetonitrile for 3 minutes, with 0.025% TFA.

Abbreviations:
AA: Acetyl acetate
LAH: Lithium aluminum hydride
DCM: Dichloromethane
DMSO: Dimethyl sulfoxide
EM: Ethyl acetoacetate
LC-MS: liquid chromatography-mass spectroscopy
$NaBH(OAc)_3$: Sodium Triacetoxyborohydride
Pd—C: Palladium (10%) on Carbon
TFA: Trifluoroacetic acid
Tosmic: Tosylmethyl isocyanide
acac: acetylacetonate
EDCl: N-ethyl-N'-(dimethylaminopropyl)carbodiimide hydrochloride
THF: tetrahydrofuran
TEA: triethylamine
$t_R$: Retention time Example 1

7-(2-Methoxy-phenyl)-3-(2-methoxy-4-pyrazol-1-yl-phenyl)-2,5-dimethyl-pyrazolo[1,5-a]pyrimidine

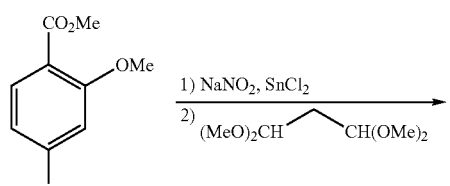

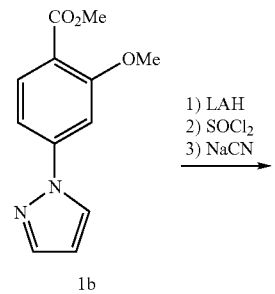

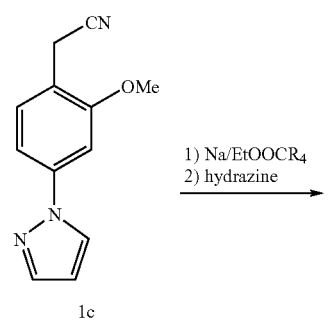

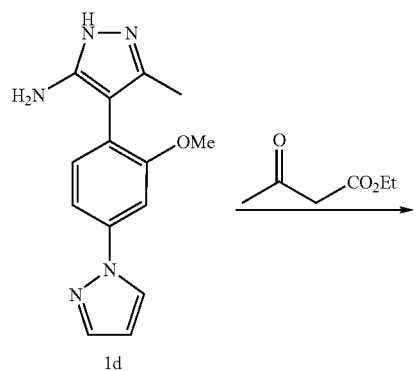

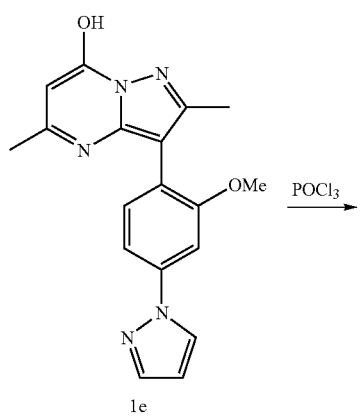

-continued

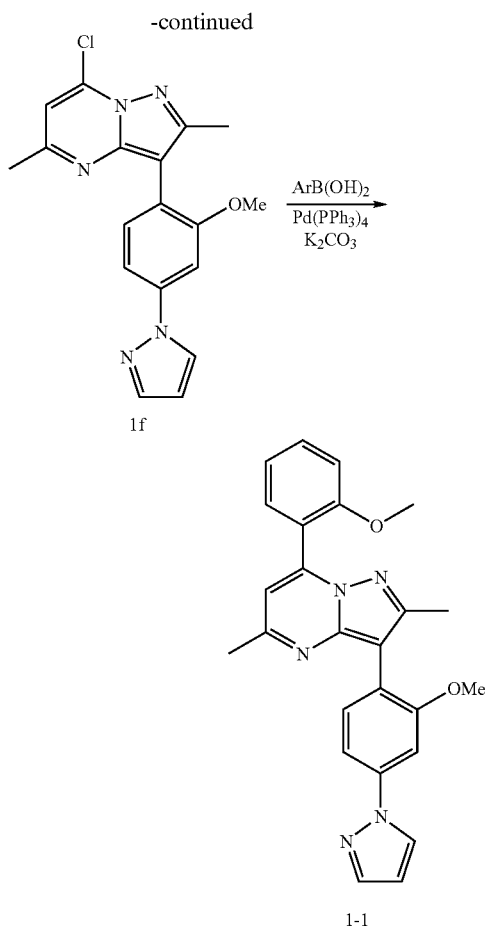

Step 1A:

To a cooled suspension of methyl 4-amino-2-methoxybenzoate (6.82 g, 37.7 mmol) in 6N HCl (aqueous) was added a solution of sodium nitrite (2.60 g, 37.7 mmol) dropwise. After stirring at 0° C. for 20 min, stannous chloride dihydrate (24.7 g, 109.3 mmol) was added portionwise. The resulting suspension was stirred at 0° C. for 1.5 hr prior to filtration. The collected solid was suspended in EtOH to which malonaldehyde bis(dimethyl acetal) (7.5 mL, 45.7 mmol) was added, and this reaction mixture was subjected to reflux overnight. After evaporation of EtOH, the residue was extracted between EtOAc and water, and the organic phase was dried and evaporated to dryness. The residue was passed through a silica gel plug (25% EtOAc/hexane) to yield Cmpd 1b (7.43 g) as a mixture of the methyl and ethyl benzoate.

Step 1B:

To a solution of 1b (10.6 g) in dry diethyl ether (200 mL) was added LAH powder (1.74 g) slowly at 0° C. After stirring for 45 min at 0° C. the reaction mixture was decanted onto ice-water, and the aqueous phase was acidified to pH 4.0. After isolation, the alcohol (8.8 g) was refluxed with thionyl chloride (10 mL) in DCM for 2.5 hr, decanted onto ice-water, and extracted with DCM. The crude benzyl chloride (8.26 g) was heated with NaCN (3.65 g, 74.4 mmol) in DMSO (100 mL) at 80° C. for 45 min. After removal of DMSO, Cmpd 1c (5.98 g) obtained after column chromatography with 30% EtOAc/hexane.

Step 1C:

To a solution of 1c (5.98 g, 28.1 mmol) in EtOAc (150 mL) was added metallic sodium (1.0 g, 43.5 mmol) portionwise, and the mixture was refluxed overnight. The resulting suspension was decanted onto ice-water and acidified to pH 4.0. The organic phase was dried and evaporated to dryness. The resulting compound (9.5 g) was mixed with hydrazine monohydrobromide (15.3 g, 135.4 mmol,) and refluxed in EtOH/H$_2$O (6:1) for 5 hr. After evaporation of EtOH and extraction with EtOAc, the organic phase was dried and evaporated to dryness to yield Cmpd 1d (7.5 g.)

Step 1D:

A mixture of 1d (7.5 g, 27.9 mmol) was refluxed with ethyl acetoacetate (5.0 mL) in AcOH (100 mL) for 3 hr. After evaporation of AcOH and precipitation in diethyl ether, Cmpd 1e (10.4 g) obtained after filtration.

Step 1E:

To a suspension of 1e (2.1 g, 6.3 mmol) in acetonitrile was added POCl$_3$ (2.2 mL, 24.1 mmol,) and this mixture was refluxed for 5 hr, decanted to ice-water, and extracted with EtOAc to yield Cmpd 1f (1.88 g) after chromatographic purification.

Step 1F:

A mixture of Cmpd 1f (1.0 mmol), 2-methoxyphenylboronic acid (1.2 mmol), K$_2$CO$_3$ (2.0 mmol) and Pd(PPh$_3$)$_4$ (0.05 mmol) was heated in 1,4-dioxane/H$_2$O (2:1) at 110° C. overnight. After evaporation of solvent, the mixture was extracted between CHCl$_3$/H$_2$O, and the organic phase was dried and evaporated to dryness. Cmpd 1-1 (402 mg) was obtained after column chromatography. Depending on the aryl functionality in the arylboronic acid reagent, the compounds listed in the following table were synthesized and purified by preparative LC-MS:

| Cmpd | R$_2$ | MW | MS | t$_R$ | HPLC Method |
|---|---|---|---|---|---|
| 1-1 | 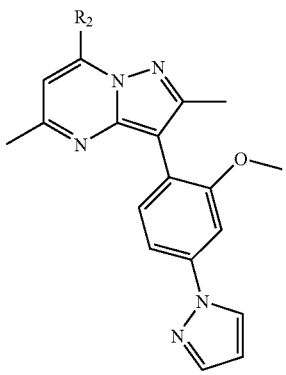 | 425.49 | 425 | 1.315 | 4 |

-continued
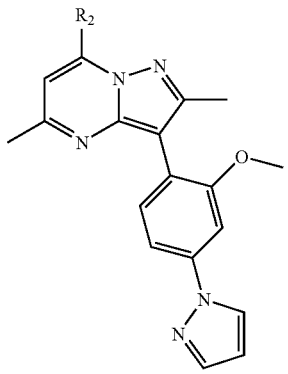
| Cmpd | R₂ | MW | MS | t_R | HPLC Method |
|---|---|---|---|---|---|
| 1-2 | 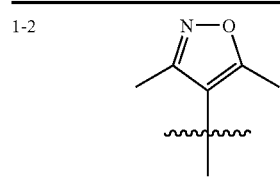 | 414.47 | 414 | 1.586 | 4 |
| 1-3 | 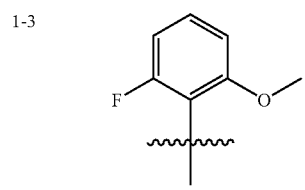 | 443.48 | 443 | 1.335 | 4 |
| 1-4 | 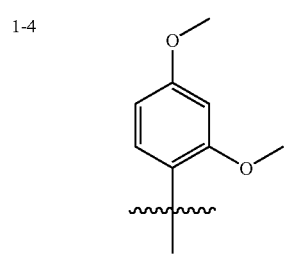 | 455.52 | 455 | 1.32 | 4 |
| 1-5 | 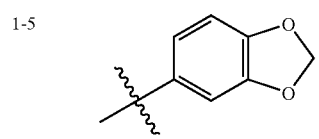 | 439.47 | 439 | 1.353 | 4 |
| 1-6 | 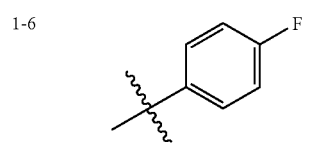 | 413.45 | 413 | 1.25 | 4 |
| 1-7 | 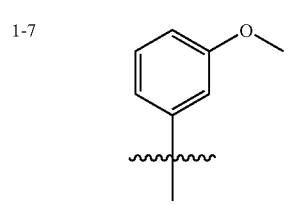 | 425.49 | 425 | 1.317 | 4 |
-continued
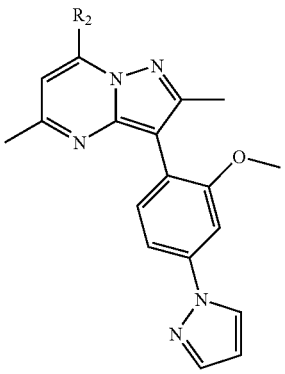
| Cmpd | R₂ | MW | MS | t_R | HPLC Method |
|---|---|---|---|---|---|
| 1-8 | 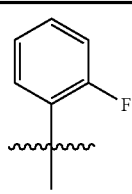 | 413.45 | 413 | 1.236 | 4 |
| 1-9 | | 439.47 | 439 | 5.625 | 2 |
| 1-10 | | 457.49 | 457 | 7.09 | 2 |
| 1-11 | | 443.48 | 443 | 1.226 | 4 |
| 1-12 | | 459.94 | 459 | 1.188 | 4 |
| 1-13 | | 473.56 | 473 | 1.446 | 4 |

-continued
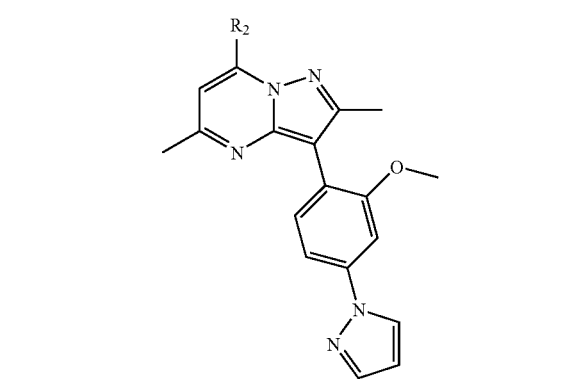
| Cmpd | R₂ | MW | MS | $t_R$ | HPLC Method |
|---|---|---|---|---|---|
| 1-14 | (F, OMe phenyl) | 443.48 | 443 | 1.120 | 4 |
| 1-15 | (2-F pyridyl) | 414.44 | 414 | 1.242 | 4 |
| 1-16 | (o-tolyl) | 409.49 | 409 | 1.088 | 4 |
| 1-17 | (2,5-diF phenyl) | 431.44 | 431 | 1.071 | 4 |
| 1-18 | (4-methylsulfonylphenyl) | 473.56 | 473 | 1.514 | 4 |
| 1-19 | (2-CF₃ phenyl) | 463.46 | 463 | 1.030 | 4 |
-continued
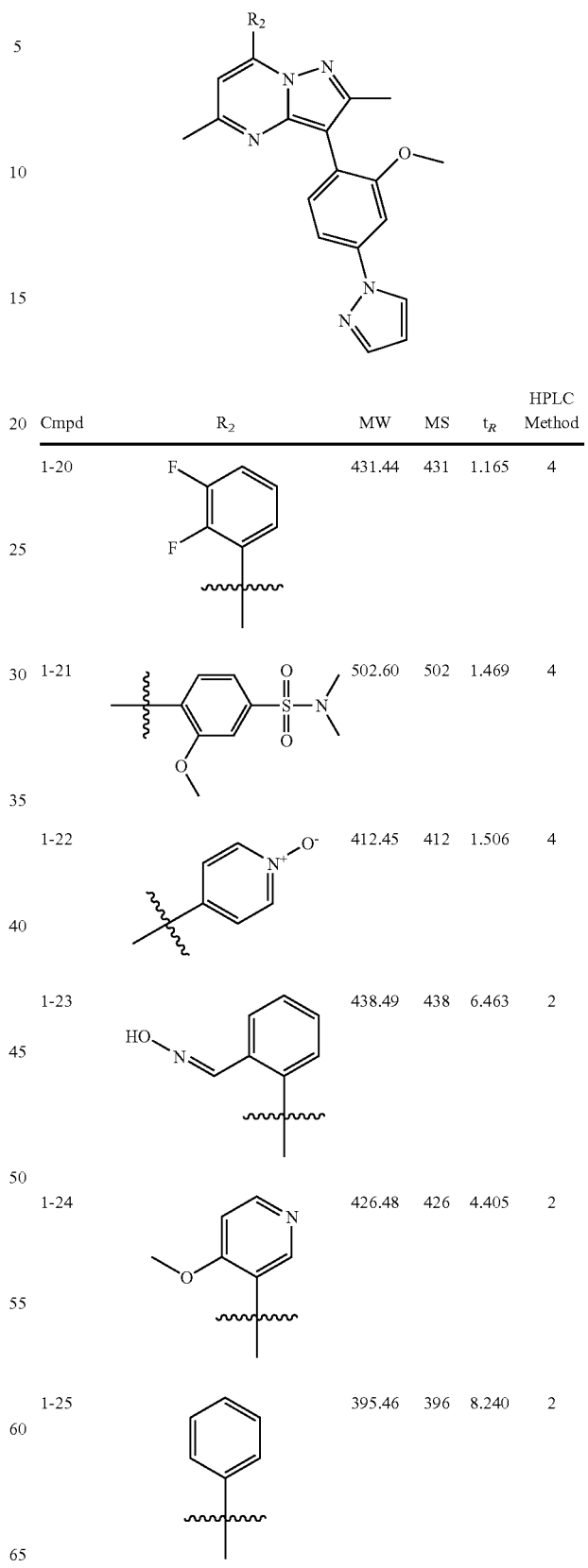
| Cmpd | R₂ | MW | MS | $t_R$ | HPLC Method |
|---|---|---|---|---|---|
| 1-20 | (2,3-diF phenyl) | 431.44 | 431 | 1.165 | 4 |
| 1-21 | (sulfonamide methoxyphenyl) | 502.60 | 502 | 1.469 | 4 |
| 1-22 | (pyridine N-oxide) | 412.45 | 412 | 1.506 | 4 |
| 1-23 | (oxime phenyl) | 438.49 | 438 | 6.463 | 2 |
| 1-24 | (methoxy pyridyl) | 426.48 | 426 | 4.405 | 2 |
| 1-25 | (phenyl) | 395.46 | 396 | 8.240 | 2 |

-continued
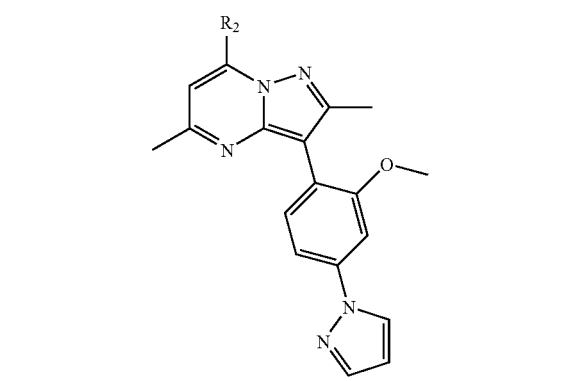
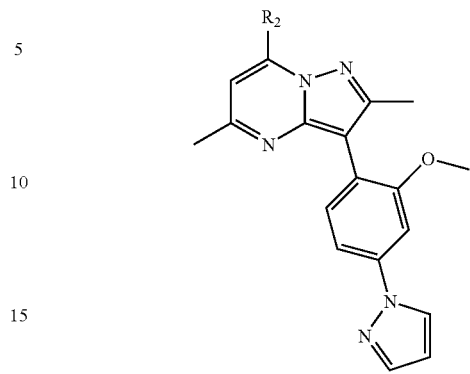
| Cmpd | R₂ | MW | MS | $t_R$ | HPLC Method |
|---|---|---|---|---|---|
| 1-26 | 4-methoxyphenyl | 425.59 | 425.9 | 8.260 | 2 |
| 1-27 | 2,6-dimethoxyphenyl | 455.52 | 456 | 7.550 | 2 |
| 1-28 | 2-thienyl | 401.49 | 401.9 | 8.490 | 2 |
| 1-29 | 3-thienyl | 401.49 | 401.9 | 8.530 | 2 |
| 1-30 | 2-furyl | 385.42 | 385.9 | 8.410 | 2 |
| 1-31 | 5-methyl-2-furyl | 399.45 | 335.9 | 4.700 | 2 |
| 1-32 | 3-furyl | 385.42 | 385.9 | 8.300 | 2 |
| 1-33 | 4-acetylphenyl | 437.50 | 437 | 7.861 | 2 |
| 1-34 | 2-chlorophenyl | 429.912 | 429 | 8.229 | 2 |
| 1-35 | 4-methoxy-3-methylphenyl | 439.512 | 439 | 8.320 | 2 |
| 1-36 | 3,4-dimethoxyphenyl | 455.52 | 455 | 7.718 | 2 |
| 1-37 | 4-carbamoylphenyl | 438.49 | 438 | 6.153 | 2 |

-continued
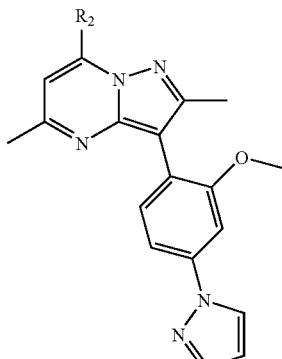
| Cmpd | R$_2$ | MW | MS | t$_R$ | HPLC Method |
|---|---|---|---|---|---|
| 1-38 | 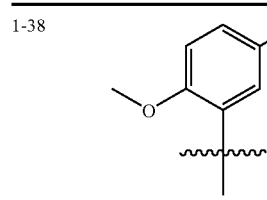 | 443.48 | 443 | 1.218 | 4 |
| 1-39 | 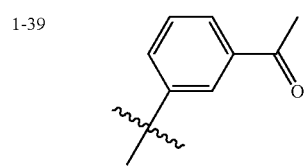 | 437.50 | 437 | 7.807 | 2 |
| 1-40 | 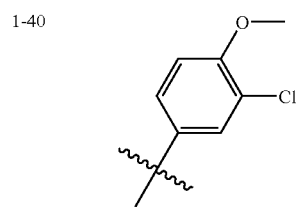 | 459.94 | 459 | 8.956 | 2 |
| 1-41 | 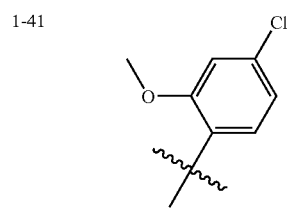 | 459.94 | 459 | 8.598 | 2 |
| 1-42 | 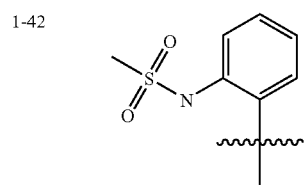 | 488.57 | 488 | 7.216 | 2 |
| 1-43 | 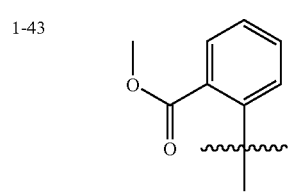 | 453.50 | 454 | 7.601 | 2 |
-continued
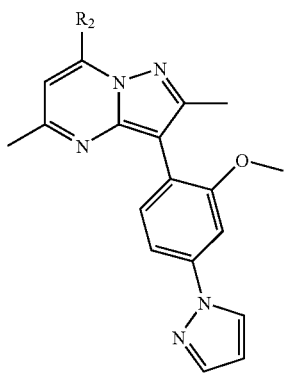
| Cmpd | R$_2$ | MW | MS | t$_R$ | HPLC Method |
|---|---|---|---|---|---|
| 1-44 | 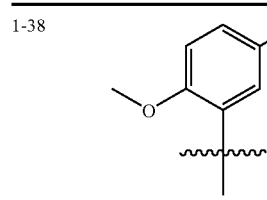 | 453.50 | 454 | 8.310 | 2 |
| 1-45 | 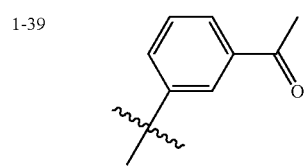 | 453.50 | 454 | 8.380 | 2 |
| 1-46 | 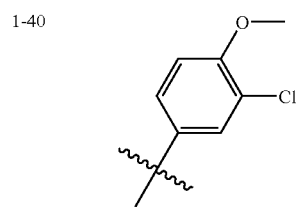 | 466.54 | 467 | 6.690 | 2 |
| 1-47 | 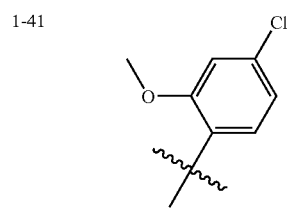 | 439.47 | 440 | 7.010 | 2 |
| 1-48 | 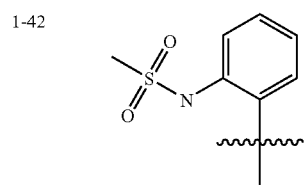 | 485.54 | 486 | 8.000 | 2 |

-continued
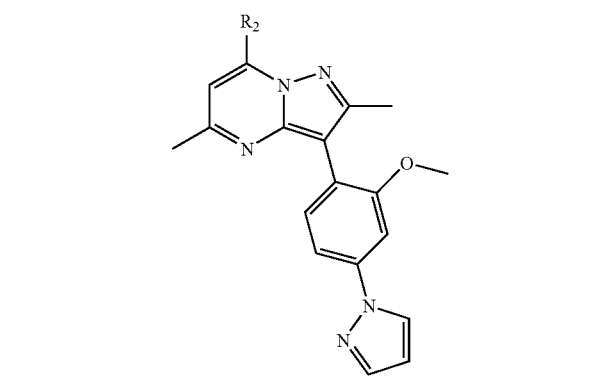
| Cmpd | R₂ | MW | MS | t_R | HPLC Method |
|---|---|---|---|---|---|
| 1-49 | pyrimidin-5-yl | 397.44 | 398 | 6.270 | 2 |
| 1-50 | 4-ethoxyphenyl | 439.52 | 439 | 8.288 | 2 |
| 1-51 | 3-fluoropyridin-4-yl | 414.44 | 414 | 5.640 | 2 |
| 1-52 | 5-methoxypyridin-3-yl | 426.48 | 426 | 5.910 | 2 |
| 1-53 | pyridin-4-yl | 396.45 | 396 | 4.920 | 2 |
-continued
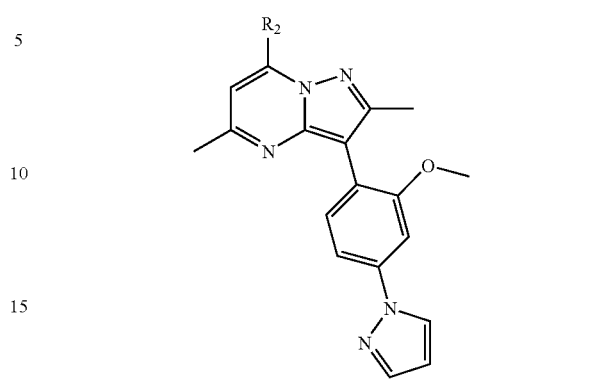
| Cmpd | R₂ | MW | MS | t_R | HPLC Method |
|---|---|---|---|---|---|
| 1-54 | 6-methoxypyridin-3-yl | 426.48 | 426 | 6.630 | 2 |
| 1-55 | 4-(2-carboxyethyl)phenyl | 467.53 | 468 | 6.970 | 2 |
| 1-56 | 4-carboxyphenyl | 439.47 | 440 | 6.710 | 2 |
| 1-57 | 3,5-difluorophenyl | 431.44 | 432 | 8.660 | 2 |

-continued
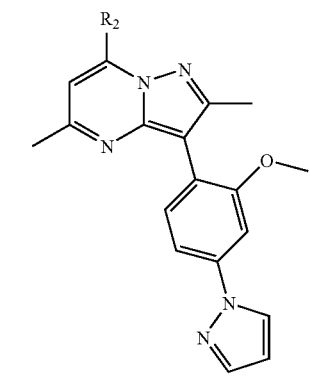
| Cmpd | R₂ | MW | MS | $t_R$ | HPLC Method |
|---|---|---|---|---|---|
| 1-58[1] | (1H-pyrrol-3-yl) | 384.44 | 385 | 5.390 | 2 |
| 1-59 | (4-((dimethylamino)methyl)phenyl) | 452.56 | 453 | 4.590 | 2 |
| 1-60 | (2,3-dimethoxyphenyl) | 455.52 | 455 | 6.170 | 2 |
| 1-61 | (4-cyanophenyl) | 420.47 | 420 | 1.410 | 4 |
-continued
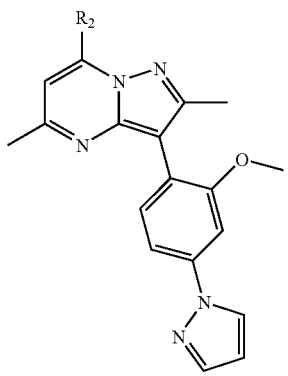
| Cmpd | R₂ | MW | MS | $t_R$ | HPLC Method |
|---|---|---|---|---|---|
| 1-62 | (2,3,4-trimethoxyphenyl) | 485.54 | 486 | 7.540 | 2 |
| 1-63 | (2,6-dimethoxypyridin-3-yl) | 456.50 | 456 | 8.120 | 2 |
| 1-64 | (3-formyl-4-methoxyphenyl... isomer) | 453.50 | 454.3 | 5.710 | 2 |
| 1-65 | (4-methylthiophen-2-yl) | 415.52 | 415 | 6.770 | 2 |
| 1-66 | (1-methyl-1H-pyrazol-4-yl) | 399.46 | 399 | 6.430 | 2 |

-continued
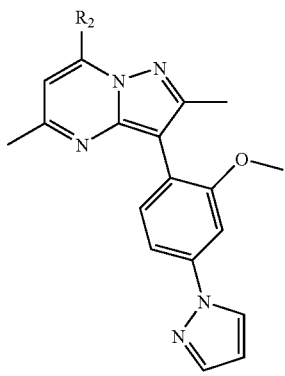
| Cmpd | R₂ | MW | MS | $t_R$ | HPLC Method |
|---|---|---|---|---|---|
| 1-67 | 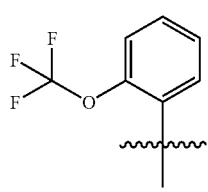 | 479.46 | 479 | 6.740 | 2 |
| 1-68 | 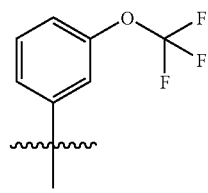 | 479.46 | 479 | 7.260 | 2 |
| 1-69 | 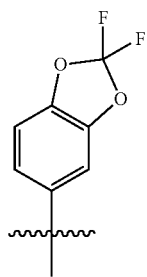 | 475.45 | 475 | 6.970 | 2 |
| 1-70 | 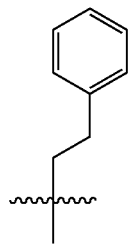 | 423.52 | 423 | 6.370 | 2 |
-continued
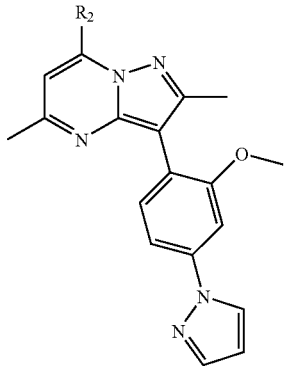
| Cmpd | R₂ | MW | MS | $t_R$ | HPLC Method |
|---|---|---|---|---|---|
| 1-71 | 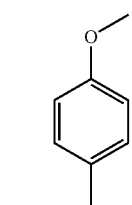 | 453.54 | 453 | 6.280 | 2 |
| 1-72 | 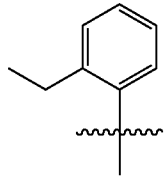 | 423.52 | 423 | 8.420 | 2 |
| 1-73 | | 415.52 | 415 | 8.080 | 2 |
Example 1A
Alternate Synthesis of Intermediate 1f
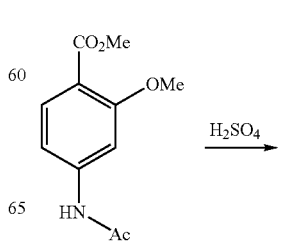 $\xrightarrow{H_2SO_4}$ -continued

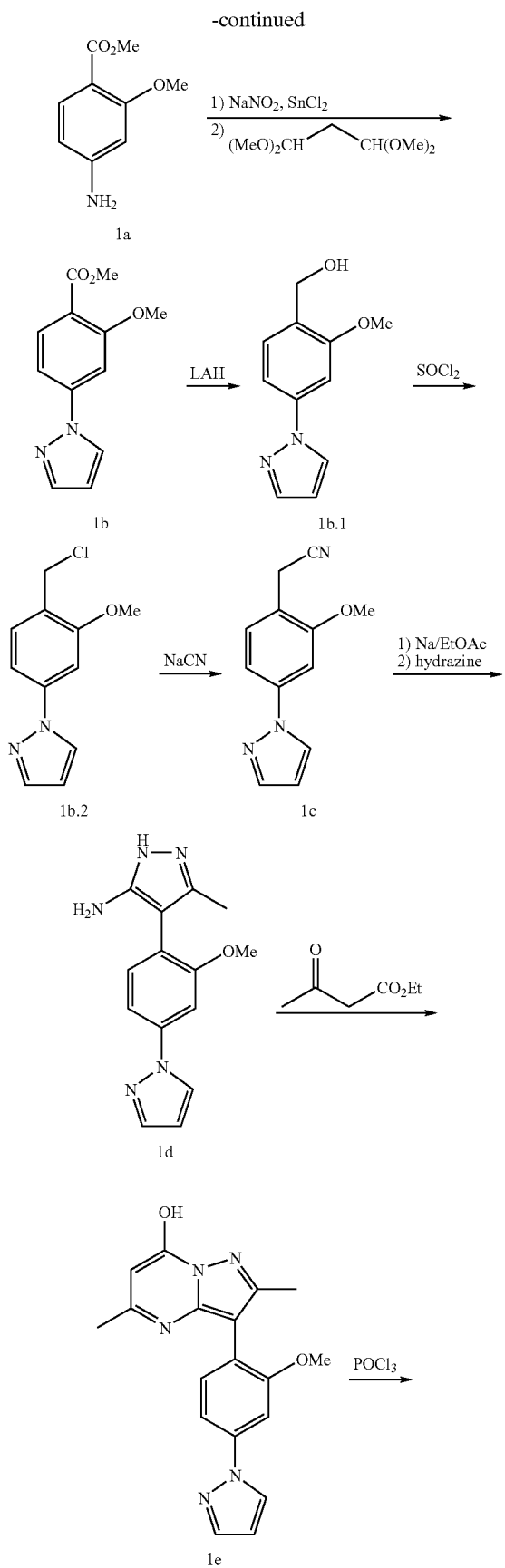

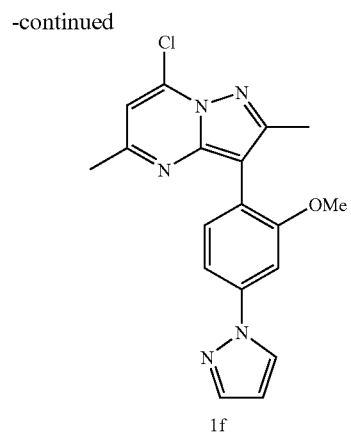

Step 1A-A:

To a 3-neck flask equipped with a mechanical stirrer was charged 250 g (1.12 mol) of 2-methoxy-4-acetylaminobenzoic acid methyl ester followed by 1 L of methanol. Agitation was started and 94 mL (3.36 mmol, 3 eq.) of concentrated sulfuric acid was slowly added creating a slight reflux. The mixture was stirred for 24 hr. The mixture was concentrated in vacuo affording a thick slurry. The slurry was filtered using a Buchner funnel and washed with 300 mL of cold methanol. The filter cake was collected and dried in vacuo at 45° C. for 24 hr affording 302 g of 1a as a hemi-sulfate salt in a 96% yield.

Step 1A-B:

In a 2 L three-neck Morton flask equipped with a mechanical stirrer and thermocouple was charged 200 g (716 mmol) of methyl 4-amino-2-methoxybenzoate 1a. The solid was slurried with 700 mL of 6N hydrochloric acid and chilled in an ice-bath. To the mixture was charged dropwise 54.3 g (788 mmol, 1.1 eq.) of sodium nitrite in 100 mL of water maintaining a temperature of <15° C. during the addition. The mixture was stirred an additional 1.5 hr affording a light yellow, homogeneous solution. To the mixture was carefully added 272 g (1432 mmol, 2 eq.) of anhydrous stannous chloride. The temperature during the addition was kept <10° C. The mixture was stirred at 0° C. for 1 hr, and then stored at 5° C. for 16 hr. The precipitate was collected by filtration through a Buchner funnel and the filter cake air dried for 2 hr. The filter cake was transferred to a 2 L round bottom flask equipped with a magnetic stir bar and diluted with 600 mL of ethanol. To the slurry was charged 142 mL (859 mmol, 1.2 eq.) of malonaldehyde bis(dimethyl acetal) and the mixture refluxed for 6 hr. After evaporation of ethanol, the residue was diluted with ethyl acetate and neutralized with sodium hydroxide. The organic phase was separated, dried and concentrated in vacuo. The crude product was passed through a silica gel plug eluting with 25% ethyl acetate in hexane affording 96 g of Cmpd 1b in a 58% yield as a mixture of the methyl and ethyl esters.

Step 1A-C:

To a 1 L round bottom flask containing 500 mL dry THF was added LAH (14.5 g, 380 mmol, 0.95 eq), and the mixture was cooled to 0° C. To this mixture was added dropwise a solution of 1b (96 g, 400 mmol, 1.0 eq) in 300 mL THF. The temperature was maintained below 15° C. during the addition. After the addition was complete, the mixture was stirred for 1 hr, then the reaction mix was carefully quenched with water (14.5 mL), 10% aq. sodium hydroxide (14.5 mL), and water (43.5 mL). The resulting mixture was filtered through a pad of Celite® and concentrated to provide 1b.1 as a slightly yellow oil (63.9 g, 75.7%), which was used without further purification.

Step 1A-D:

Thionyl chloride (95 mL, 1.30 mol, 3.1 eq) was added dropwise over 1 hr to a solution of 1b.1 (85.0 g, 0.42 mol) in 400 mL DCM, keeping the rate of addition such that a gentle reflux was maintained. A precipitate formed, which re-dissolved upon completion of the addition. The resulting dark solution was refluxed for 4 hr. The cooled reaction mixture was poured onto 500 g of ice, and the resulting mixture was extracted with 2×700 mL of DCM. The combined organic layers were washed with saturated aqueous sodium bicarbonate, dried over sodium sulfate, filtered, and concentrated to provide 1b.2 (76.5 g) as a brown solid, which was used without further purification.

Step 1A-E:

A solution of 1b.2 (76 g, 340 mmol, 1.0 eq.) in DMF (100 mL) was added dropwise over 20 min. to a mixture of sodium cyanide (24.5 g, 500 mmol, 1.5 eq) and DMF (300 mL) heated to 100° C. The mixture was heated at 100° C. for 4 hr, then the cooled mixture was filtered through Celite®. The filtrate was concentrated, then the residue was taken up in 300 mL DCM and washed with saturated aqueous sodium bicarbonate solution (200 mL). The organic layer was dried over sodium sulfate, filtered, and concentrated to provide a dark brown solid residue. This residue was slurried in ethanol (100 mL), then the solid was collected by filtration and washed with cold ethanol and ether, providing 1c (48.0 g) as an off-white solid. The mother liquid was concentrated and purified by silica gel chromatography, eluting with 1:1 hexane/ethyl acetate, to provide an additional 15.4 g of 1c as a white solid. Combined yield 63.4 g.

Step 1A-F:

To a solution of 1c (63.4 g, 0.30 mol, 1 eq) in ethyl acetate (800 mL) was added metallic sodium (10.3 g, 0.45 mmol, 1.5 eq) portionwise, and the mixture was refluxed for 16 hr The cooled suspension was poured onto 500 g ice, acidified to pH 5, then extracted with 2×300 mL ethyl acetate. The organic phase was dried over sodium sulfate, filtered, and concentrated to a crude yellow oil (86.5 g).

The crude yellow oil (86.5 g) was dissolved in ethanol (480 mL) and water (80 mL), then hydrazine monohydrobromide (100 g, 0.88 mol, 3 eq) was added and the mixture was heated at 85° C. for 16 hr. The solvents were evaporated, brine (200 mL) was added, and the mixture was extracted with 2×300 mL ethyl acetate. The combined organic layers were dried over sodium sulfate, filtered, and concentrated to provide 1d (68 g) as a crude brown foam, which was used without further purification.

Step 1A-G:

A mixture of 1d (68 g, 250 mmol, 1.0 eq), ethyl acetoacetate (100 mL), acetic acid (150 mL), and ethanol (150 mL) was refluxed for 24 hr. The cooled mixture was concentrated to provide a solid residue, which was then deposited onto a fritted glass filter and washed with ether, providing 1e (52.0 g, 51.2%) as an off-white solid. The mother liquor was concentrated, then chromatographed on silica gel using 10% methanol in DCM as eluent. The solid product thus obtained was washed with ether to provide an additional 17.0 g of 1e as an off-white solid (combined yield 69 g).

Step 1A-H:

To a suspension of 1e (41.2 g, 123 mmol) in acetonitrile (200 mL) was added POCl$_3$ (45.0 mL, 493 mmol,) and this mixture was refluxed for 16 hr. The cooled reaction mixture was poured onto ice-water, and the resulting mixture was extracted with chloroform. The combined organic extracts were dried over sodium sulfate, filtered, and concentrated. The residue was purified by silica gel chromatography, eluting with 3:1 hexanes/ethyl acetate, to yield 1f (29.0 g) as a tan solid.

Example 2

7-Isopropyl-3-(2-methoxy-4-pyrazol-1-yl-phenyl)-2,5-dimethyl-pyrazolo[1,5-a]pyrimidine

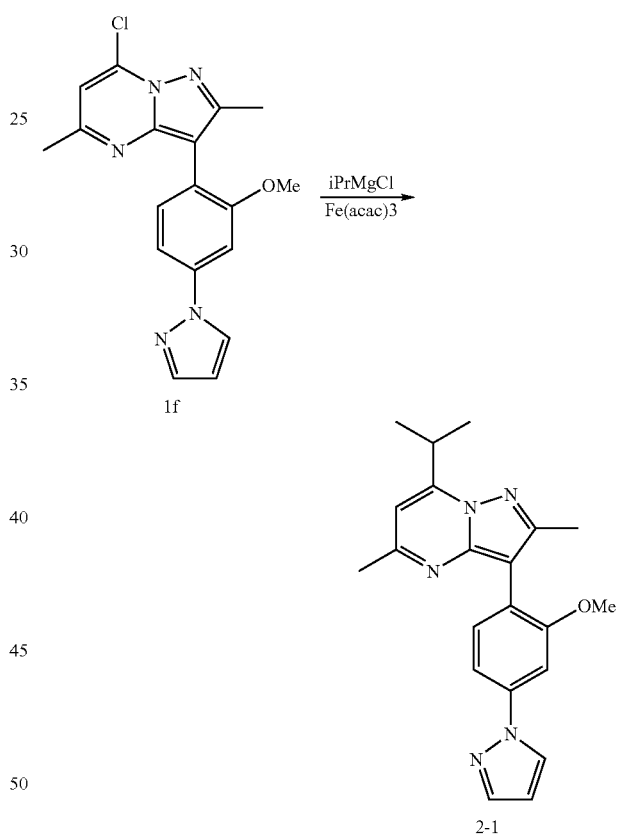

Step 2A:

To a solution of Cmpd 1f (1.41 g, 4.0 mmol) and Fe(acac)$_3$ (424 mg, 1.2 mmol) in THF/NMP (v/v=8:1) was added iPrMgCl (2.0 M in THF, 4.0 mL) slowly at room temperature. The reaction mixture was stirred for 1.5 hr before quenched with 1N HCl (aq.). After extraction with EtOAc, the crude product was purified by column chromatography (25% EtOAc/Hexane) to yield Cmpd 2-1 (628 mg.)

Depending on the alkyl functionality in the alkyl magnesium halide, the compounds listed in the following table were synthesized:

| Cmpd | R₂ | MW | MS | t_R | HPLC Method |
|---|---|---|---|---|---|
| 2-1 | isopropyl | 361.447 | 361 | 1.286 | 4 |
| 2-2 | isobutyl | 375.474 | 375 | 1.499 | 4 |
| 2-3 | CH₃ | 333.393 | 333 | 1.542 | 4 |
| 2-4 | sec-butyl | 375.474 | 375 | 1.278 | 4 |
| 2-5 | neopentyl | 389.5 | 390.2 | 8.490 | 2 |
| 2-6 | ethyl | 347.42 | 348 | 6.514 | 2 |
| 2-7 | CF₃-propyl | 415.417 | 415 | 7.880 | 2 |
| 2-8 | benzyl | 409.491 | 409 | 6.280 | 2 |
| 2-9 | 3-F-benzyl | 427.481 | 428 | 8.240 | 2 |
| 2-10 | 4-Cl-benzyl | 443.936 | 444 | 8.790 | 2 |
| 2-11 | 2-Cl-6-F-benzyl | 461.926 | 462 | 8.740 | 2 |
| 2-12 | 2-F-benzyl | 427.481 | 428 | 8.240 | 2 |

-continued
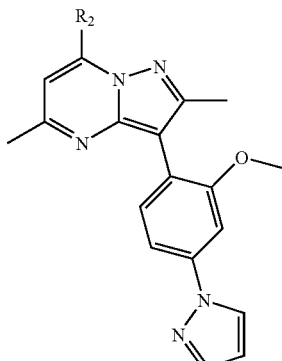
| Cmpd | R₂ | MW | MS | $t_R$ | HPLC Method |
|---|---|---|---|---|---|
| 2-13 | 3-Cl-benzyl | 443.936 | 444 | 8.750 | 2 |
| 2-14 | 2-Cl-benzyl | 443.936 | 444 | 8.660 | 2 |
| 2-15 | 4-F-benzyl | 427.481 | 428 | 8.240 | 2 |
-continued
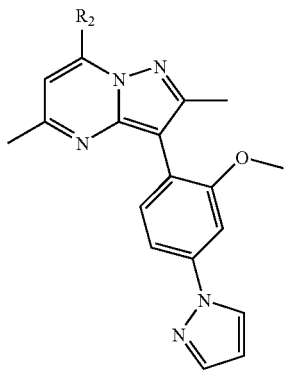
| Cmpd | R₂ | MW | MS | $t_R$ | HPLC Method |
|---|---|---|---|---|---|
| 2-16 | tert-butyl | 361.447 | 361 | 2.700 | 1 |
| 2-17 | 3-Br-benzyl | 488.387 | 488 | 8.920 | 2 |
Example 3
3-(2-Methoxy-4-pyrazol-1-yl-phenyl)-2,5-dimethyl-pyrazolo[1,5-a]pyrimidine-7-carboxylic Acid Ethyl Ester
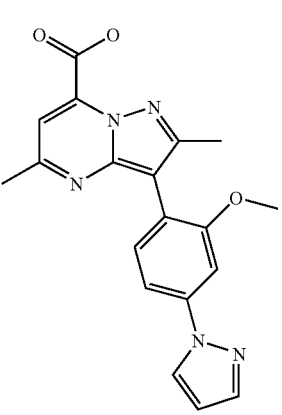
3-9
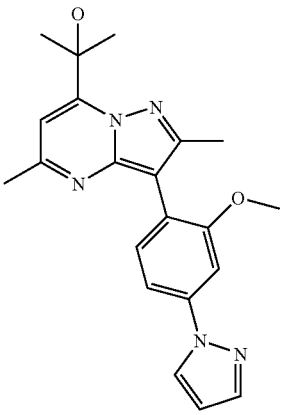
3-5
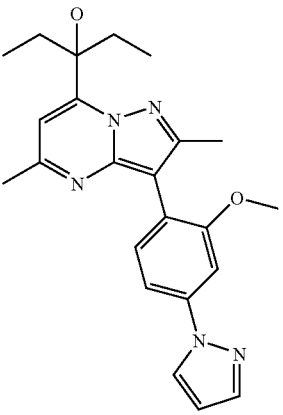
3-6
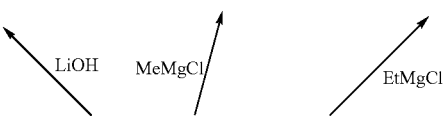

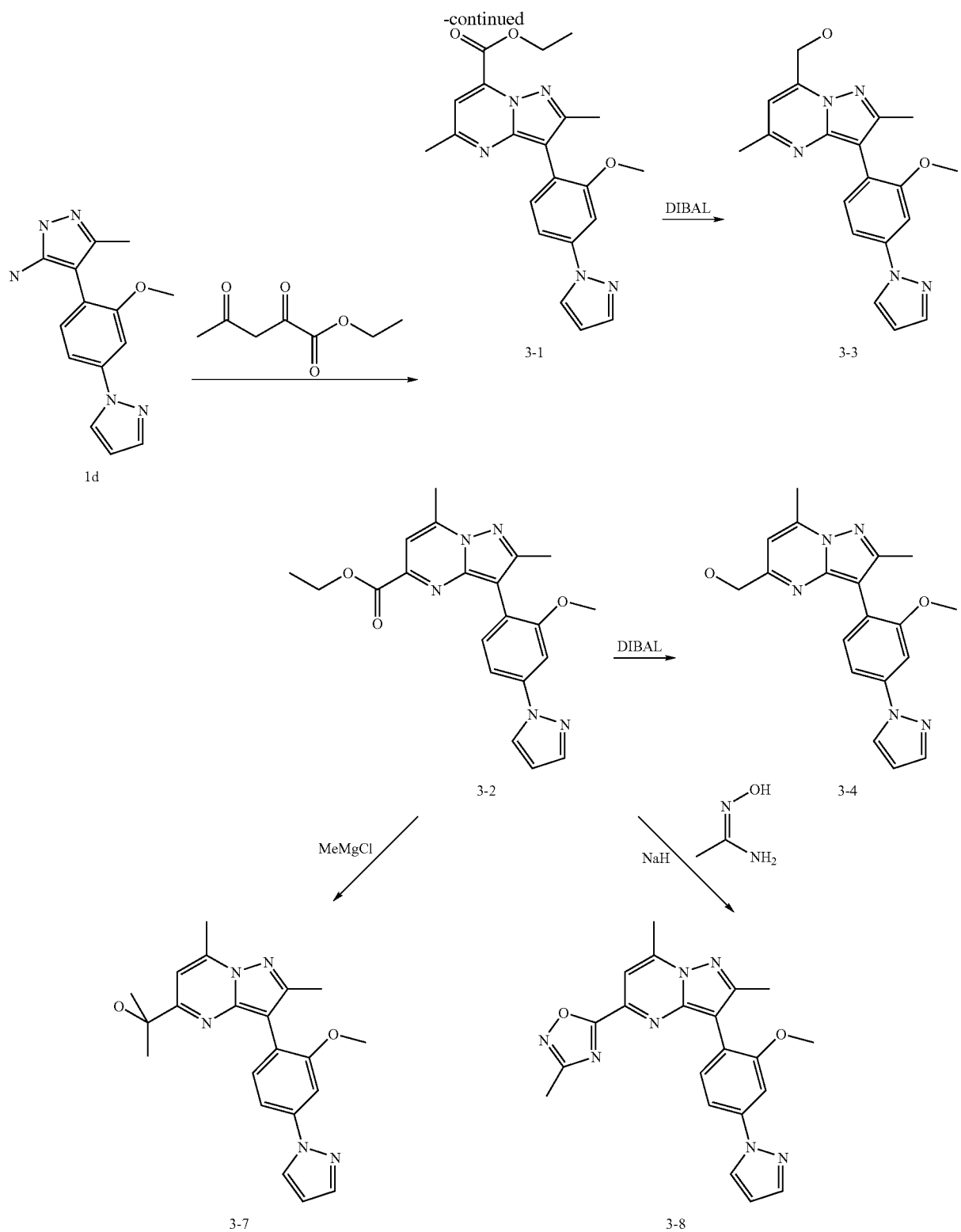
Step 3A:
To 20 mL EtOH were added Cmpd 1d (1.0 g, Example 1, Step 1C) and ethyl-2,4-dioxovalerate (0.82 g) followed by 0.5 mL acetic acid. The reaction mixture was heated at 80° C. for 12 hr. Concentration and purification by silica gel column chromatography yielded Cmpd 3-1 (0.66 g, 46.1% yield) and the inverted addition Cmpd 3-2 (0.47 g, 32.2% yield.)
Step 3B:
To Cmpd 3-1 (30 mg) dissolved in THF (1.5 mL) was added DIBAL (150 uL of 2 M DIBAL in hexane.) The reaction mixture was stirred at room temperature for 2 hr and quenched with water (0.4 mL.) After purification via LC-MS, Cmpd 3-3 (3.3 mg) obtained. Following the same procedure, the reduction of Cmpd 3-2 afforded Cmpd 3-4 (2.6 mg) after purification.

Step 3C:

To 1.5 mL THF was added Cmpd 3-1 (30 mg) followed by CH$_3$MgBr (150 uL of 2 M CH$_3$MgBr in THF.) The reaction mixture was stirred at room temperature for 2 hr and quenched with water. The resulting material was purified by LC-MS to yield Cmpd 3-5 (3.8 mg.) Following this procedure with Cmpd 3-1 and CH$_3$CH$_2$MgBr yielded Cmpd 3-6 (4.1 mg.) after purification. Following the same reaction procedure employing Cmpd 3-2 as the starting reagent and CH$_3$MgBr as nucleophile afforded Cmpd 3-7 (4.0 mg) after purification.

Step 3D:

To THF (1.5 mL) was added acetamidoxime (20 mg) and NaH (10 mg) with stirring at room temperature for 30 min. Cmpd 3-2 (40 mg) was added, and the mixture was heated at 90° C. for 2 hr in a sealed tube. After purification via LC-MS, Cmpd 3-8 obtained (5.5 mg.)

Step 3E:

To Cmpd 3-1 (200 mg) in dioxane:water (9:1) was added LiOH (30 mg.) The reaction proceeded with stirring for 6 hr at room temperature followed by quenching to pH 4 (HCl, 4 N) and extraction between H$_2$O (20 mL) and EtOAc (20 mL.) The organic phase was dried over Na$_2$SO$_4$ and concentrated. The resulting concentrate was purified by silica gel column chromatography (50:50 EtOAc/hexane) to yield Cmpd 3-9 (180 mg.) Compounds presented in Example 3 are tabulated in the following table:

| Cmpd | R$_1$ | R$_2$ | MW | MS | t$_R$ | HPLC Method |
|---|---|---|---|---|---|---|
| 3-1 | H$_3$C— | O-C(=O)-O-CH$_2$CH$_3$ (with CH$_3$) | 391.429 | 392 | 2.681 | 1 |
| 3-2 | CH$_3$CH$_2$-O-C(=O)- | CH$_3$ | 391.429 | 392 | 6.850 | 2 |
| 3-3 | H$_3$C— | OH (with CH$_3$) | 349.392 | 350 | 5.060 | 2 |
| 3-4 | HO-CH$_2$- | CH$_3$ | 349.392 | 350 | 5.030 | 2 |
| 3-5 | H$_3$C— | OH (with two CH$_3$) | 377.446 | 378 | 6.880 | 2 |

-continued

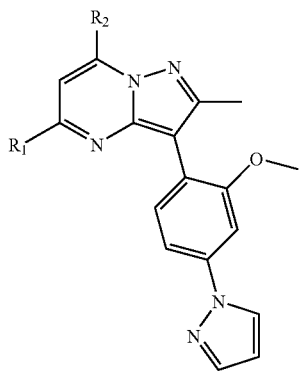

| Cmpd | R₁ | R₂ | MW | MS | $t_R$ | HPLC Method |
|---|---|---|---|---|---|---|
| 3-6 | H₃C– (t-Bu) | –C(Et)₂OH | 405.499 | 406 | 7.980 | 2 |
| 3-7 | HO–C(CH₃)₂– | CH₃ | 377.446 | 378 | 1.264 | 4 |
| 3-8 | 3-methyl-1,2,4-oxadiazol-5-yl | CH₃ | 401.428 | 402 | 6.990 | 2 |
| 3-9 | H₃C– (t-Bu) | –C(CH₃)₂COOH | 363.375 | 364 | 5.740 | 2 |

Example 4

3-(2-Methoxy-4-pyrazol-1-yl-phenyl)-2,5-dimethyl-7-trifluoromethyl-pyrazolo[1,5-a]pyrimidine

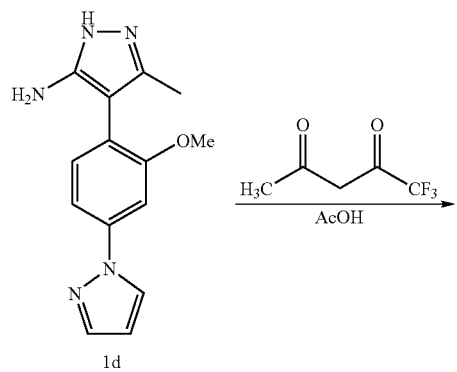

1d

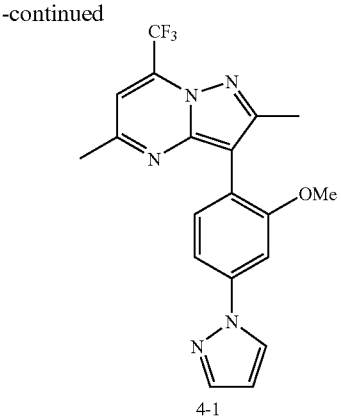

4-1

Step 4A:

A mixture of Cmpd 1d (40 mg, Example 1, Step 1C) and 1,1,1-trifluoropentane-2,4-dione (excess) was heated in AcOH at 150° C. for 15 min with microwave to afford after purification via LC-MS Cmpd 4-1 (29 mg.) Depending on the trifluorodione, the compounds in the following table were synthesized:

| Cmpd | R₁ | MW | MS | $t_R$* |
|---|---|---|---|---|
| 4-1 | H₃C— | 387.363 | 387 | 6.215 |
| 4-2 | (isopropyl-methyl) | 415.417 | 415 | 6.928 |

*All HPLC determinations employed Analytical Method 2.

Example 5

3-(2-Methoxy-4-pyrazol-1-yl-phenyl)-2,5-dimethyl-pyrazolo[1,5-a]pyrimidine-7-carboxylic acid dimethylamide

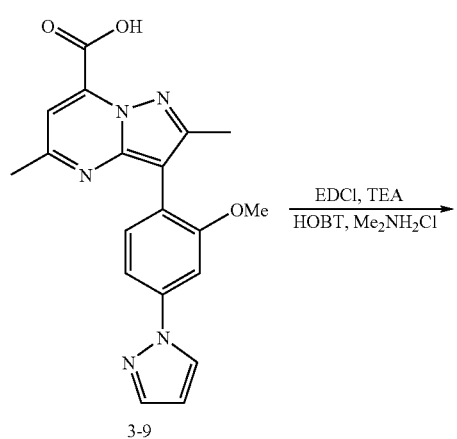

Step 5A:

To a solution of Cmpd 3-9 (50 mg, 0.14 mmol, 1 eq) in DCM (1 mL) was added HOBT (57 mg, 0.42 mmol, 3 eq), TEA (0.12 mL, 0.84 mmol, 6 eq), dimethylamine hydrochloride (34 mg, 0.42 mmol, 3 eq) and EDCl (79 mg, 0.42 mmol, 3 eq). The mixture was stirred at room temperature for 16 hr, then the solvent was evaporated, and the crude reaction mixture was purified by preparative HPLC/MS, providing Cmpd 5-1 (10 mg) as a TFA salt. Depending on the amine employed in the amidation step above, the compounds in the following table were synthesized:

| Cmpd | R₂ | MW | MS | $t_R$* |
|---|---|---|---|---|
| 5-1 | —C(O)N(CH₃)₂ | 390.44 | | 5.17 |
| 5-2 | —C(O)N(CH₂CH₃)₂ | 418.50 | 419.2 | 6.22 |
| 5-3 | —C(O)N(CH₃)CH₂CH₃ | 404.47 | 405.2 | 5.66 |

*All HPLC determinations employed Analytical Method 2.

Example 6

Cyclopentyl-{2-[3-(2-methoxy-4-pyrazol-1-yl-phenyl)-2,5-dimethyl-pyrazolo[1,5-a]pyrimidin-7-yl]-benzyl}-amine

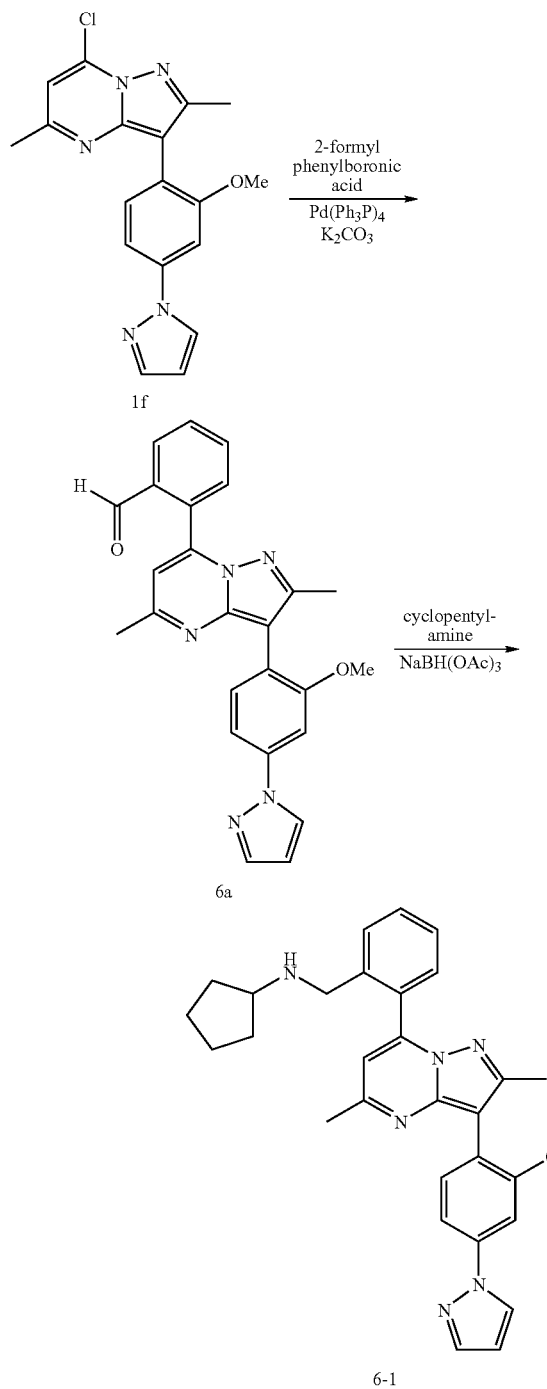

Step 6A:

To a solution of 1f (500 mg, 1.4 mmol, 1 eq) in 1:1 dioxane/water (6 mL) was added 2-formylphenylboronic acid (255 mg, 1.7 mmol, 1.2 eq), followed by potassium carbonate (390 mg, 2.8 mmol, 2.0 eq) and tetrakis(triphenylphosphine)palladium(0) (82 mg, 0.07 mmol, 0.05 eq). The mixture was heated in a sealed tube at 100° C. for 3 hr, then the solvent was removed under vacuum. The residue was taken up in ethyl acetate and washed with water and brine. The organic layer was dried over sodium sulfate, filtered, concentrated, and the residue was purified by silica gel column chromatography using 1:1 hexanes/ethyl acetate as eluent, to afford 6a (500 mg, 85%) as a yellow solid.

Step 6B:

Sodium triacetoxyborohydride (80 mg, 0.38 mmol, 2 eq) was added at RT to a solution of 6a (80 mg, 0.19 mmol, 1 eq) and acetic acid (0.011 mL, 0.19 mmol, 1 eq) in dichloroethane (1 mL). The mixture was stirred at RT for 16 hr, then the mixture was concentrated, taken up in methanol, and purified directly by preparative HPLC/MS, providing 6-1 (36 mg, 38% yield) as a TFA salt.

Depending on the amine employed in the reductive amination step above, the compounds of the following table were synthesized:

| Cmpd | $R_2$ | MW | MS | $t_R$* |
|---|---|---|---|---|
| 6-1 | cyclopentyl-NH-CH2-(2-substituted phenyl) | 492.62 | 493.4 | 5.69 |
| 6-2 | cyclohexyl-NH-CH2-(2-substituted phenyl) | 506.65 | 507.4 | 5.95 |
| 6-3 | cyclobutyl-NH-CH2-(2-substituted phenyl) | 478.60 | 479.1 | 5.49 |

-continued
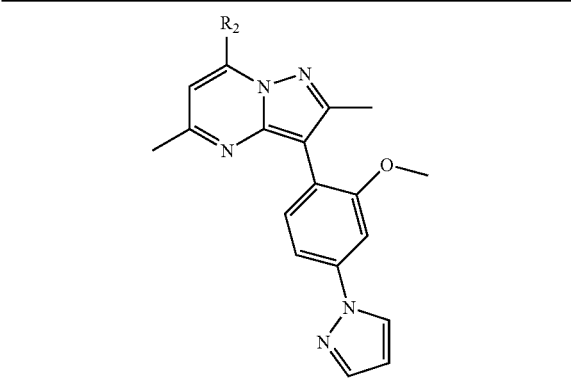
| Cmpd | R₂ | MW | MS | $t_R$* |
|---|---|---|---|---|
| 6-4 | 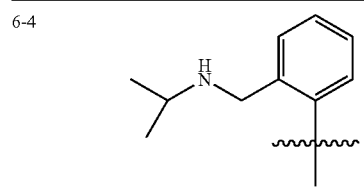 | 466.59 | 467.1 | 5.33 |
| 6-5 | 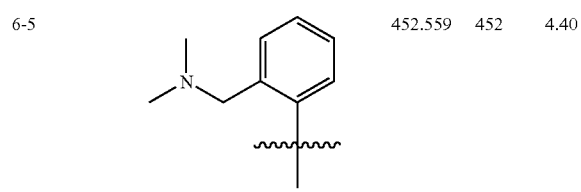 | 452.559 | 452 | 4.40 |
| 6-6 | 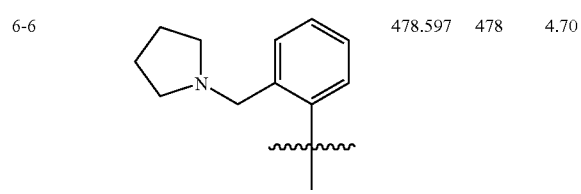 | 478.597 | 478 | 4.70 |
| 6-7 | 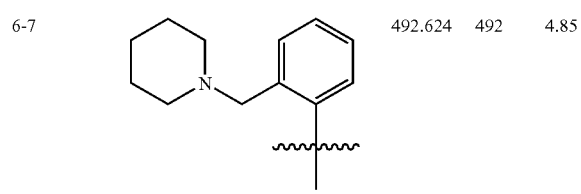 | 492.624 | 492 | 4.85 |
| 6-8 | 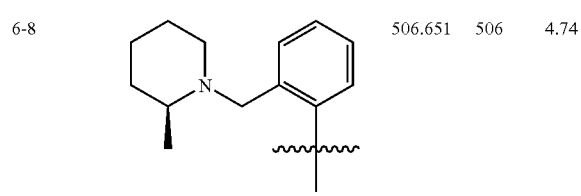 | 506.651 | 506 | 4.74 |
| 6-9 | 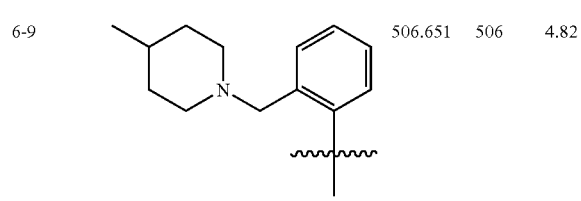 | 506.651 | 506 | 4.82 |
-continued
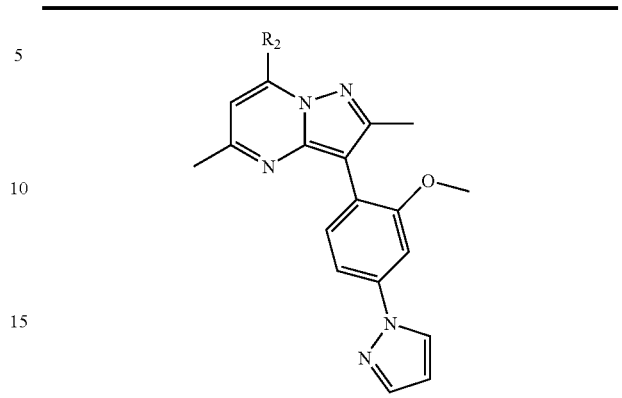
| Cmpd | R₂ | MW | MS | $t_R$* |
|---|---|---|---|---|
| 6-10 | 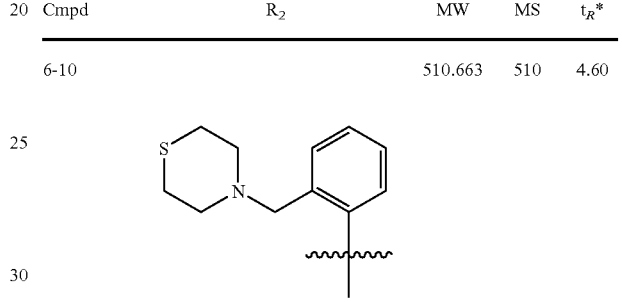 | 510.663 | 510 | 4.60 |
| 6-11 | 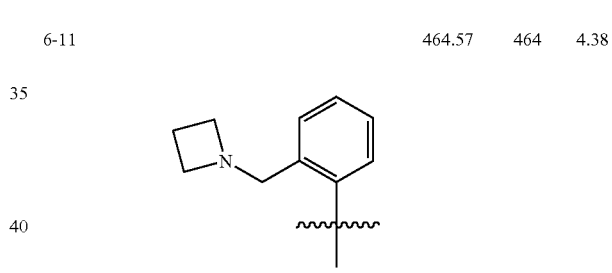 | 464.57 | 464 | 4.38 |
| 6-12 | 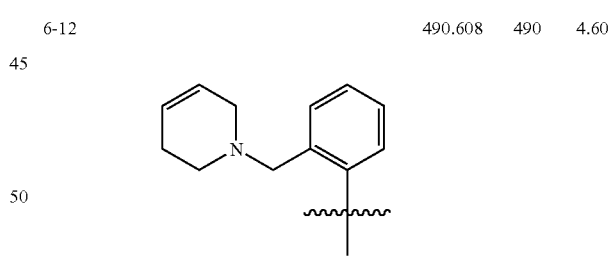 | 490.608 | 490 | 4.60 |
| 6-13 | 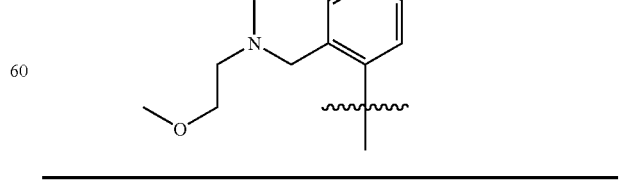 | 496.612 | 496 | 4.57 |
*All HPLC determinations employed Analytical Method 2.

Example 7
3-(2-Methoxy-4-pyrazol-1-yl-phenyl)-2,5-dimethyl-7-[2-(2-morpholin-4-yl-ethyl)-phenyl]-pyrazolo[1,5-a]pyrimidine
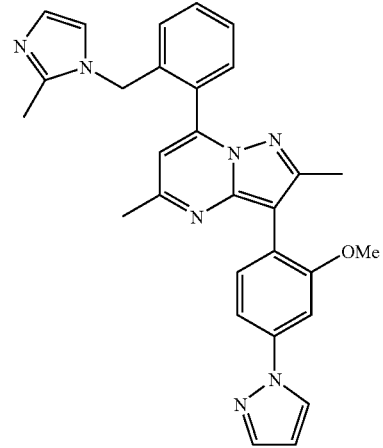
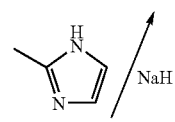
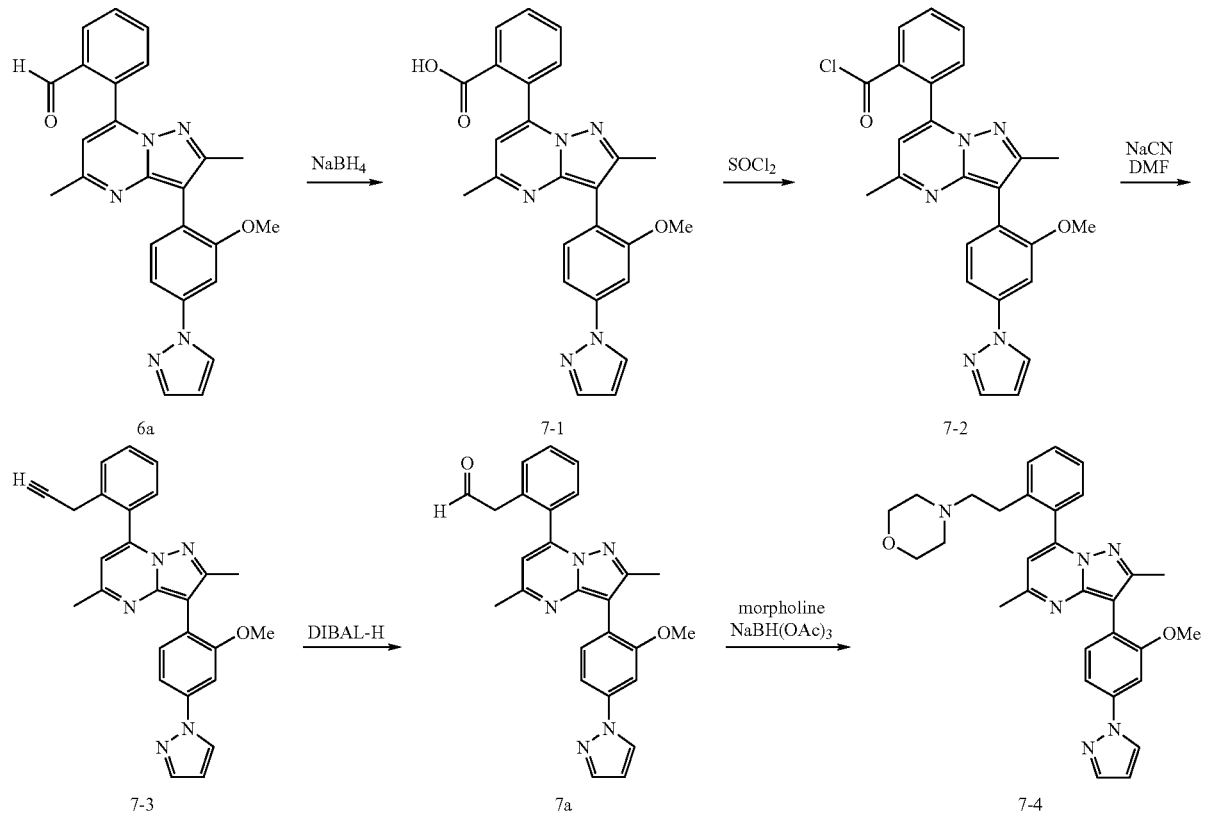

Step 7A:

To a suspension of 6a (345 mg, 0.82 mmol) in 1:1 THF/methanol (4 mL) at RT was added carefully sodium borohydride (62 mg, 1.6 mmol, 2 eq). The mixture was stirred for 30 min, then water was added and the mixture was extracted with DCM. The combined organic layers were washed with water and brine, then dried over sodium sulfate, filtered, and concentrated to provide 7-1 (450 mg, 90%) as a solid, which was used without further purification.

Step 7B:

Thionyl chloride (0.17 mL, 2.3 mmol, 2.2 eq) was added to a solution of 7-1 (450 mg, 1.05 mmol, 1 eq) in DCM (5 mL) at RT. The mixture was stirred at RT for 30 min, then water was added and the mixture was extracted with DCM. The combined organic extracts were dried over sodium sulfate, filtered, and concentrated to provide 7-2 (420 mg, 90%) as a yellow solid.

Step 7-C

Sodium hydride (11 mg of 60% dispersion in mineral oil, 0.28 mmol, 4 eq) was added to a solution of 2-Methylimidazole (17 mg, 0.21 mmol, 3 eq) in 2 ml DMF at rt. The mixture was stirred for 10 min, then a solution of 7-2 (30 mg, 0.07 mmol, 1 eq) in 0.2 ml DMF was added and the mixture was stirred at rt for 17 h. The mixture was diluted with methanol, then purified directly by preparative HPLC/MS, providing 7-X (6 mg) as a TFA salt.

Step 7D:

Sodium cyanide (3.3 mg, 0.067 mmol, 3 eq) was added to a solution of 7-2 (10 mg, 0.023 mmol, 1 eq) in DMSO (3 mL) at RT. The mixture was stirred at RT for 2 hr, then water was added and the mixture was extracted with DCM. The combined organic layers were washed with water and brine, then dried over sodium sulfate, filtered, and concentrated to provide crude 7-3 (8 mg, 80% yield) as a solid.

Step 7E:

DIBAL-H (0.23 mL of a 1.5 M solution in toluene, 0.35 mmol, 3 eq) was added to a solution of 7-3 (50 mg, 0.11 mmol) in DCM (1 mL) at −78° C. The mixture was stirred at −78° C. for 20 min, then was allowed to warm to RT. Water was added and the mixture was stirred for 10 min, then the aqueous layer was extracted with two additional portions of DCM. The combined organic extracts were washed with water and brine, were dried over sodium sulfate, filtered through Celite®, and concentrated. The residue was purified by prep HPLC/MS to provide 7a (15 mg) as a TFA salt.

Step 7F:

Sodium triacetoxyborohydride (15 mg, 0.069 mmol, 2 eq) was added to a room temperature solution of 7a (15 mg, 0.034 mmol, 1 eq) and acetic acid (0.002 mL, 0.034 mmol, 1 eq) in DCM (1 mL). The mixture was stirred at RT for 16 hr, then the mixture was concentrated, taken up in methanol, and purified directly by preparative HPLC/MS, providing 7-4 (11 mg, 50% yield) as a TFA salt.

The following table summarizes the compounds of Example 7. By varying the amine employed in the reductive amination step above, Cmpds 7-5 and 7-6, included in the table, were synthesized by the methods of Step 7E:

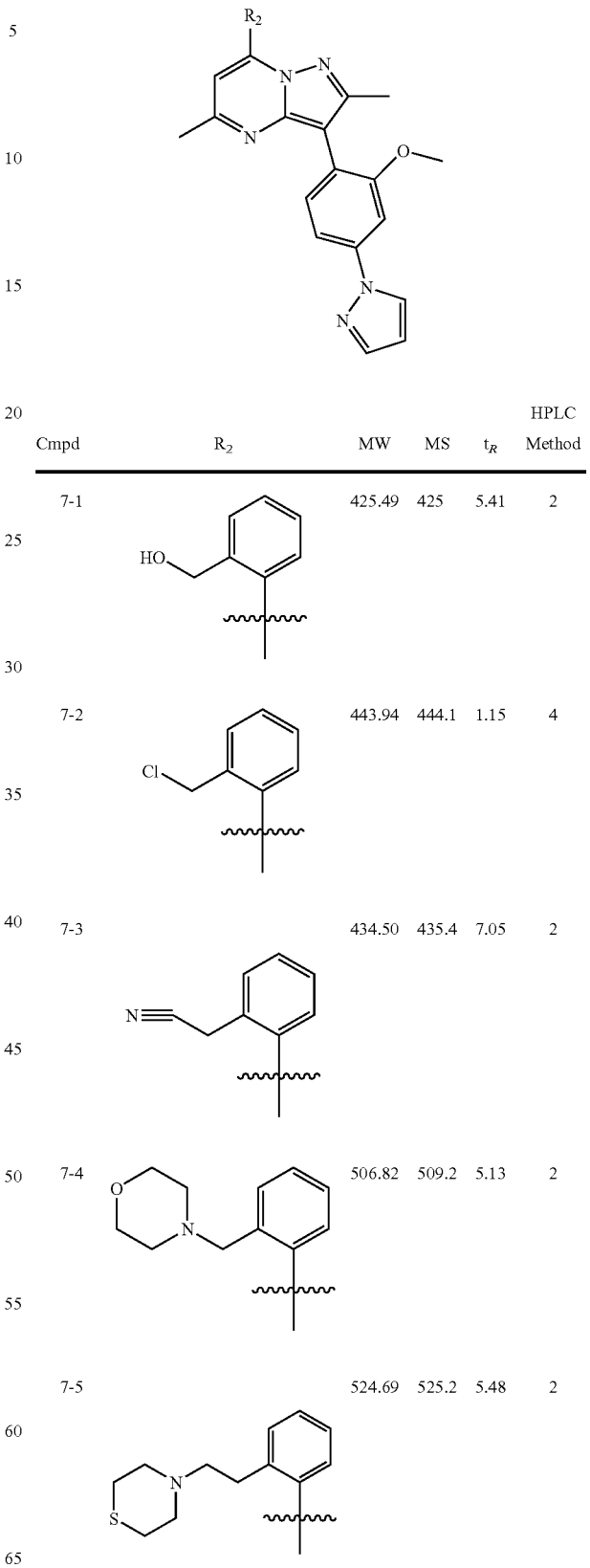

| Cmpd | $R_2$ | MW | MS | $t_R$ | HPLC Method |
|---|---|---|---|---|---|
| 7-1 | | 425.49 | 425 | 5.41 | 2 |
| 7-2 | | 443.94 | 444.1 | 1.15 | 4 |
| 7-3 | | 434.50 | 435.4 | 7.05 | 2 |
| 7-4 | | 506.82 | 509.2 | 5.13 | 2 |
| 7-5 | | 524.69 | 525.2 | 5.48 | 2 |

| Cmpd | R₂ | MW | MS | $t_R$ | HPLC Method |
|------|-----|--------|-------|------|------|
| 7-6  |     | 496.612 | 497.2 | 5.18 | 2 |
| 7-7  |     | 489.58  | 490.2 | 4.94 |   |

Example 8

3-(2-Methoxy-4-pyrazol-1-yl-phenyl)-2,5-dimethyl-7-(3-methyl-pyridin-2-yl)-pyrazolo[1,5-a]pyrimidine

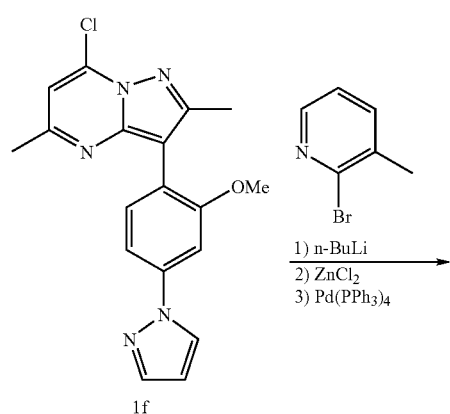

Step 8A:

To a solution of 2-bromo-3-methylpyridine (4.85 g, 28.2 mmol) in dry THF (8.0 mL) cooled to −70° C. was added n-BuLi (1.6 M solution in hexane, 17.6 mL, 28.2 mmol) dropwise. The reaction mix was stirred at −70° C. for 30 min, then ZnCl₂ (0.5 M solution in THF, 66.0 mL, 34 mmol) was added over 5 min. The mixture was allowed to warm to 0° C. over 1 hr, then Cmpd 1f (1.66 g, 4.70 mmol) and tetrakis(triphenylphosphine)palladium(0) (326 mg, 0.28 mmol) were added. The mixture was then heated to reflux for 4 hr. The cooled reaction mixture was quenched with water, the THF was evaporated and the resulting aqueous mixture was extracted with ethyl acetate. The combined organic layers were dried over sodium sulfate, filtered, concentrated, and the residue was chromatographed on silica gel using 1:3 hexanes/ethyl acetate to give 8-1 free base (1.6 g, 83%) as a yellow solid. To a solution of 8-1 (1.6 g, 3.9 mmol) in 7:1 ethyl acetate/chloroform (100 mL) was added hydrogen chloride (4.0 mL of a 2.0 M solution in ether, 8.0 mmol) at 0° C. The suspension was diluted with ether, then the solid was collected on a fritted glass filter and rinsed with ether to obtain 8-1 HCl salt (1.7 g, 98%) after drying under high vacuum.

Depending on the halide employed in Step 8A above, the compounds of the following table were synthesized:

-continued

| Cmpd | R₂ | MW | MS | t_R* |
|---|---|---|---|---|
| 8-1 | 3-methylpyridin-2-yl | 410.48 | 411 | 5.400 |
| 8-2 | 6-methylpyridin-2-yl | 410.48 | 411 | 5.770 |
| 8-3 | 2-methoxypyridin-3-yl | 426.48 | 427 | 5.690 |
| 8-4 | 6-methoxypyridin-3-yl | 440.51 | 441 | 6.240 |
| 8-5 | 1-methylimidazol-2-yl | 399.456 | 399 | 4.130 |
| 8-6 | 6-methoxypyridin-2-yl | 426.478 | 426 | 6.410 |
| 8-7 | pyridin-2-yl | 396.452 | 396 | 5.720 |
| 8-8 | pyridin-3-yl | 396.452 | 396 | 4.940 |
| 8-9 | 4-methylpyridin-2-yl | 410.479 | 410 | 5.640 |
| 8-10 | n-pentyl | 375.474 | 375 | 6.260 |
| 8-11 | 3-methoxypyridin-2-yl | 426.478 | 426 | 5.850 |

-continued

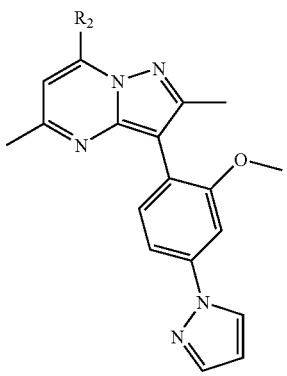

| Cmpd | R₂ | MW | MS | $t_R$* |
|---|---|---|---|---|
| 8-12 | (4-methylpyridin-3-yl) | 410.479 | 410 | 4.700 |

*All HPLC determinations employed Analytical Method 2.

Example 9

Synthesis of Reagent
2-methyl-4-(pyrazol-1-yl)phenylboronic Acid Pinacol Ester

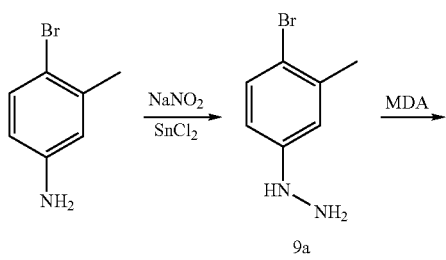

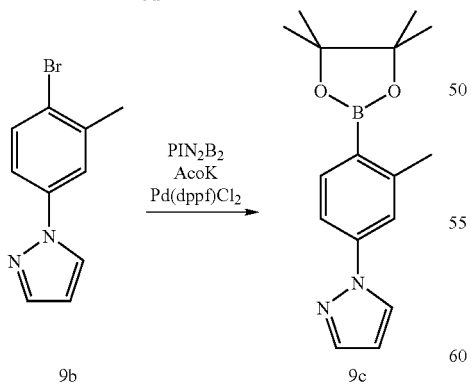

Step 9A:

4-Bromo-3-methylaniline (10.2 g) was suspended in 6N HCl (85 mL) and cooled to 0° C. A solution of sodium nitrite (4 g in 40 mL H₂O) was added over 10 min. The reaction was stirred for 15 min at 0° C. followed by the addition of stannous chloride dihydrate (36 g in 25 mL 12N HCl.) The reaction was stirred for 2 hr at 0° C. The reaction was filtered and the filter cake washed with cold H₂O to afford 4-bromo-3-methylphenylhydrazine hydrochloride (Cmpd 9a, 20 g) as a tan solid.

Step 9B:

The compound resulting from Step 9A (20 g) was suspended in 50 mL ethanol. Malondialdehyde bis-dimethylacetal (11.0 mL, 67 mmol) was added and the reaction was heated to 85° C. for 2 hr. The reaction mixture was neutralized with sodium bicarbonate and extracted by washing with DCM. The combined organic layers were dried over magnesium sulfate and concentrated. The residue was taken up in ethyl acetate and the mixture filtered through a pad of Celite®. The filtrate was evaporated, and the oily residue was purified by column chromatography (1:1 ethyl acetate:hexanes) to afford 1-(4-bromo-3-methylphenyl)pyrazole (Cmpd 9b, 9.6 g, 73%) as an amber oil.

Step 9C:

To a solution of Cmpd 9b (2.0 g in 15 mL dioxane) was added bis(pinacolato)diboron (2.4 g), potassium acetate (2.4 g) and 1,1'-bis(diphenylphosphino) ferrocene dichloropalladium (II) (500 mg.) The reaction was heated to 85° C. for 12 hr. The reaction mixture was filtered through a pad of Celite® and the filter cake washed with ethyl acetate. The filtrate was concentrated to a brown liquid which was purified by column chromatography (20% ethyl acetate:hexanes) to afford 2-methyl-4-(pyrazol-1-yl)phenylboronic acid pinacol ester (Cmpd 9c, 1.8 g, 75%), as a yellow oil; LC/MS: [M+H]=285.0.

Also prepared by the methods above were 2-chloro-4-(pyrazol-1-yl)phenylboronic acid pinacol ester (9d) and 2-methyl-3-(pyrazol-1-yl)phenylboronic acid pinacol ester (9e).

Example 10

7-(2-Fluoro-3-methoxy-phenyl)-2,5-dimethyl-3-(4-methyl-6-pyrazol-1-yl-pyridin-3-yl)-pyrazolo[1,5-a]pyrimidine

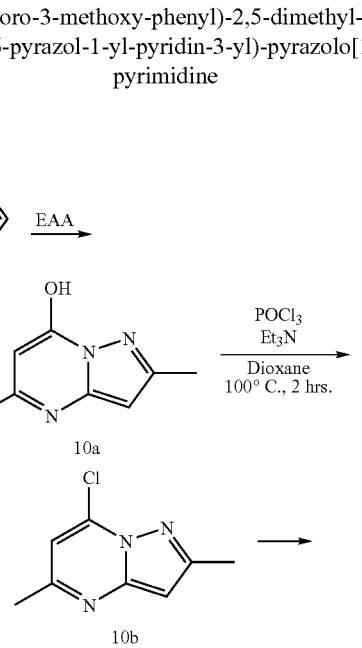

-continued

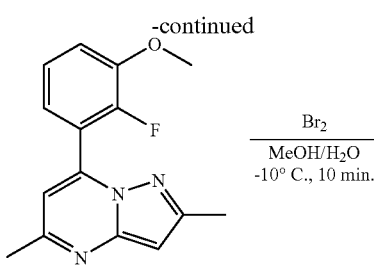

10c

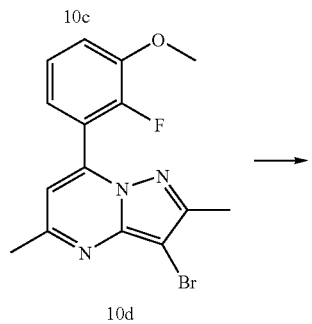

10d

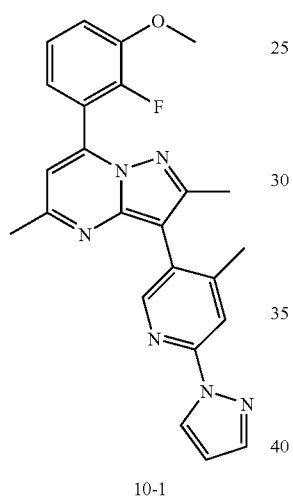

10-1

Step 10A:

A solution of 3-amino-5-methylpyrazole (20.0 g, 206 mmol), ethyl acetoacetate (32.0 g, 247 mmol), acetic acid (6 mL), and dioxane (150 mL) was refluxed for 16 hr. A white solid precipitated, which was collected by filtration. The filter cake was washed with ether to provide 10a (29.0 g, 86%) as a white solid.

Step 10B:

To a suspension of compound 10a (5.0 g, 31 mmol) in 1,4-dioxane (30 mL) was added triethylamine (8.50 mL, 62 mmol) and phosphorous oxychloride (7.4 mL, 77 mmol). The reaction was heated under nitrogen at 100° C. for 2 hr. The reaction mixture was cooled in an ice bath, then treated successively with water and aqueous sodium bicarbonate solution (final pH 8). Dichloromethane was added and the mixture was washed 3× with water. The combined organic layers were dried over magnesium sulfate, filtered, and concentrated to a dark brown oil. The crude product was purified by silica gel chromatography using 30% ethyl acetate in hexanes as eluent, providing 10b (3.8 g, 70%) as a white solid.

Step 10C:

To a mixture of 80 mL dioxane and 8 mL water were added compound 10b (3.3 g, 18 mmol, 1 eq), 2-fluoro-3-methoxyphenylboronic acid (4.3 g, 26 mmol, 1.4 eq), potassium carbonate (5.0 g, 36 mmol, 2 eq), and tetrakis(triphenylphosphine)palladium(0) (1.5 g, 1.3 mmol, 0.07 eq). The mixture was stirred and heated at 100° C. for 16 hr, then was allowed to cool and water (75 mL) was added. The mixture was extracted with ethyl acetate, then the combined organic layers were dried over sodium sulfate, filtered, and concentrated. The residue was purified by silica gel chromatography eluting with 4:1 hexane/ethyl acetate to provide Cmpd 10c (3.78 g, 76%) as white solid.

Step 10D:

Bromine (1.77 g, 11 mmol) was added to a solution of 10c (3.0 g, 11 mmol) in methanol (30 mL) at −10° C. After 10 min, the mixture was filtered to collect the precipitate that had formed. The filter cake was washed with cold methanol, and was then dried under vacuum to yield 10d (3.15 g, 83%) as a yellow solid.

Step 10E:

Suzuki reaction of Cmpd 10d (460 mg, 1.3 mmol) according to the procedure of Step 10C above, using Cmpd 12-1 in place of 2-fluoro-3-methoxyphenylboronic acid, yielded Cmpd 10-1 (15 mg, solid) following purification by prep HPLC/MS and silica gel chromatography (4:1 hexane/ethyl acetate eluent).

Depending on the boronate ester or acid employed in the final Suzuki reaction, the compounds listed in the following table were synthesized and purified by preparative LC-MS:

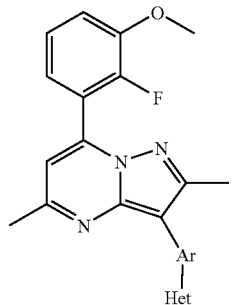

| Cmpd | AR-HET | MW | MS | $t_R$* |
|---|---|---|---|---|
| 10-1 | 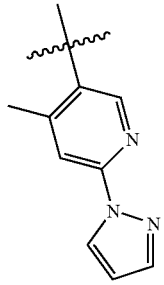 | 428.469 | 429 | 8.110 |
| 10-2 | 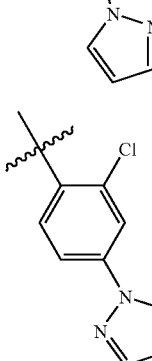 | 447.899 | 447 | 6.390 |

-continued
| Cmpd | AR-HET | MW | MS | $t_R$* |
|---|---|---|---|---|
| 10-3 | 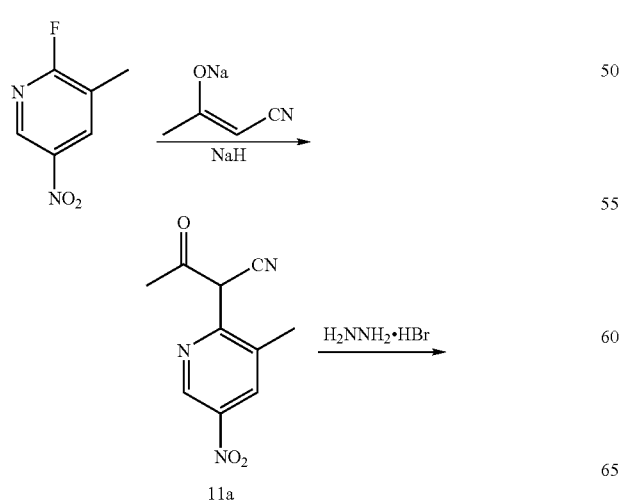 | 427.481 | 427 | 6.330 |
| 10-4 | | 427.481 | 427 | 7.670 |
*All HPLC determinations employed Analytical Method 2.
Example 11
7-(2-Fluoro-3-methoxy-phenyl)-2,5-dimethyl-3-(3-methyl-5-pyrazol-1-yl-pyridin-2-yl)-pyrazolo[1,5-a]pyrimidine
-continued
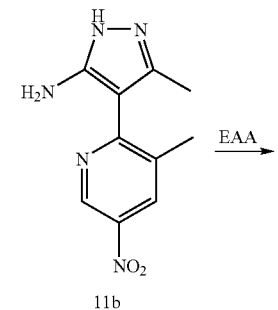
11b
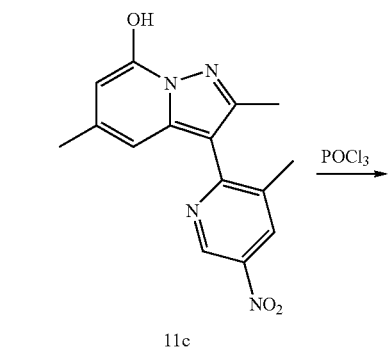
11c
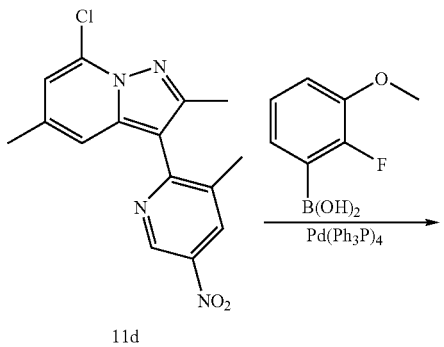
11d
11e
11a

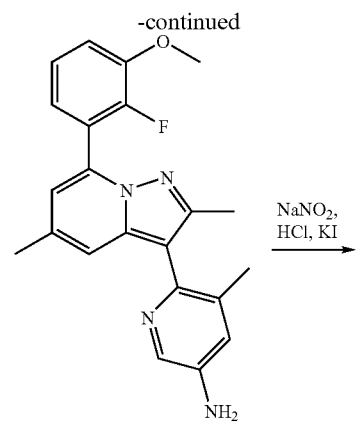

11f

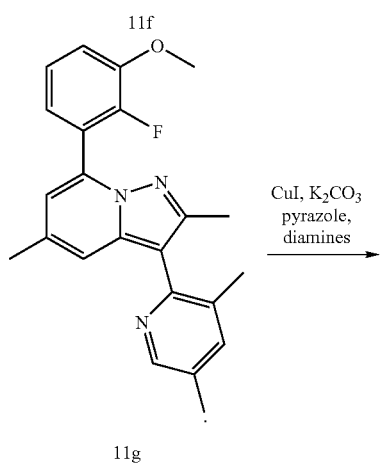

11g

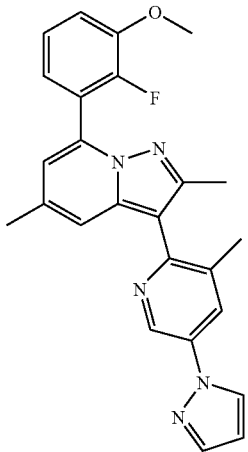

11-1

Step 11A:

Sodium hydride (1.54 g of 60% dispersion in oil, 38.5 mmol, 2 eq) was added to a solution of cyanoacetone sodium salt (2.5 g, 23 mmol, 1.2 eq) in DMF (40 mL) at RT. The mixture was stirred for 15 min, then a solution of 2-fluoro-3-methyl-5-nitropyridine (3.0 g, 19.2 mmol, 1.0 eq) in 10 mL DMF was added dropwise. The reaction mixture was stirred at RT for 6 hr. The reaction was quenched with 5 g ice, followed by 150 mL water and 10 mL acetic acid. The mixture was extracted with ethyl acetate, then the combined organic extracts were dried over sodium sulfate, filtered, and concentrated. The residue was purified by silica gel chromatography using 30% ethyl acetate in hexanes as eluent, providing 11a (1.85 g, 44% yield) as an orange oil.

Step 11B:

A mixture of 11a (1.8 g, 8.2 mmol, 1.0 eq), hydrazine monohydrobromide (1.0 g, 8.8 mmol, 1.1 eq), ethanol (30 mL) and water (3 mL) was heated at reflux for 17 hr. The solvent was evaporated, and the residue was purified directly by silica gel chromatography using 1:1 hexanes/ethyl acetate as eluent, obtaining 11b (1.8 g, 94% yield) as a yellow foam.

Step 11C:

A mixture of 11b (1.8 g, 7.7 mmol, 1.0 eq), ethanol (15 mL), acetic acid (15 mL), and ethyl acetoacetate (1.6 g, 12.4 mmol, 1.6 eq) was heated in a sealed tube at 105° C. for 19 hr. The solvent was evaporated, and the residue was deposited on a fritted glass filter, rinsing with ether, to provide 11c (1.0 g, 43% yield) as a yellow solid.

Step 11D:

A mixture of 11c (800 mg, 2.7 mmol, 1.0 eq), phosphorous oxychloride (900 mg, 5.9 mmol, 2.2 eq), and acetonitrile (15 mL) was refluxed for 3 hr. The reaction was poured onto ice, then the mixture was extracted with ethyl acetate. The combined ethyl acetate extracts were washed with aqueous sodium bicarbonate, dried over sodium sulfate, filtered and concentrated to provide 11d (640 mg, 76%) as a yellow solid.

Step 11E:

A suspension of 11d (640 mg, 2.0 mmol, 1 eq), 2-fluoro-3-methoxyphenylboronic acid (480 mg, 3.8 mmol, 1.4 eq), potassium carbonate (555 mg, 4.0 mmol, 2.0 eq), tetrakis(triphenylphosphine)palladium(0) (230 mg, 0.2 mmol, 0.1 eq) in 20 mL dioxane and 2 mL water was stirred and heated at 100° C. for 16 hr. Water (50 mL) was added and the mixture was extracted with ethyl acetate (50 mL). The organic layer was dried over sodium sulfate, filtered, and concentrated. The residue was triturated with methanol to obtain 11e (300 mg, 37%) as a yellow solid.

Step 11F:

10% Pd/C (100 mg) was added to a nitrogen-sparged solution of 11e (300 mg, 0.74 mmol, 1.0 eq) in 20 mL ethanol and 10 mL THF. The mixture was shaken in a Parr shaker under 40 psi hydrogen gas at RT for 6 hr. The mixture was purged with nitrogen and filtered. The filtrate was concentrated to provide 11f (260 mg, 94% yield) as a yellow oil.

Step 11G:

A solution of sodium nitrite (60 mg, 0.87 mmol, 1.3 eq) in water (10 mL) was added dropwise to an ice-cold solution of 11f (260 mg, 0.69 mmol, 1.0 eq) in 4N hydrochloric acid (5 mL). The mixture was stirred at 0° C. for 1 hr, followed by addition of 10 mL of half-saturated aqueous potassium iodide. The mixture was stirred at RT for 16 hr, then 50 mL saturated aqueous sodium bicarbonate solution was added and the mixture was extracted 2×50 mL ethyl acetate. The combined organic layers were dried over sodium sulfate, filtered, concentrated and the residue purified by silica gel chromatography using 4:1 hexanes/ethyl acetate as eluent, providing 11 g (170 mg, 51% yield) as a yellow solid.

Step 11H:

To a solution of 11 g (170 mg, 0.35 mmol, 1.0 eq) in dioxane (6 mL) were added potassium carbonate (200 mg, 1.45 mmol, 4.1 eq), pyrazole (60 mg, 0.89 mmol, 2.5 eq), copper(I) iodide (60 mg, 0.32 mmol, 0.9 eq), trans-1,2-diaminocyclohexane (36 mg, 0.32 mmol, 0.9 eq), and N,N'-dimethylethylenediamine (28 mg, 0.32 mmol, 0.9 eq). The mixture was stirred and heated in a sealed tube at 100° C. for 19 hr. The reaction mixture was filtered through a Celite® pad, concentrated, and purified by prep HPLC/MS to obtain Cmpd 11-1 (70 mg, 37% yield) as a TFA salt; MW: 428.47; LC/MS: 429 [MH]⁺; $t_R$: 5.390, Anal. Meth. 2.

Example 12

4-Methyl-2-pyrazol-1-yl-5-pyridylboronic Acid

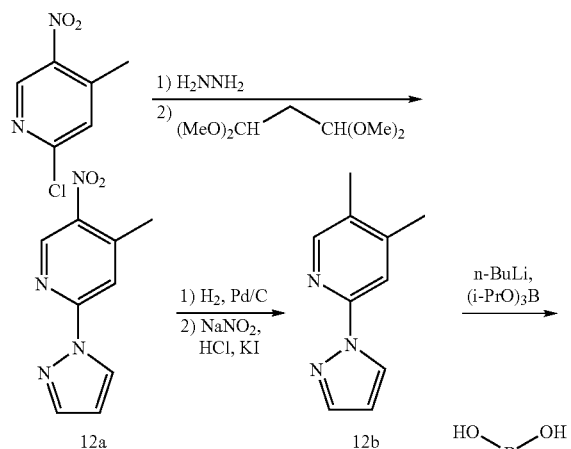

Step 12A:

2-Chloro-4-methyl-5-nitropyridine (5.0 g, 29 mmol, 1.0 eq) was dissolved in 50 mL hydrazine solution (1M solution in THF) and the mixture was stirred and heated in a sealed tube at 80° C. for 22 hr. The cooled reaction mixture was filtered, and the solid obtained was washed with ether to provide 5.7 g of a greenish brown solid.

A mixture of this solid (5.7 g, 24 mmol, 1.0 eq), malonaldehyde bis(dimethylacetal) (5.9 g, 31 mmol, 1.3 eq), and acetic acid (50 mL) was stirred and heated in a sealed tube at 80° C. for 5 hr. The solvent was evaporated, then aqueous sodium bicarbonate solution (200 mL) was added and the mixture was extracted with 2×200 mL ethyl acetate. The combined organic layers were dried over sodium sulfate, filtered, and concentrated. The residue was recrystallized from ethanol to obtain 12a (2.6 g, 53% yield) as a yellow solid.

Step 12B:

A mixture of 12a (2.6 g, 13 mmol) and 10% Pd/C (200 mg) in 30 mL of 1:1 THF/methanol was shaken in a Parr apparatus under 40 psi hydrogen at RT for 2 hr. The reaction mixture was filtered through a Celite® pad and the filtrate concentrated to a light green oil. The oil was resuspended in 10 mL of 3N hydrobromic acid, cooled to 0° C., then treated dropwise with a solution of sodium nitrite (835 mg, 12 mmol, 1.1 eq) in 2 mL water. The mixture was stirred at 0° C. for 1 hr, then 2 mL of half-saturated potassium iodide was added and the mixture was stirred at RT for 22 hr. Saturated aqueous sodium bicarbonate solution was added, then the mixture was extracted with 2×100 mL ethyl acetate, and the combined organic layers were dried over sodium sulfate, filtered, and concentrated. The residue was purified by silica gel chromatography using 4:1 hexanes/ethyl acetate as eluent, to provide 12b (1.23 g, 33%) as a yellow solid.

Step 12C:

n-Butyllithium (1.8 mL of a 2.0 M solution in pentane, 3.6 mmol) was added dropwise to a solution of Cmpd 12b (600 mg, 2.1 mmol) and triisopropylborate (900 mg, 4.8 mmol) in 5 mL THF at −78° C. The mixture was allowed to warm to RT over 1 hr, then the mixture was cooled to −78° C. and treated with additional triisopropylborate (400 mg, 2.1 mmol), followed by additional n-butyllithium (0.5 mL of a 2.0 M solution in pentane, 1.0 mmol). The mixture again was allowed to warm to RT over 1 hr, then 0.8 mL of 1 N hydrochloric acid was added and the mixture was stirred for 1 hr. The mixture was filtered, rinsing the solid with methanol and ethyl acetate, then the filtrate was concentrated. The residue was chromatographed on silica gel, eluting with 1:1 hexanes/ethyl acetate to provide Cmpd 12-1 (220 mg, 52% yield) as a red solid.

Example 13

7-(4-Chloro-phenoxymethyl)-3-(2-methoxy-4-pyrazol-1-yl-phenyl)-2,5-dimethyl-pyrazolo[1,5-a]pyrimidine

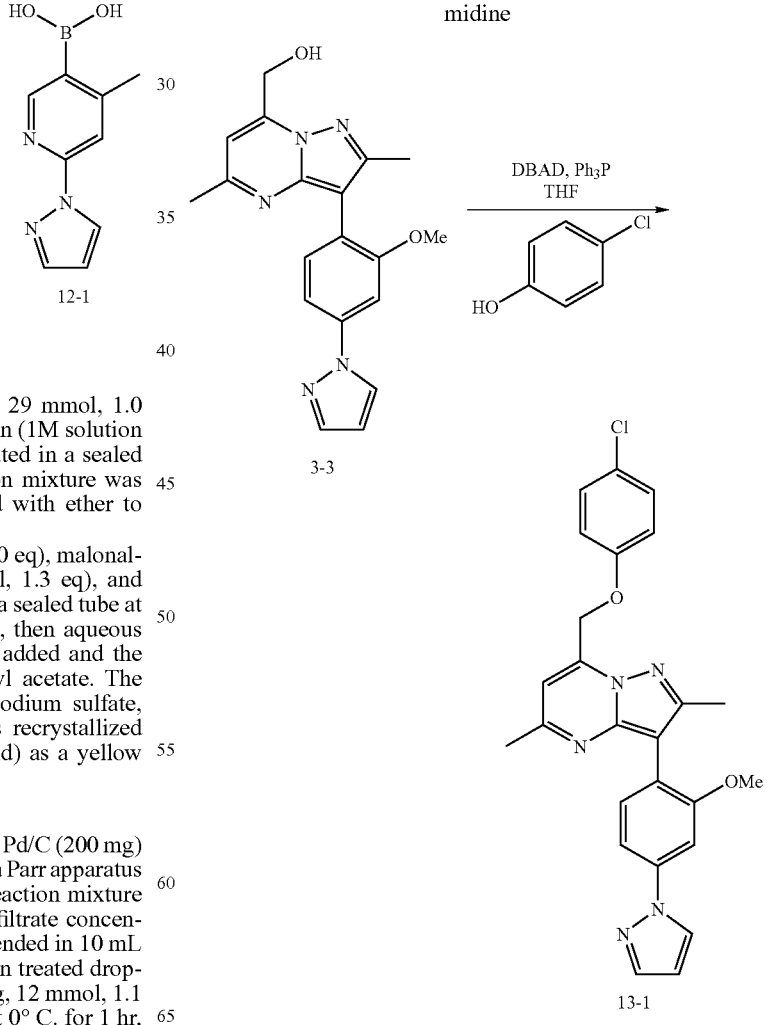

Step 13A:

To a solution of Cmpd 3-3 (25 mg, 0.072 mmol, 1 eq) in THF (1.5 mL) were added di-tert-butylazodicarboxylate (30 mg, 0.11 mmol, 1.5 eq), triphenylphosphine (30 mg, 0.11 mmol, 1.5 eq) and 4-chlorophenol (30 mg, 0.023 mmol, 3.3 eq). The mixture was stirred at RT for 17 hr, then the solvent was evaporated and the residue was purified by silica gel chromatography, eluting with hexanes/ethyl acetate to provide Cmpd 13-1 (8 mg) as a solid.

Depending on the phenol employed, the compounds listed in the following table were synthesized and purified by preparative LC-MS:

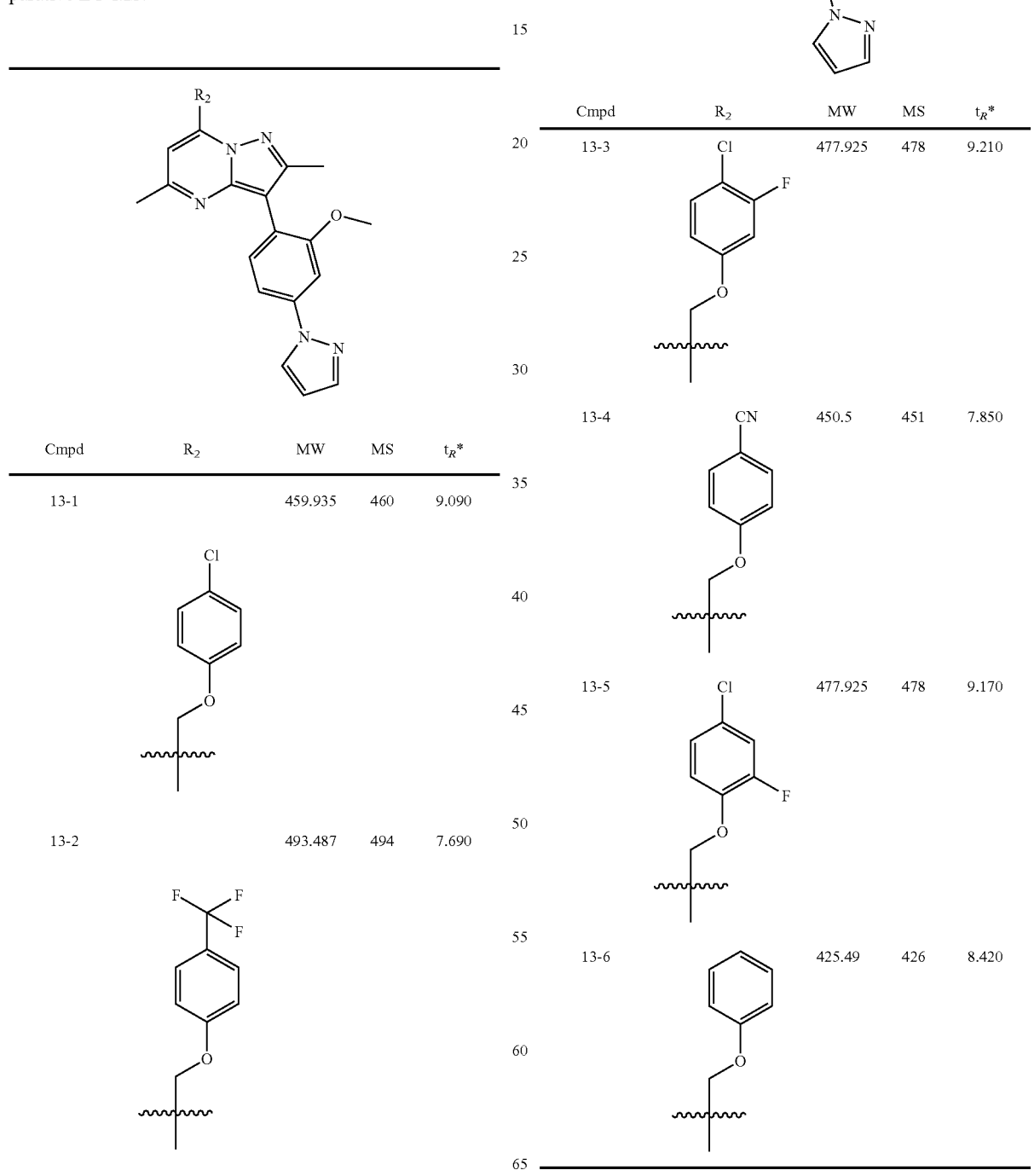

| Cmpd | R$_2$ | MW | MS | t$_R$* |
|---|---|---|---|---|
| 13-1 | | 459.935 | 460 | 9.090 |
| 13-2 | | 493.487 | 494 | 7.690 |
| 13-3 | | 477.925 | 478 | 9.210 |
| 13-4 | | 450.5 | 451 | 7.850 |
| 13-5 | | 477.925 | 478 | 9.170 |
| 13-6 | | 425.49 | 426 | 8.420 |

*All HPLC determinations employed Analytical Method 2.

Example 14

6-{3-[3-(2-Methoxy-4-pyrazol-1-yl-phenyl)-2,5-dimethyl-pyrazolo[1,5-a]pyrimidin-7-yl]-propoxy}-nicotinonitrile

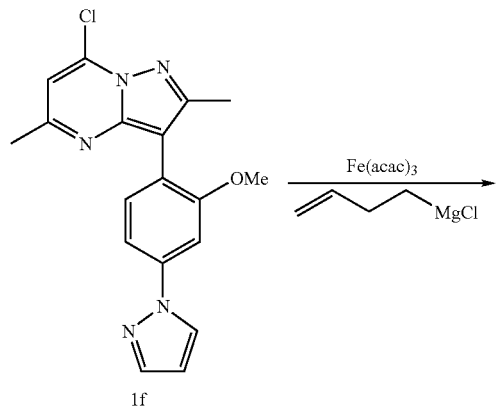

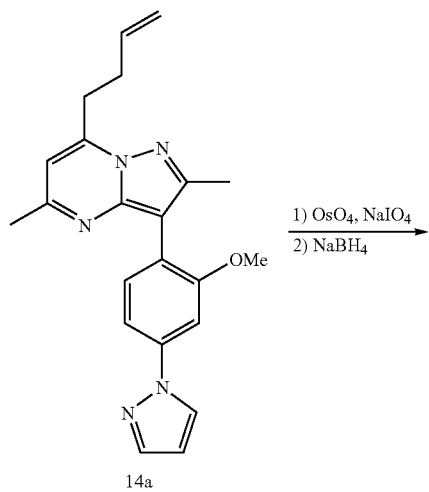

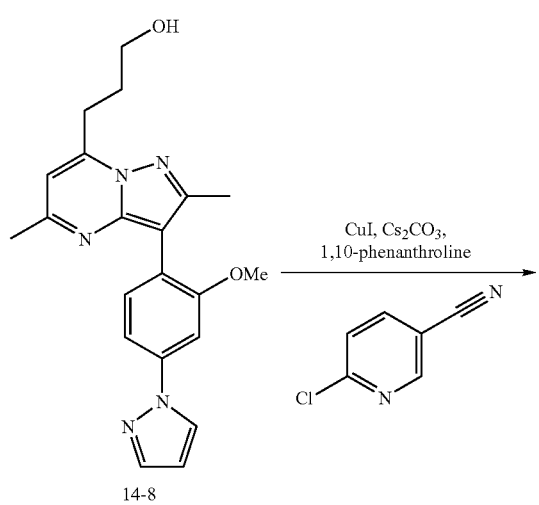

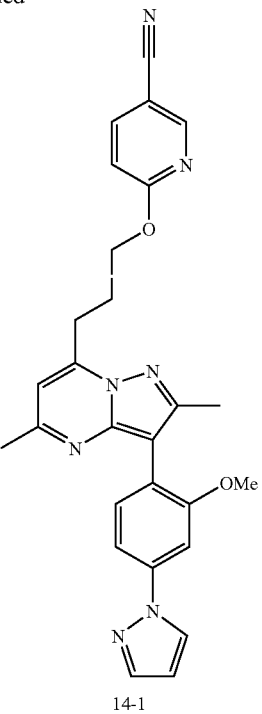

Step 14A:

To a solution of Cmpd 1f (1.06 g, 3.0 mmol) and iron(III) acetylacetonate (353 mg, 1.0 mmol) in 10 mL anhydrous THF/NMP (7:1) was added slowly 3-butenylmagnesium chloride (9.0 mL of a 0.5 M solution in THF, 4.5 mmol). The reaction mixture was stirred at RT for 1 hr, then more iron(III)acetylacetonate (1.0 g, 2.8 mmol) and Grignard reagent (6.0 mL, 3.0 mmol) were added. The reaction mixture was stirred for 2 hr, then water was added. The mixture was extracted with ethyl acetate, then the combined organic layers were dried over sodium sulfate, filtered, and concentrated. The residue was chromatographed on silica gel using hexanes/ethyl acetate as eluent to provide 14a (538 mg, 48% yield).

Step 14B:

To a solution of 14a (380 mg, 1.02 mmol) in 10 mL THF/water (4:1) was added osmium tetroxide (26 mg, 0.10 mmol) followed by sodium periodate (642 mg, 3.0 mmol) at RT. The mixture was stirred at RT for 1 hr, then ethyl acetate and water were added. The organic layer was dried over sodium sulfate, filtered, and evaporated to provide the crude aldehyde, which was dissolved in methanol (20 mL). Sodium borohydride (152 mg, 4.0 mmol) was added portionwise. After stirring at room temperature for 20 min, the reaction mixture was concentrated. The residue was purified by silica gel chromatography, eluting with hexanes/ethyl acetate to provide Cmpd 14-1 (230 mg, 60% yield).

Step 14C:

A mixture of 14-1 (30 mg, 0.08 mmol, 1 eq), copper(I) iodide (15 mg, 0.08 mmol, 1 eq), cesium carbonate (52 mg, 0.16 mmol, 2 eq), and 1,10-phenanthroline (14 mg, 0.08 mmol, 1 eq) was heated in 1 mL of toluene in a sealed vial at 110° C. for 17 hr. The cooled mixture was filtered through Celite®, then concentrated. The residue was purified by silica gel chromatography using hexane/ethyl acetate as eluent to provide 14-2 (5 mg) as a solid.

Depending on the aryl halide used in the method of Step 14C, the compounds listed in the following table in additional to Cmpd 14-1 were synthesized and purified by preparative LC-MS.
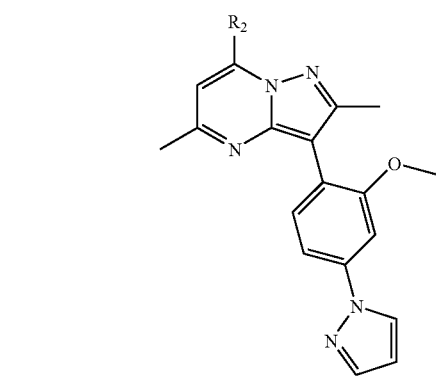
| Cmpd | R₂ | MW | MS | $t_R$* |
|---|---|---|---|---|
| 14-1 | 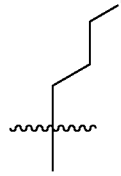 | 377.446 | 377 | 5.170 |
| 14-2 | 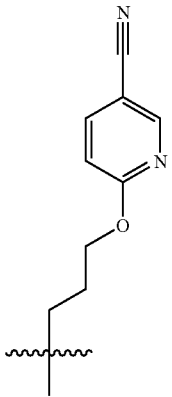 | 479.542 | 479 | 7.570 |
| 14-3 | 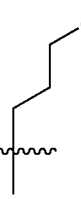 | 523.517 | 523 | 8.020 |
-continued
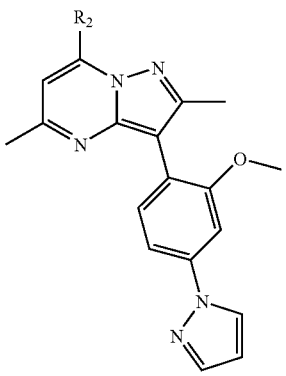
| Cmpd | R₂ | MW | MS | $t_R$* |
|---|---|---|---|---|
| 14-4 | | 522.529 | 522 | 6.620 |
| 14-5 | 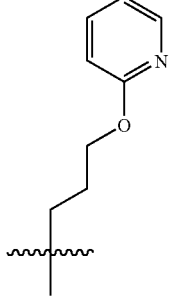 | 479.542 | 479 | 7.350 |
| 14-6 | 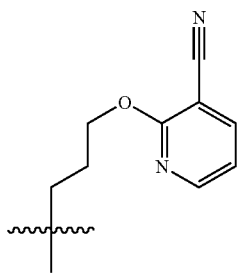 | 507.595 | 507 | 8.320 |
| 14-7 | 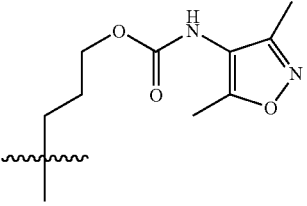 | 515.571 | 515 | 6.510 |

-continued

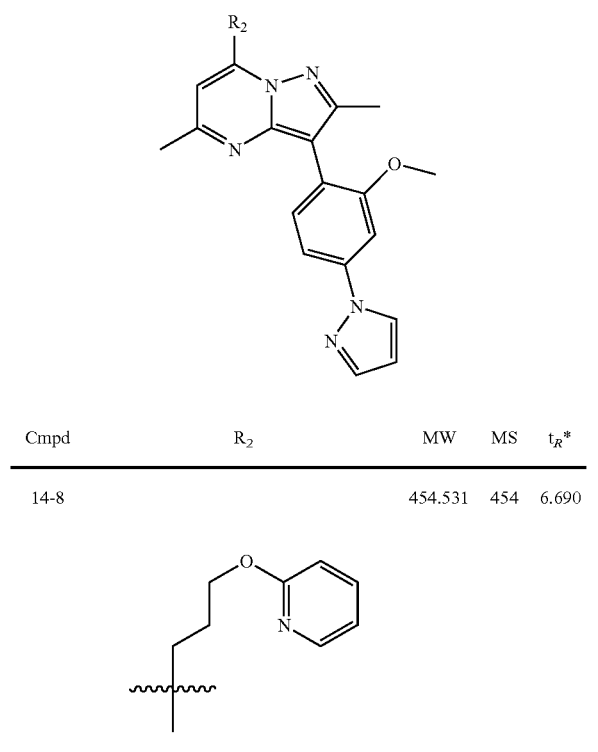

| Cmpd | R₂ | MW | MS | $t_R$* |
|---|---|---|---|---|
| 14-8 | 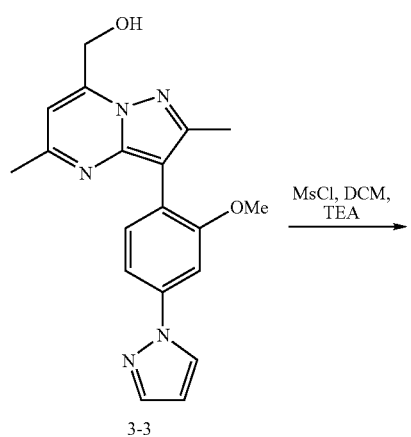 | 454.531 | 454 | 6.690 |

*All HPLC determinations employed Analytical Method 2.

Example 15

7-Imidazol-1-ylmethyl-3-(2-methoxy-4-pyrazol-1-yl-phenyl)-2,5-dimethyl-pyrazolo[1,5-a]pyrimidine

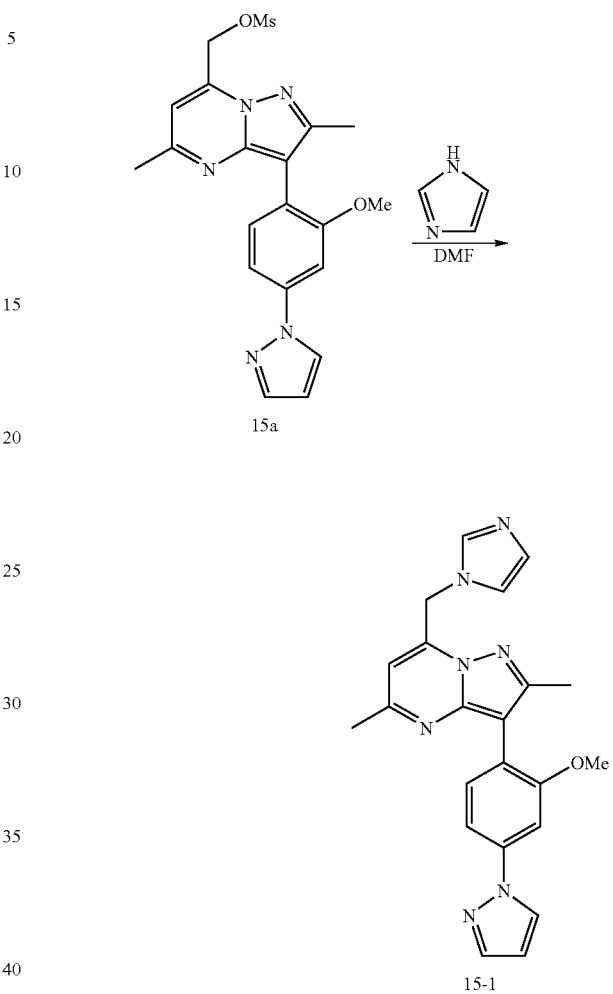

Step 15A:

A solution of methanesulfonyl chloride (100 mg, 0.86 mmol, 1.5 eq) in DCM (0.5 mL) was added dropwise to a 0° C. solution of Cmpd 3-3 (200 mg, 0.57 mmol, 1 eq) in 5 mL DCM. The mixture was allowed to warm to RT over 1 hr, then saturated aqueous sodium bicarbonate solution was added and the mixture was extracted with 2×20 mL DCM. The combined organic layers were dried over sodium sulfate, filtered, and concentrated to obtain 15a (180 mg, 49% yield) as a yellow foam.

Step 15B:

Potassium carbonate (20 mg, 0.14 mmol, 2.6 eq) and imidazole (20 mg, 0.30 mmol, 5.5 eq) were added to a solution of 15a (23 mg, 0.054 mmol, 1 eq) in DMF (1 mL). The reaction mixture was stirred at RT for 16 hr, then methanol (1 mL) was added and the reaction mixture was purified directly by preparative HPLC/MS, providing 15-1 (10 mg) as a TFA salt.

Depending on the nucleophilic heterocycle or amine employed, the compounds listed in the following table were synthesized and purified by preparative LC-MS:

Example 16

4-Methyl-2-pyrrol-1-yl-5-pyridylboronic acid

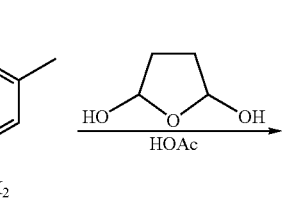

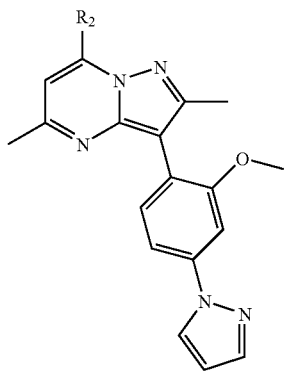

| Cmpd | R₂ | MW | MS | $t_R$* |
|---|---|---|---|---|
| 15-1 | (imidazolylmethyl) | 399.456 | 400 | 4.190 |
| 15-2 | (3-trifluoromethylpyrazolylmethyl) | 467.453 | 468 | 6.320 |
| 15-3 | (pyrazolylmethyl) | 399.456 | 400 | 5.520 |
| 15-4 | (pyrrolidinylmethyl) | 402.499 | 403 | 4.110 |
| 15-5 | (dimethylaminomethyl) | 376.462 | 377 | 3.880 |
| 15-6 | (1,2,4-triazolylmethyl) | 400.444 | 401 | 5.330 |

*All HPLC determinations employed Analytical Method 2.

Step 16A:

A solution of 2-amino-5-bromo-4-methylpyridine (1 g, 5.4 mmol) and 2,5-dihydroxytetrahydrofuran (2.8 g, 27 mmol) in acetic acid (10 mL) was heated at 90° C. in a sealed tube for 2 hr. The reaction mixture was concentrated and the residue was purified by silica gel chromatography using 4:1 hexanes/ethyl acetate, providing 16a (900 mg, 71% yield) as a light yellow oil.

Step 16B:

n-Butyllithium (3.6 mL of a 2.0 M solution in pentane, 7.2 mmol) was added dropwise to a solution of Cmpd 16a (860 mg, 3.6 mmol) and triisopropylborate (1.4 g, 7.3 mmol) in 6 mL THF at −78° C. The mixture was allowed to warm to RT over 1 hr, then 0.5 mL of 4N hydrochloric acid was added and the mixture was stirred for 10 min. The mixture was extracted 2×25 mL DCM, then the organic layer was dried over sodium sulfate, filtered, and concentrated to provide 16-1 (250 mg) as a yellow oil. The aqueous layer was concentrated, then the solid residue was washed with ethanol. The combined ethanol filtrates were concentrated to provide additional 16-1 (500 mg) as a yellow oil.

Example 17

7-Ethyl-2,5-dimethyl-3-{2-[2-(1-methyl-pyrrolidin-2-yl)-ethoxy]-4-pyrazol-1-yl-phenyl}-pyrazolo[1,5-a]pyrimidine

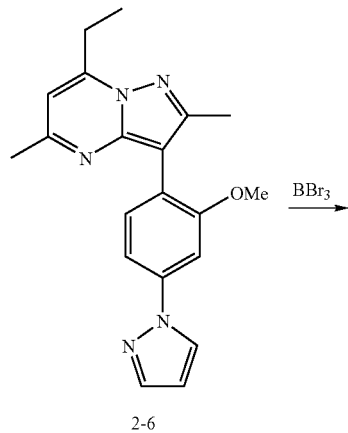

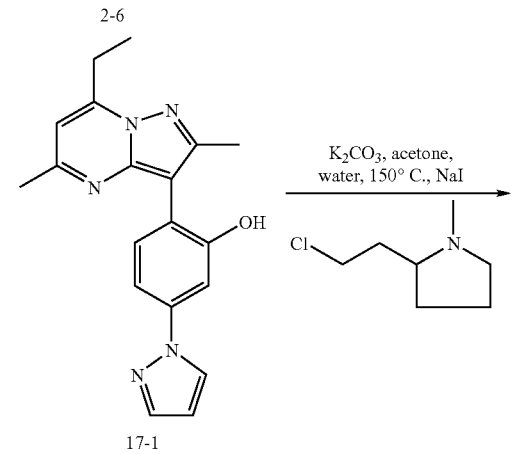

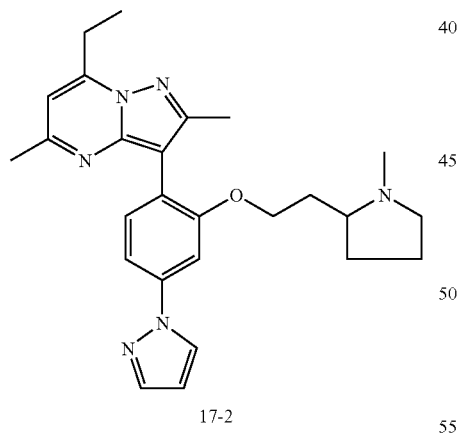

Step 17A:

To a solution of Cmpd 2-6 (350 mg) in chloroform (5 mL) was added BBr$_3$ (1.0 M in DCM, 5 mL.) The mixture was stirred overnight at room temperature and quenched with water. The mixture was extracted with chloroform (2×10 mL), then the combined organic extracts were dried over sodium sulfate, filtered, and concentrated to provide Cmpd 17-1 (280 mg) as an oil. An aliquot (10 mg) was purified by prep HPLC/MS to provide purified Cmpd 17-1 (2.9 mg.)

Step 17B:

A mixture of Cmpd 17-1 (45 mg, 0.14 mmol, 1 eq), potassium carbonate (56 mg, 0.41 mmol, 3 eq), sodium iodide (20 mg, 0.13 mmol, 1 eq), 2-(2-chloroethyl)-1-methylpyrrolidine hydrochloride (39 mg, 0.21 mmol, 1.5 eq), acetone (1 mL) and water (1 mL) was heated in a sealed tube in a microwave reactor at 150° C. for 25 min. The acetone was evaporated, then the residue was diluted with methanol, filtered, and subjected directly to preparative HPLC/MS purification, yielding Cmpd 17-2 (14 mg, 20%) as a TFA salt; MW: 444.58; LC/MS: 444 [MH]$^+$; $t_R$: 6.010, Anal. Meth. 2.

Example 18

7-(3-Methoxy-propyl)-3-(2-methoxy-4-pyrazol-1-yl-phenyl)-2,5-dimethyl-pyrazolo[1,5-a]pyrimidine

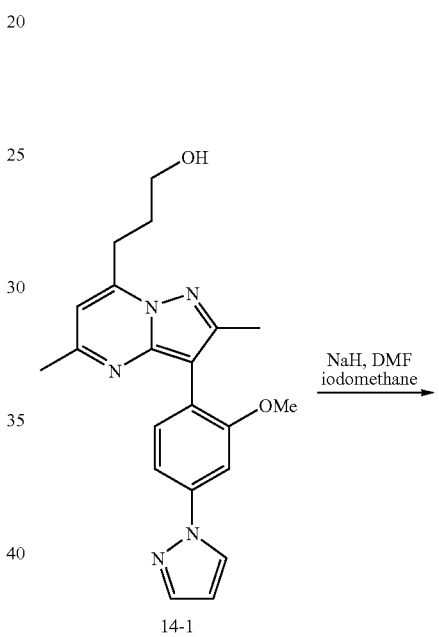

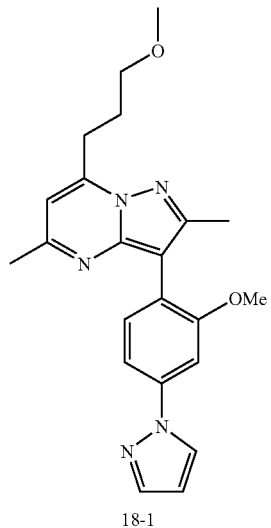

Step 18A:

To a solution of 14-1 (30 mg) in dry DMF was added NaH (10 mg, 60% dispersion). After stirring at RT for 10 min, methyliodide (0.015 mL) was added. The mixture was stirred for 1 hr, then methanol (1 mL) was added and the mixture was subjected directly to prep HPLC/MS purification, providing Cmpd 18-1 (12 mg) as a TFA salt; MW: 391.47 LC/MS: 391 [MH]$^+$; $t_R$: 7.050, Anal. Meth. 2.

Example 19

2-[7-(2-Methoxymethyl-phenyl)-2,5-dimethyl-pyrazolo[1,5-a]pyrimidin-3-yl]-5-pyrazol-1-yl-phenol

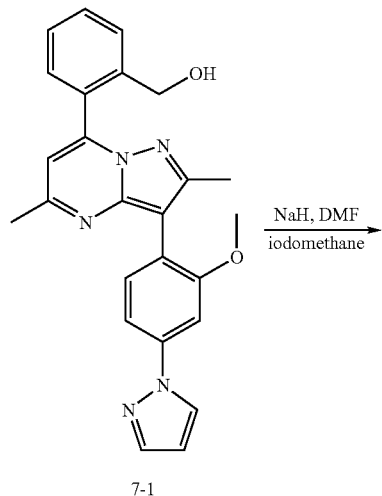

Step 19A:

The procedure of Example 18 was followed using Cmpd 7-1 as starting material

Depending on the alkyl halide employed, the compounds listed in the following table were synthesized and purified by preparative LC-MS.

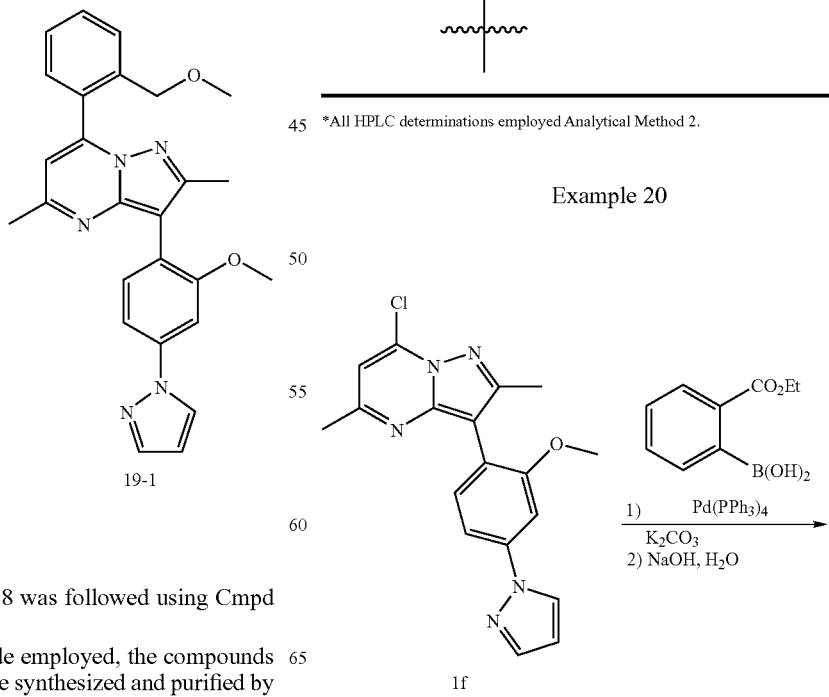

| Cmpd | R$_2$ | MW | MS | $t_R$* |
|---|---|---|---|---|
| 19-1 | 2-(methoxymethyl)phenyl | 439.517 | 439 | 6.130 |
| 19-2 | 2-((2-methoxyethoxy)methyl)phenyl | 483.569 | 483 | 5.980 |
| 19-3 | 2-(ethoxymethyl)phenyl | 453.543 | 453 | 6.290 |

*All HPLC determinations employed Analytical Method 2.

Example 20

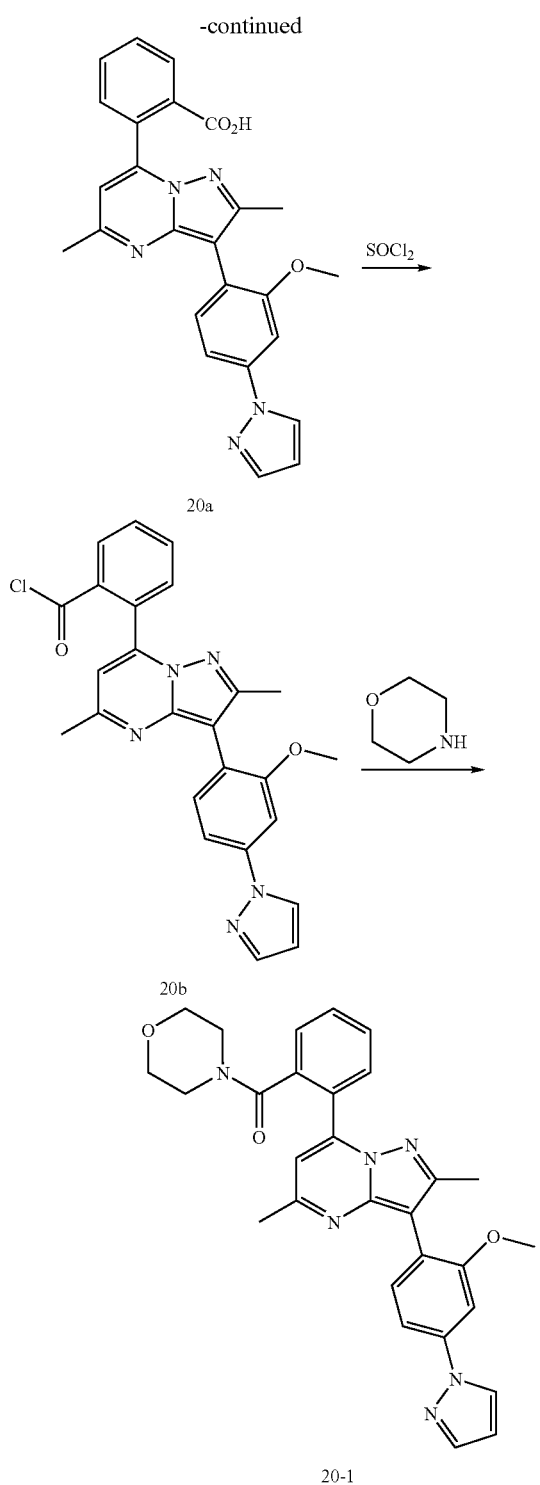

was concentrated, then water was added and the pH adjusted to 2 with hydrochloric acid. The mixture was extracted with chloroform, then the combined chloroform extracts were dried over sodium sulfate, filtered, and concentrated to provide a crude solid, which was recrystallized from chloroform to provide Cmpd 20a (420 mg, 48% yield) as a yellow solid.

Step 20B:

Compound 20a (420 mg, 0.96 mmol) was heated in 10 mL chloroform with thionyl chloride (1.0 mL, 14 mmol) at 70° C. for 2 hr. Volatiles were evaporated to provide Cmpd 20b (450 mg) as a dark solid.

Step 20C:

A solution of 20b (32 mg, 0.07 mmol) in chloroform (1 mL) was treated with morpholine (0.1 mL, 1 mmol) at RT. The mixture was allowed to sit at RT for 30 min, then the solvent was evaporated. The residue was taken up in methanol, filtered and purified directly by preparative HPLC/MS to provide 20-1 (13 mg, 30%) as a TFA salt. Depending on the amine used, the compounds listed in the following table were synthesized and purified by preparative HPLC-MS:

| Cmpd | R$_2$ | MW | MS | t$_R$* |
|---|---|---|---|---|
| 20-1 | | 508.579 | 508 | 6.180 |
| 20-2 | | 506.607 | 506 | 7.050 |
| 20-3 | | 492.58 | 492 | 6.710 |

Step 20A:

A mixture of Cmpd 1f (710 mg, 2.0 mmol), (2-ethoxycarbonyl)phenylboronic acid (470 mg, 2.4 mmol), tetrakis(triphenylphosphine)palladium(0) (116 mg, 0.1 mmol), and potassium carbonate (550 mg, 4.0 mmol) was heated in 9:1 dioxane/water (10 mL) at 100° C. for 2.5 hr. Sodium hydroxide solution (3N, 10 mL) was added, and the mixture was stirred at 100° C. for an additional 30 min. The cooled mixture -continued

| Cmpd | R₂ | MW | MS | t$_R$* |
|---|---|---|---|---|
| 20-4 | (2-cyanoethylaminocarbonyl)phenyl group | 491.552 | 491 | 5.840 |

*All HPLC determinations employed Analytical Method 2.

Example 21

7-(1-Ethyl-1H-pyrrol-2-yl)-3-(2-methoxy-4-pyrazol-1-yl-phenyl)-2,5-dimethyl-pyrazolo[1,5-a]pyrimidine

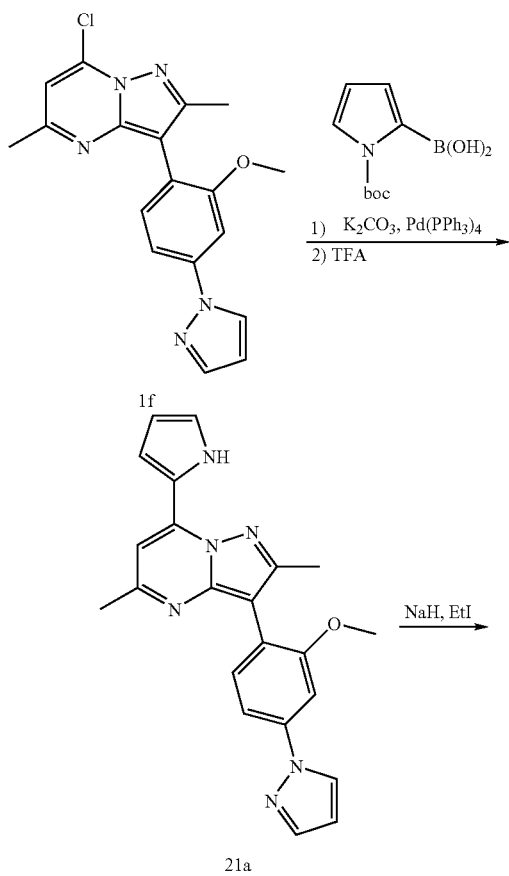

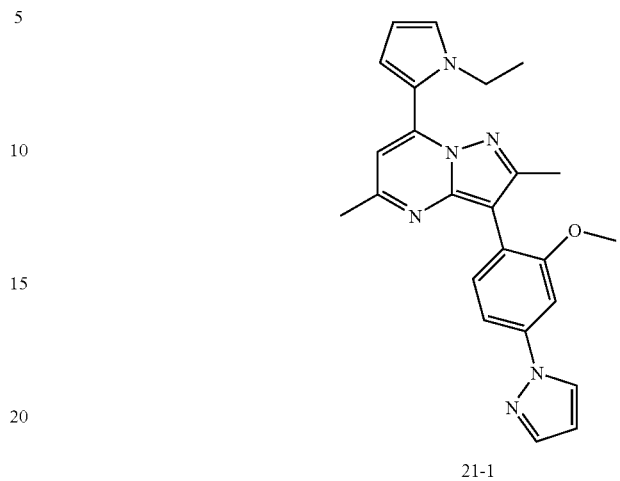

Step 21A:

A mixture of Cmpd 1f (210 mg, 0.6 mmol), N-Boc-pyrrole-2-boronic acid (158 mg, 0.75 mmol), tetrakis(triphenylphosphine)palladium(0) (40 mg, 0.035 mmol), and potassium carbonate (166 mg, 1.2 mmol) was heated in 9:1 dioxane/water (5 mL) at 110° C. for 3 hr in a sealed tube. The cooled mixture was concentrated, then water was added and the mixture was extracted with chloroform. The combined chloroform extracts were dried over sodium sulfate, filtered, and concentrated to provide a crude solid, which was stirred in 1:1 TFA/DCM (3 mL) for 16 hr. The mixture was diluted with ethyl acetate, then treated with aqueous ammonia. The organic layer was dried over sodium sulfate, filtered, and concentrated, then the residue was chromatographed on silica gel using hexanes/ethyl acetate as eluent to provide 21a (110 mg, 48% yield) as a yellow solid.

Step 21B:

To a solution of 21a (110 mg, 0.28 mmol) in dry DMF (2 mL) was added sodium hydride (20 mg of a 60% dispersion in mineral oil, 0.5 mmol) at RT. The mixture was stirred for 5 min, then ethyl iodide (0.050 mL, 0.60 mmol) was added and the mixture was stirred at RT for 2 hr. Water and ethyl acetate were added, then the ethyl acetate layer was washed with water and brine, then dried over sodium sulfate, filtered, and concentrated. The residue was purified by silica gel chromatography using hexanes/ethyl acetate as eluent to provide Cmpd 21-1 (84 mg, 73% yield) as a yellow solid; MW: 412.50 LC/MS: 412 [MH]⁺; t$_R$: 7.630, Anal. Meth. 2.

Example 22

7-(3-Ethyl-3H-imidazol-4-yl)-3-(2-methoxy-4-pyrazol-1-yl-phenyl)-2,5-dimethyl-pyrazolo[1,5-a]pyrimidine

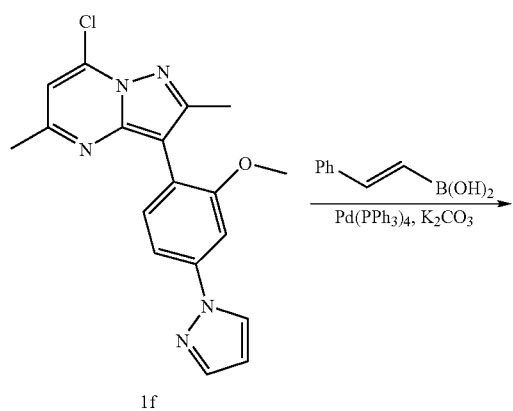

1f

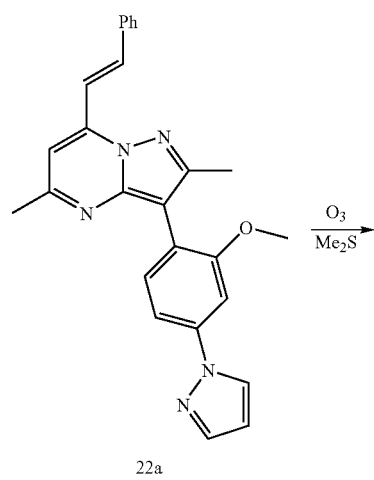

22a

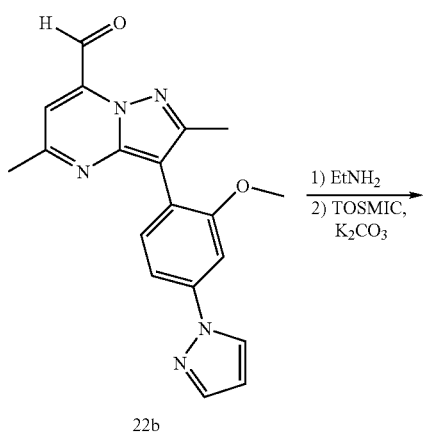

22b

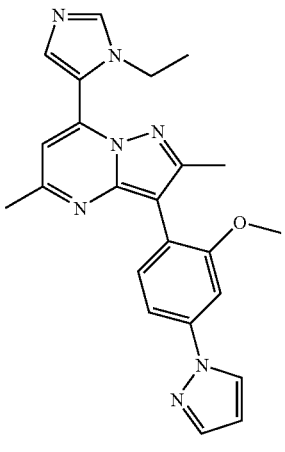

22-1

Step 22A:

A mixture of Cmpd 1f (1.50 g, 4.25 mmol), 2-phenylethenylboronic acid (692 mg, 4.68 mmol), potassium carbonate (1.17 g, 8.50 mmol), and tetrakis (triphenylphosphine)palladium(0) (250 mg, 0.22 mmol) in dioxane (9 mL) and water (1 mL) was heated at 105° C. for 16 hr. The mixture was diluted with ethyl acetate and washed with brine. The organic layer was dried over sodium sulfate, filtered, and concentrated, and the residue was chromatographed on silica gel using hexanes/ethyl acetate as eluent to afford 22a (1.60 g, 89% yield) as a yellow solid.

Step 22B:

An ozone/oxygen mixture was bubbled through a solution of 22a (1.60 g, 3.8 mmol) in dry 2:1 DCM/methanol (20 mL) at −70° C. for 8 minutes. Dimethyl sulfide (1.5 mL) was added and the mixture was stirred and allowed to warm to RT over 16 hr. The solvent was evaporated and the residue was chromatographed on silica gel using hexanes/ethyl acetate as eluent, providing Cmpd 22b (1.0 g, 76% yield) as a yellow solid.

Step 22C:

A mixture of 22b (35 mg, 0.10 mmol), ethylamine (1.0 mL of a 2.0M solution in THF, 2.0 mmol), and magnesium sulfate in 1,2-dichloroethane was stirred at RT for 15 hr. The mixture was filtered, then the filtrate was evaporated to dryness. The residue was taken up in 1:1 ethanol/DME (2 mL), then TOSMIC (38 mg, 0.19 mmol) and potassium carbonate (55 mg, 0.4 mmol) were added and the mixture was refluxed for 17 hr. Water was added and the mixture was extracted with ethyl acetate. The combined organic extracts were dried over sodium sulfate, filtered, and concentrated. The residue was purified by silica gel chromatography using hexanes/ethyl acetate as eluent, providing Cmpd 22-1 (5 mg) as an oil; MW: 413.48 LC/MS: 413 [MH]$^+$; $t_R$: 5.000, Anal. Meth. 2.

Example 23

3-(2-Methoxy-4-pyrazol-1-yl-phenyl)-2,5-dimethyl-7-(4-methyl-oxazol-5-yl)-pyrazolo[1,5-a]pyrimidine

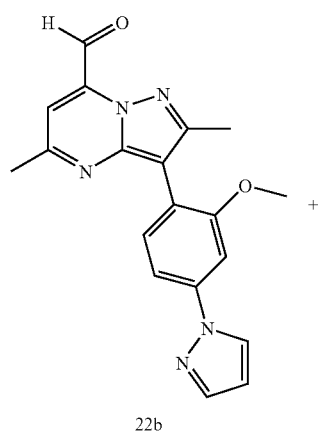

22b

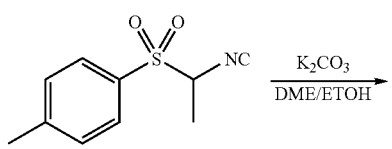

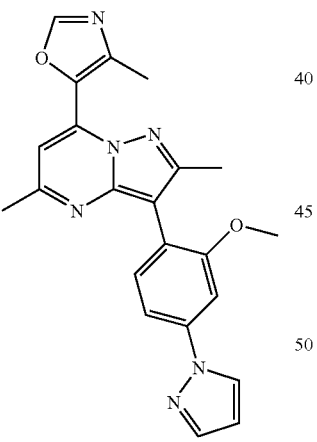

23-1

A mixture of 22b (208 mg, 0.60 mmol), alpha-methyl-TOSMIC (251 mg, 1.2 mmol) and potassium carbonate (248 mg, 1.8 mmol) was heated in 5 mL 1:1 DME/ethanol at 80° C. for 14 hr. Water was added and the mixture was extracted with ethyl acetate. The combined organic extracts were dried over sodium sulfate, filtered, and concentrated. The residue was purified by silica gel chromatography using hexanes/ethyl acetate as eluent, providing 23-1 (60 mg, 23%) as an oil; MW: 400.44 LC/MS: 400 [MH]$^+$; $t_R$: 5.250, Anal. Meth. 2.

Example 24

7-(4-Fluoro-benzyl)-2,5-dimethyl-3-(4-methyl-6-pyrrol-1-yl-pyridin-3-yl)-pyrazolo[1,5-a]pyrimidine

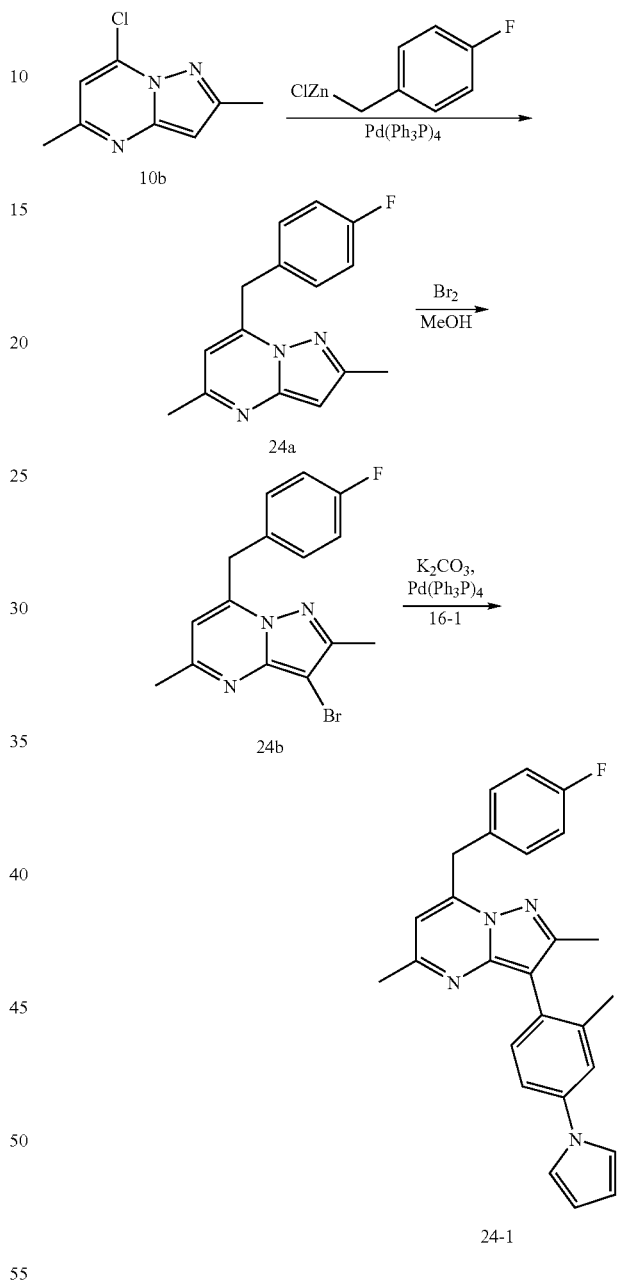

Step 24A:

To a solution of 4-fluorophenylzinc chloride (20 mL of a 0.5 M solution in THF, 10 mmol) were added Cmpd 10b (1.0 g, 5.5 mmol) and tetrakis(triphenylphosphine)palladium(0) (300 mg, 0.26 mmol). The reaction mixture was heated at 90° C. in a sealed tube for 3 hr. The cooled reaction mixture was treated with 4N hydrochloric acid (4 mL), then water was added and the mixture was extracted with ethyl acetate. The combined organic layers were dried over sodium sulfate, filtered, and concentrated. The residue was purified by silica gel chromatography, eluting with 30% ethyl acetate in hexanes to obtain 24a (1.0 g, 71% yield) as an off-white solid.

Step 24B:

Compound 24a (1.0 g, 3.9 mmol) was dissolved in 15 mL methanol. Bromine (0.62 g, 3.9 mmol) was added dropwise to the solution, resulting in formation of a white precipitate. The solid was collected on a fritted glass filter and rinsing with methanol. This compound was further purified by silica gel column chromatography, eluting with 4:1 hexanes/ethyl acetate to provide first a dibromination product (110 mg, 7% yield), followed by 24b (1.0 g, 77% yield) as a white solid.

Step 24C:

A mixture of Cmpd 24b (800 mg, 2.4 mmol), Cmpd 16-1 (500 mg, 2.5 mmol), tetrakis(triphenylphosphine)palladium (0) (280 mg, 0.24 mmol), and potassium carbonate (600 mg, 4.3 mmol) was heated in 9:1 dioxane/water (3.5 mL) at 95° C. for 3 hr in a sealed tube. Aqueous sodium bicarbonate solution (5 mL) was added to the cooled mixture, which was then extracted twice with DCM. The combined DCM extracts were dried over sodium sulfate, filtered, and concentrated to provide a crude oil, which was partially purified by prep HPLC/MS. The partially purified product was then chromatographed on silica gel using 4:1 hexanes/ethyl acetate as eluent, providing Cmpd 24-1 (3 mg) as a yellow solid; MW: 411.48 LC/MS: 412 [MH]$^+$; t$_R$: 9.160, Anal. Meth. 2.

Example 25

3-(2-Methoxy-4-pyrazol-1-yl-phenyl)-2,5-dimethyl-7-(1-methyl-1H-imidazol-2-yl)-pyrazolo[1,5-a]pyrimidine

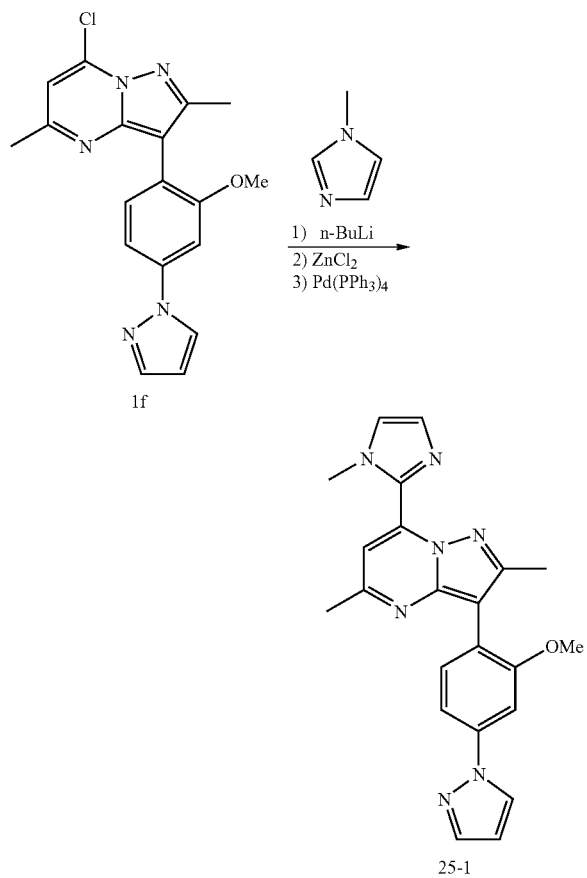

Step 25A:

To a solution of 1-methylimidazole (246 mg, 3.0 mmol) in dry THF (3 mL) cooled to −70° C. was added n-BuLi (2.5 M solution in hexane, 1.7 mL, 4.2 mmol) dropwise. The reaction mix was stirred at −70° C. for 10 min, then ZnCl$_2$ (0.5 M solution in THF, 20 mL, 10 mmol) was added over 5 min. The mixture was stirred at −70° C. for 1 hr, then was warmed to 0° C. Cmpd 1f (106 mg, 0.30 mmol) and tetrakis(triphenylphosphine)palladium(0) (70 mg, 0.06 mmol) were added. The mixture was then heated to reflux for 3 hr. The cooled reaction mixture was quenched with water, the THF was evaporated and the resulting aqueous mixture was extracted with ethyl acetate. The combined organic layers were dried over sodium sulfate, filtered, concentrated, and the residue was chromatographed on silica gel using ethyl acetate as eluant to give 25-1 (15 mg) as a yellow solid; HPLC retention time 4.13 min (method 2); MW 399.5; observed MS 399.

Example 26

3-(2-Methoxy-4-pyrazol-1-yl-phenyl)-2,5-dimethyl-7-(2-methyl-2H-pyrazol-3-yl)-pyrazolo[1,5-a]pyrimidine

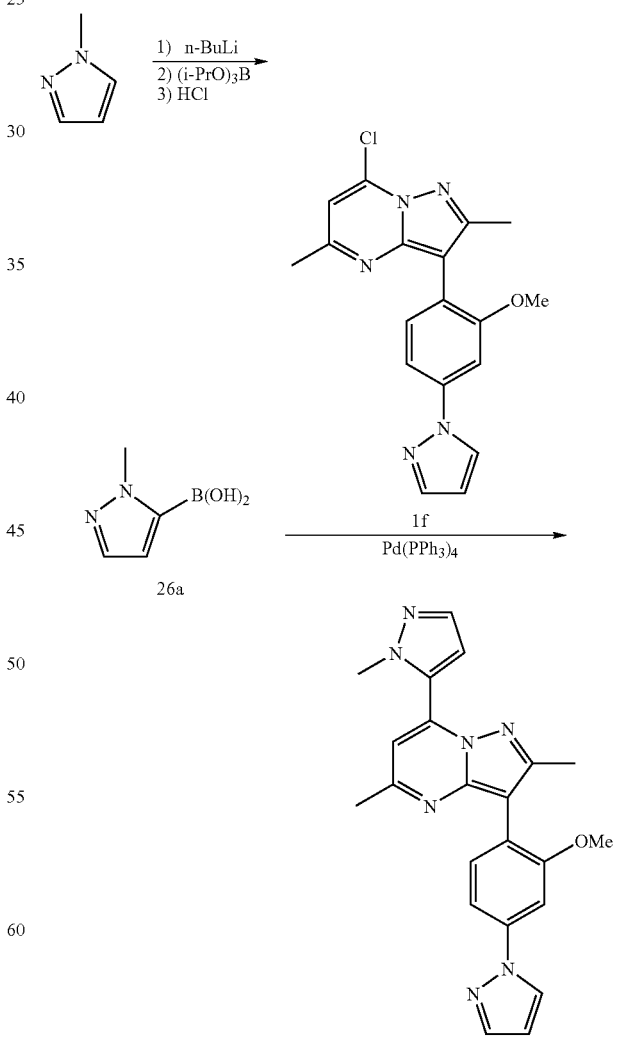

Step 26A:

To a solution of 1-methylpyrazole (820 mg, 10 mmol) in dry THF (20 mL) cooled to −70° C. was added n-BuLi (1.6 M solution in hexane, 6.3 mL, 10 mmol) dropwise. The reaction mix was stirred at −70° C. for 5 min, then triisopropyl borate (2.5 mL, 11 mmol) was added over 5 min. The mixture was allowed to warm to RT over 1 hr, then 6N hydrochloric acid (5 ml) was added. The mixture was stirred for 30 min, then was evaporated to dryness to provide crude 26a as a solid, which was used without further purification.

Step 26B:

Cmpd 1f (530 mg, 1.5 mmol) and crude 26a (entire amount, approximately 10 mmol) were subjected to Suzuki reaction according to the procedure of Example 1. The reaction mixture was concentrated, then water was added and the mixture was extracted with chloroform. The combined organic extracts were dried over sodium sulfate, filtered, and concentrated, then the residue was purified by silica gel chromatography using hexanes/ethyl acetate as eluant. The product was further purified by crystallization from acetonitrile, providing Cmpd 26-1 (280 mg) as a yellow solid; HPLC retention time 6.42 min (method 2); MW 399.5; observed MS 399)

Example 27

CRF Receptor Binding Activity

The compounds of this invention may be evaluated for binding activity to the CRF receptor by a standard radioligand binding assay as generally described by Grigoriadis et al. (*Mol. Pharmacol* vol 50, pp 679-686, 1996) and Hoare et al. (*Mol. Pharmacol* vol 63 pp 751-765, 2003.) By utilizing radiolabeled CRF ligands, the assay may be used to evaluate the binding activity of the compounds of the present invention with any CRF receptor subtype.

Briefly, the binding assay involves the displacement of a radiolabeled CRF ligand from the CRF receptor. More specifically, the binding assay is performed in 96-well assay plates using 1-10 µg cell membranes from cells stably transfected with human CRF receptors. Each well receives about 0.05 mL assay buffer (e.g., Dulbecco's phosphate buffered saline, 10 mM magnesium chloride, 2 mM EGTA) containing compound of interest or a reference ligand (for example, sauvagine, urocortin I or CRF), 0.05 mL of [$^{125}$I]tyrosine-sauvagine (final concentration ~150 pM or approximately the $K_D$ as determined by Scatchard analysis) and 0.1 mL of a cell membrane suspension containing the CRF receptor. The mixture is incubated for 2 hr at 22° C. followed by separation of the bound and free radioligand by rapid filtration over glass fiber filters. Following three washes, the filters are dried and radioactivity (Auger electrons from $^{125}$I) is counted using a scintillation counter. All radioligand binding data may be analyzed using the non-linear least-squares curve-fitting programs Prism (GraphPad Software Inc) or XLfit (ID Business Solutions Ltd).

Example 28

CRF-Stimulated Adenylate Cyclase Activity

The compounds of the present invention may also be evaluated by various functional testing. For example, the compounds of the present invention may be screened for CRF-stimulated adenylate cyclase activity. An assay for the determination of CRF-stimulated adenylate cyclase activity may be performed as generally described by Battaglia et al. (*Synapse* 1:572, 1987) with modifications to adapt the assay to whole cell preparations.

More specifically, the standard assay mixture may contain the following in a final volume of 0.1 mL: 2 mM L-glutamine, 20 mM HEPES, and 1 mM IMBX in DMEM buffer. In stimulation studies, whole cells with the transfected CRF receptors are plated in 96-well plates and incubated for 30 min at 37° C. with various concentrations of CRF-related and unrelated peptides in order to establish the pharmacological rank-order profile of the particular receptor subtype. Following the incubation, cAMP in the samples is measured using standard commercially available kits, such as cAMP-Screen™ from Applied Biosystems. For the functional assessment of the compounds, cells and a single concentration of CRF or related peptides causing 50% stimulation of cAMP production are incubated along with various concentrations of competing compounds for 30 min at 37° C., and cAMP determined as described above.

It will be appreciated that, although specific embodiments of the invention have been described herein for purposes of illustration, various modifications may be made without departing from the spirit and scope of the invention. Accordingly, the invention is not limited except as by the appended claims.

What is claimed is:

1. A compound represented by the following formula

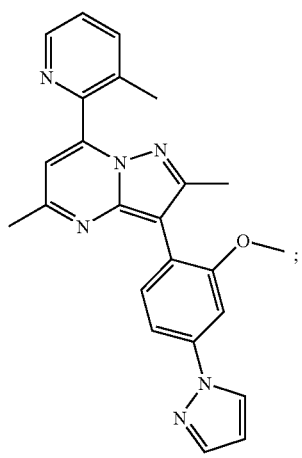

or an acid addition salt thereof.

2. A compound represented by the following formula

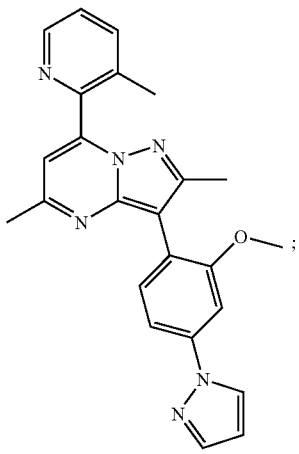

or a pharmaceutically acceptable salt thereof.

3. A pharmaceutical composition comprising a compound according to claim 2, or a pharmaceutically acceptable salt thereof, in combination with a pharmaceutically acceptable carrier or diluent.

4. The pharmaceutical composition according to claim 3 formulated for oral administration.

5. A method for treating depression comprising administering to a mammal in need of treatment thereof an effective amount of a compound according to claim 2, or a pharmaceutically acceptable salt thereof.

6. The method according to claim 5, wherein the mammal is a human.

7. A method for treating anxiety comprising administering to a mammal in need of treatment thereof an effective amount of a compound according to claim 2, or a pharmaceutically acceptable salt thereof.

8. The method according to claim 7, wherein the mammal is a human.

9. A method for treating irritable bowel syndrome comprising administering to a mammal in need of treatment thereof an effective amount of a compound according to claim 2, or a pharmaceutically acceptable salt thereof.

10. The method according to claim 9, wherein the mammal is a human.

11. A compound represented by the following formula

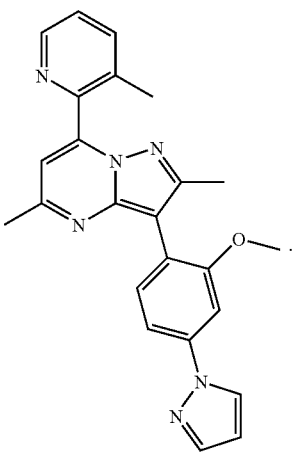

12. A pharmaceutical composition comprising a compound according to claim 11 in combination with a pharmaceutically acceptable carrier or diluent.

13. The pharmaceutical composition according to claim 12 formulated for oral administration.

14. A method for treating depression comprising administering to a mammal in need of treatment thereof an effective amount of a compound according to claim 11.

15. The method according to claim 14, wherein the mammal is a human.

16. A method for treating anxiety comprising administering to a mammal in need of treatment thereof an effective amount of a compound according to claim 11.

17. The method according to claim 16, wherein the mammal is a human.

18. A method for treating irritable bowel syndrome comprising administering to a mammal in need of treatment thereof an effective amount of a compound according to claim 11.

19. The method according to claim 18, wherein the mammal is a human.

* * * * *